United States Patent
Cheng et al.

(10) Patent No.: US 12,428,423 B2
(45) Date of Patent: *Sep. 30, 2025

(54) 1H-IMIDAZO[4,5-H]QUINAZOLINE COMPOUND AS PROTEIN KINASE INHIBITOR

(71) Applicant: SHENGKE PHARMACEUTICALS (JIANGSU) LTD., Jiangsu (CN)

(72) Inventors: Hang Cheng, Sichuan (CN); Bin Liu, San Diego, CA (US); Chenggang Zhang, Jiangsu (CN); Chengzhi Yu, San Diego, CA (US)

(73) Assignee: SHENGKE PHARMACEUTICALS (JIANGSU) LTD., Suzhou (CN)

( * ) Notice: Subject to any disclaimer, the term of this patent is extended or adjusted under 35 U.S.C. 154(b) by 1369 days.

This patent is subject to a terminal disclaimer.

(21) Appl. No.: 16/499,771

(22) PCT Filed: Mar. 30, 2018

(86) PCT No.: PCT/CN2018/081273
§ 371 (c)(1),
(2) Date: Jul. 2, 2021

(87) PCT Pub. No.: WO2018/177403
PCT Pub. Date: Oct. 4, 2018

(65) Prior Publication Data
US 2022/0315584 A1    Oct. 6, 2022

(30) Foreign Application Priority Data
Apr. 1, 2017  (CN) .................. 201710213777.X

(51) Int. Cl.
*C07D 487/02* (2006.01)
*A61P 35/00* (2006.01)

(52) U.S. Cl.
CPC ............ *C07D 487/02* (2013.01); *A61P 35/00* (2018.01)

(58) Field of Classification Search
CPC .................. C07D 487/02; A61P 35/00
See application file for complete search history.

(56) References Cited

U.S. PATENT DOCUMENTS

| | | | | |
|---|---|---|---|---|
| 7,576,091 B2 * | 8/2009 | McInnes | ................. | A61P 43/00 |
| | | | | 544/251 |
| 11,091,485 B2 * | 8/2021 | Liu | ....................... | C07D 471/14 |
| 11,319,323 B2 * | 5/2022 | Liu | .......................... | A61P 35/00 |
| 11,993,604 B2 * | 5/2024 | Liu | ..................... | A61K 31/5377 |

FOREIGN PATENT DOCUMENTS

| | | | | |
|---|---|---|---|---|
| WO | 2005/005438 A1 | 1/2005 | | |
| WO | WO-2005037843 A1 * | 4/2005 | .......... | A61K 31/496 |
| WO | 2009/046448 A1 | 4/2009 | | |
| WO | 2010/129858 A1 | 11/2010 | | |
| WO | 2012/101032 A1 | 8/2012 | | |

OTHER PUBLICATIONS

International Search Report and Written Opinion for Application No. PCT/CN2018/081273, dated Jun. 27, 2018, 22 pages.

* cited by examiner

*Primary Examiner* — Clinton A Brooks
*Assistant Examiner* — Izabela Schmidt
(74) *Attorney, Agent, or Firm* — McCarter & English, LLP; Xin Zhang

(57) ABSTRACT

Provided is a 1H-imidazo[4,5-h]quinazoline compound of formula (I). The compound is a broad spectrum inhibitor having strong activity for cyclin-dependent kinase (CDK) and is applicable in treating cell proliferative disorder

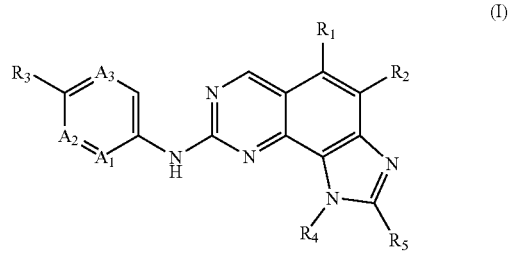

18 Claims, No Drawings

1H-IMIDAZO[4,5-H]QUINAZOLINE COMPOUND AS PROTEIN KINASE INHIBITOR

CROSS REFERENCE TO RELATED APPLICATIONS

The present application is a national application of PCT/CN2018/081273 filed on Mar. 30, 2018, which claims the priority of the Chinese Patent Application No. 201710213777.X filed on Apr. 1, 2017. The Chinese Patent Application No. 201710213777.X is incorporated herein by reference as part of the disclosure of the present application.

TECHNICAL FIELD

The present disclosure provides a 1H-imidazo[4,5-h]quinazoline compound as a cyclin-dependent kinase (CDK) inhibitor, which has a broad-spectrum and strong inhibitory activity against CDK. The compound of the present disclosure is effective in the treatment of diseases such as cancer and inflammation.

BACKGROUND

Cancer is the second leading cause of death all over the world. The World Cancer Report 2014 published by World Health Organization discloses that cancer patients and deaths worldwide are increasing uncomfortably. Nearly half of new cancer cases appear in Asia, most of which are in China. The Report also predicts that cancer cases worldwide will show rapid growth as from 14 million in 2012 to 19 million in 2025, and will reach 24 million in 2035, of which China will account for 21.9% of the global number. According to institutional data, in the past 30 years, in China, cancer mortality rate has increased by 80%, the annual incidence of cancer is about 2.6 million, and the death toll is about 1.8 million.

Cell cycle is an important part of the life of a cell. Studies have found that the occurrence and development of a variety of malignant tumors are closely associated with the disorder of cell cycle regulation mechanism, so tumors are also considered as a disease of the cell cycle. Since 1970s, three scientists in the United States and the United Kingdom have won the 2001 Nobel Prize in Physiology/Medical for discovering the important role of cyclin-dependent kinases and cyclins in cell regulation. With the continuous progress in the research of cell cycle regulation mechanism, especially the core importance of CDK in cell cycle regulation, cyclin-dependent kinases have become a research hotspot of the current anticancer drugs.

Cyclin-dependent kinases are a class of serine (Ser)/threonine (Thr) kinases. As important signal transduction molecules in cells, they form CDK-cyclin complex together with cyclins to participate in cell growth, reproduction, dormancy or apoptosis (Morgan D. O., *Annu. Rev. Cell. Dev. Biol.* 1997; 13261-13291). Unlike other kinases, CDK must form a corresponding dimeric complex with cyclins to function. Cyclins are periodically expressed and degraded continuously, and bind to CDKs that are transiently activated by them, and catalyze the phosphorylation of different substrates through CDK's activity, thereby realizing the promotion and transformation of different phases in the cell cycle. In addition, CDK can also bind to CDK inhibitive factors to block cell division. Thirteen CDK members (CDK1 to CDK13) have been identified in the human body, as well as 12 corresponding cyclins (A to L). It is currently believed that CDK 1, 2, 4, 6 and 7 are mainly responsible for the regulation of the cell cycle.

It has shown that the increased activity of cyclin-dependent kinases or transient abnormalities in activation results in the formation of human tumors (Sherr C. J., *Science* 1996; 274:1672-1677). In fact, the formation of human tumors is generally associated with changes in the CDK protein itself or its modulators (Cordon-Cardo C., *Am. J. Pathol.* 1995; 147, 545-560; Karp J. E. and Broder S., *Nat. Med.* 1995; 1: 309-320; Hall. M. et al., *Adv. Cancer Res.* 1996; 68: 67-108). Naturally occurring protein inhibitors of CDK such as p16 and p27 lead to in vitro growth inhibition of lung cancer cell lines (Kamb A., *Curr. Top. Microbiol. Immunol.* 1998; 227: 139-148). Small molecular CDK inhibitors can also be used to treat cardiovascular disorders such as restenosis and atherosclerosis and other vascular disorders caused by abnormal cell proliferation. Vascular smooth muscle proliferation and intimal hyperplasia secondary to balloon angioplasty are inhibited by overexpression of the cyclin-dependent kinase inhibitor p21 protein (Chang M. W. et al., J. Clin. Invest., 1995; 96: 2260; Yang Z-Y. et al., Proc. Natl. Acad. Sci. 1996; 93: 9905). Moreover, the purine CDK2 inhibitor CVT-313 (Ki=95 nM) results in inhibition of neointimal formation in rats by more than 80% (Brooks E. E. et al., *J. Biol. Chem.* 1997: 29207-29211). CDK inhibitors can be used to treat diseases caused by a variety of infectious agents, including fungi, protozoan parasites (such as *Plasmodium falciparum*), and DNA and RNA viruses. For example, cyclin-dependent kinases are required for viral replication secondary to herpes simplex virus (HSV) infection (Schang L. M. et al., *J. Virol.* 1998; 72: 5626), and CDK homologs are known to play a key role in yeast. Selective CDK inhibitors can be used to ameliorate the consequences of various autoimmune disorders. Chronic inflammatory disease, rheumatoid arthritis, is characterized by synovial tissue hyperplasia; inhibition of synovial tissue proliferation minimizes the inflammation and prevents joint destruction. Expression of the CDK inhibitor p16 protein in synovial fibroblasts causes growth inhibition (Taniguchi K. et al., Nat. Med. 1999; 5:760-767). Similarly, in a rat model of arthritis, joint swelling is substantially inhibited by p16-expressing adenovirus treatment. CDK inhibitors are effective against other cell proliferation disorders, including psoriasis (characterized by hyperproliferation of keratinocytes), glomerulonephritis, and lupus. Certain CDK inhibitors can be used as chemoprotectants considering their ability to inhibit cell cycle progression in normal untransformed cells (Chen et al., *J. Nat. Cancer institute*, 2000; 92: 1999-2008). Pre-treatment of cancer patients with CDK inhibitors prior to the use of cytotoxic agents can reduce the side effects commonly associated with chemotherapy. Tissues in normal proliferation are protected by the action of selective CDK inhibitors from cytotoxicity. Review articles on small molecular inhibitors of cyclin-dependent kinases have noted that it is difficult to identify compounds that specifically inhibit CDK proteins without inhibiting other enzymes.

Selective and targeted drugs for CDK4 and/or CDK6 may play a role in several mechanisms as below: (1) CDK4 gene amplification or high protein expression, which is frequently found in highly differentiated and dedifferentiated liposarcoma, and also in some other solid tumors and hematological malignancies; (2) amplification or high expression of cyclin D1, which is observed in mantle cell lymphoma, and also in various solid tumors; (3) loss of the p16 INK4A gene (CDKN2A), which is also a common event in many cancers. In cells, the p16 INK4A protein is a natural inhibitor of CDK4, and cancers with a loss of p16 are generally susceptible to inhibition of CDK4. For example, in ovarian cancer, these cancer cell lines have low p16 protein levels and high Rb expression, which are sensitive to inhibitors of CDK4. Because of the high similarity of the proteins of CDK6 and CDK4, current CDK4 inhibitors also have similar inhibitory effects on CDK6 protein kinase. Currently, there are three CDK4/CDK6 inhibitors that have entered clinical trials: palbociclib (PD0332991), LEE011 and LY2835219. These inhibitors prevent CDK4/6 from forming complexes with cyclin D, effectively blocking the cell cycle from the G1 phase to the S phase, thereby achieving the goal of inhibiting tumor cell proliferation, and exhibiting anti-tumor activity when used alone or in combination with other targeted drugs in breast cancer, neuroblastoma, malignant rhabdomyomas, lymphoma, sarcoma and other tumors.

In addition to selective inhibitors of CDK4 and CDK6, pan-CDK inhibitors such as Dinaciclib (SCH-727965, MK-7965), which have inhibitory activities against all CDK1, CDK2, CDK5, CDK9 and CDK12, have also entered clinical trials, exhibiting promising anticancer activity in the targeted therapy of the solid tumor.

SUMMARY OF THE INVENTION

The present disclosure provides 1H-imidazo[4,5-h]quinazoline compounds as inhibitors of the cyclin-dependent kinase, which have a broad-spectrum and strong inhibitory activity. The compounds disclosed herein are effective in the treatment of cell proliferative disorders such as restenosis, cancer and inflammation. Compared to known drugs, the compounds of the present disclosure are capable of further improving pharmacokinetic properties, including the significant improvement in the metabolic stability and clearance over known compounds. Furthermore, the compounds disclosed herein can be readily synthesized and administered to a patient by a variety of methods.

In one aspect, the present disclosure provides a compound of formula (I), or a pharmaceutically acceptable salt, enantiomer, diastereomer, racemate, or mixture thereof:

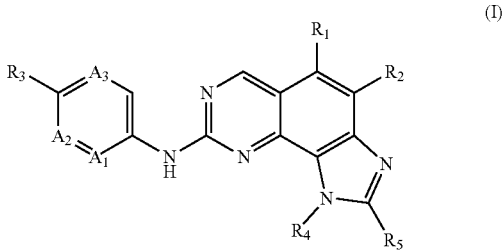

(I)

wherein:
$A_1$ is selected from $CR_3$ or N;
$A_2$ is selected from $CR_3$ or N;
$A_3$ is selected from $CR_3$ or N;
$R_1$ is selected from H, halogen, —CN, —$OR_a$, —$SR_a$, —$NR_bR_c$, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted with oxo or thioxo;
$R_2$ is selected from H, halogen, —CN, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted with oxo or thioxo;
$R_3$ is selected from H, halogen, —CN, —$NO_2$, -L-$OR_a$, -L-$SR_a$, -L-$NR_bR_c$, -L-$C(O)R_a$, -L-$C(O)OR_a$, -L-$C(O)NR_bR_c$, -L-$S(O)_mR_a$, -L-$S(O)_mOR_a$, -L-$S(O)_mNR_bR_c$, —O—$C_{1-6}$ alkylene-$R_6$, $C_{1-6}$ alkyl, $C_{1-6}$ haloalkyl, -L'-$C_{3-7}$ cycloalkyl, -L'-3- to 11-membered heterocyclyl, -L'-$C_{6-10}$ aryl, or -L'-5- to 10-membered heteroaryl, each of which is optionally substituted with 1, 2, 3, 4 or 5 $R_6$ groups;
$R_4$ is selected from —$C(O)R_a$, —$C(O)OR_a$, —$C(O)NR_bR_c$, $C_{1-6}$ alkyl, $C_{1-6}$ haloalkyl, $C_{3-7}$ cycloalkyl, or 3- to 7-membered heterocyclyl;
$R_5$ is selected from H, halogen, —CN, —$OR_a$, —$SR_a$, —$NR_bR_c$, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted with oxo or thioxo;
$R_6$ is selected from H, —$NH_2$, —$NHC_{1-6}$ alkyl, —$N(C_{1-6}$ alkyl$)_2$, $C_{1-6}$ alkyl, $C_{1-6}$ haloalkyl, —$C_{1-6}$ alkylene-$OR_a$, -L-$C_{3-7}$ cycloalkyl, -L-3- to 7-membered heterocyclyl, -L-$C_{6-10}$ aryl, or -L-5- to 10-membered heteroaryl;
or two $R_6$ groups on the same carbon atom are taken together to form oxo or thioxo;
wherein:
$R_4$ is optionally substituted with 1, 2 or 3 R' groups, wherein R' is independently selected from H, halogen, —CN, —$NO_2$, —$OR_a$, —$SR_a$, —$NR_bR_c$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl;
each of $R_3$, $R_5$ and $R_6$ is optionally substituted with 1, 2 or 3 R" groups, wherein R" is independently selected from H, —OH, halogen, —$NO_2$, carbonyl, -L-CN, -L-$OR_a$, -L-$SR_a$, -L-$NR_bR_c$, -L-$C(O)R_a$, -L-$C(S)R_a$, -L-$C(O)OR_a$, -L-$C(S)OR_a$, -L-$C(O)$—$NR_bR_c$, -L-$C(S)$—$NR_bR_c$, -L-O—$C(O)R_a$, -L-O—$C(S)R_a$, -L-N$(R_b)$—$C(O)$—$R_a$, -L-N$(R_b)$—$C(S)$—$R_a$, -L-$S(O)_mR_a$, -L-$S(O)_mOR_a$, -L-$S(O)_mNR_bR_c$, -L-N$(R_b)$—$S(O)_m$—$R_a$, -L-N$(R_b)$—$S(O)_m$—$NR_bR_c$, -L-N$(R_b)$—$C(O)OR_a$, -L-N$(R_b)$—$C(S)OR_a$, -L-O—$C_{1-6}$ alkylene-$OR_a$, -L-$C(O)$—$C_{1-6}$ alkylene-$NR_bR_c$, -L-N$(R_b)$—$C(O)$—$NR_bR_c$, -L-N$(R_b)$—$C(S)$—$NR_bR_c$, -L-O—$C(O)$—$NR_bR_c$, -L-O—$C(S)$—$NR_bR_c$, $C_{1-6}$ alkyl, $C_{1-6}$ haloalkyl, $C_{2-6}$ alkenyl, $C_{2-6}$ alkynyl, -L-$C_{3-7}$ cycloalkyl, -L-3- to 7-membered heterocyclyl, -L-$C_{6-10}$ aryl, or -L-5- to 10-membered heteroaryl; wherein the said $C_{1-6}$ alkyl, $C_{1-6}$ haloalkyl, $C_{2-6}$ alkenyl, $C_{2-6}$ alkynyl, -L-$C_{3-7}$ cycloalkyl, -L-3- to 7-membered heterocyclyl, -L-$C_{6-10}$ aryl, or -L-5- to 10-membered heteroaryl is each optionally further substituted with one or more substituents independently selected from the group consisting of -L-CN, —$NO_2$, carbonyl, -L-$OR_a$, -L-$SR_a$, -L-$NR_bR_c$, -L-$C(O)R_a$, -L-$C(S)R_a$, -L-$C(O)OR_a$, -L-$C(S)OR_a$, -L-$C(O)$—$NR_bR_c$, -L-$C(S)$—$NR_bR_c$, -L-O—$C(O)R_a$, -L-O—$C(S)R_a$, -L-N$(R_b)$—$C(O)$—$R_a$, -L-N$(R_b)$—$C(S)$—$R_a$, -L-$S(O)_mR_a$, -L-$S(O)_mOR_a$, -L-$S(O)_mNR_bR_c$, -L-N$(R_b)$—$S(O)_m$—$R_a$, -L-N$(R_b)$—$S(O)_m$—$R_bR_c$, -L-N$(R_b)$—$C(O)OR_a$, -L-N$(R_b)$—$C(S)OR_a$, -L-O—$C_{1-6}$ alkylene-$OR_a$, -L-$C(O)$—$C_{1-6}$ alkylene-$NR_bR_c$, -L-N$(R_b)$—$C(O)$—$NR_bR_c$, -L-N$(R_b)$—$C(S)$—$NR_bR_c$, -L-O—$C(O)$—$NR_bR_c$, and -L-O—$C(S)$—$NR_bR_c$;

$R_a$ is independently selected from H, $C_{1-6}$ alkyl, $C_{2-6}$ alkenyl, $C_{2-6}$ alkynyl, $C_{1-6}$ haloalkyl, -L-$C_{3-7}$ cycloalkyl, -L-3- to 7-membered heterocyclyl, -L-$C_{6-10}$ aryl, or -L-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, -L-$C_{3-7}$ cycloalkyl, -L-3- to 7-membered heterocyclyl, -L-$C_{6-10}$ aryl, or -L-5- to 10-membered heteroaryl; or, $R_b$ and $R_c$ are taken together with the nitrogen atom to which they are attached to form 3- to 7-membered heterocyclyl;

$R_a$, $R_b$ and $R_c$ are each optionally further substituted with one or more substituents independently selected from the group consisting of $C_{1-6}$ alkyl, $C_{2-6}$ alkenyl, $C_{2-6}$ alkynyl, $C_{1-6}$ haloalkyl, -L-$C_{3-7}$ cycloalkyl, -L-3- to 7-membered heterocyclyl, -L-$C_{6-10}$ aryl, and -L-5- to 10-membered heteroaryl;

L is selected from a chemical bond, —$C_{1-6}$ alkylene-, —$C_{2-6}$ alkenylene- or —$C_{2-6}$ alkynylene-;

L' is selected from a chemical bond, —O—, —NH—, —C(O)—, —C(O)NH—, —NHC(O)—, —$C_{1-6}$ alkylene-, —$C_{2-6}$ alkenylene- or —$C_{2-6}$ alkynylene-; and m represents 0, 1 or 2.

In another aspect, the present disclosure provides a pharmaceutical composition comprising a compound disclosed herein, and optionally pharmaceutically acceptable excipients.

In another aspect, the present disclosure provides a pharmaceutical composition comprising a compound disclosed herein and pharmaceutically acceptable excipients, which further comprises other therapeutic agent(s).

In another aspect, the present disclosure provides a kit comprising a compound disclosed herein, other therapeutic agent(s), and pharmaceutically acceptable carriers, adjuvants or vehicles.

In another aspect, the present disclosure provides a use of a compound disclosed herein in the manufacture of a medicament for treating and/or preventing a CDK mediated disease.

In another aspect, the present disclosure provides a method of treating and/or preventing a CDK mediated disease in a subject, comprising administering to the subject a compound disclosed herein or a composition disclosed herein.

In another aspect, the present disclosure provides a compound disclosed herein or a composition disclosed herein, for use in treating and/or preventing a CDK mediated disease.

In a specific embodiment, the disease includes a cell proliferative disorder, including but not limited to cancers, cardiovascular disorders, infectious diseases, chronic inflammatory diseases, autoimmune disorders, and other cell proliferative disorders. More specifically, the cancers include, but are not limited to, solid tumors and hematological malignancies, such as breast cancer, neuroblastoma, malignant rhabdomyomas, well-differentiated and dedifferentiated liposarcoma, glioma, lung cancer, colorectal cancer, gastric cancer, gastrointestinal stromal tumor (GIST), hepatocellular carcinoma, prostate tumor, sarcoma, ovarian cancer, cervical cancer, pancreatic cancer, melanoma, thyroid cancer, carcinoma of bile duct, endometrial cancer, renal cancer, mesothelioma, lymphoma, leukemia, non-Hodgkin's lymphoma, mantle cell lymphoma, anaplastic large cell lymphoma, acute myeloid leukemia (AML), and multiple myeloma. The cardiovascular disorders are for instance restenosis, atherosclerosis, vascular smooth muscle proliferation and intimal hyperplasia secondary to balloon angioplasty, and other vascular disorders caused by abnormal cell proliferation. The infectious diseases include infections of fungi, protozoan parasites (such as *Plasmodium falciparum*), and DNA and RNA virus, such as herpes simplex virus (HSV) infection. The chronic inflammatory diseases are for example rheumatoid arthritis. The said other cell proliferative disorders include psoriasis (characterized by excessive proliferation of keratinocytes), glomerulonephritis, and lupus.

Other objects and advantages of the present disclosure will be apparent to those skilled in the art from the specific embodiments, examples and claims disclosed herein.

Definition

Chemical Definitions

Definitions of specific functional groups and chemical terms are described in more detail below.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

It should be understood that when described herein any of the moieties defined forth below may be substituted with a variety of substituents, and that the respective definitions are intended to include such substituted moieties within their scope as set out below. Unless otherwise stated, the term "substituted" is to be defined as set out below.

"$C_{1-6}$ alkyl" refers to a radical of a straight or branched, saturated, monovalent hydrocarbon group having from 1 to 6 carbon atoms. In some embodiments, $C_{1-4}$ alkyl is preferred. Typical $C_{1-6}$ alkyl includes methyl, ethyl, n-propyl, isopropyl, n-butyl, tert-butyl, iso-butyl, pentyl, n-hexyl, iso-hexyl, and the like. The term "$C_{1-6}$ alkyl" also includes heteroalkyl groups in which carbon atoms may be replaced by 1 to 3 atoms selected from O, S, N or substituted nitrogen atoms. The alkyl group can be substituted at any available point of attachment, for example, by from 1 to 5 substituents, 1 to 3 substituents, or 1 substituent.

"$C_{2-6}$ alkenyl" refers to a straight or branched hydrocarbon group having from 2 to 6 carbon atoms and at least one carbon-carbon double bonds, including but not limited to ethenyl, 3-buten-1-yl, 2-ethenylbutyl, 3-hexen-1-yl, and the like. In some embodiments, $C_{2-4}$ alkenyl is preferred. The term "$C_{2-6}$ alkenyl" also includes heteroalkenyl groups in which carbon atoms may be replaced by 1 to 3 atoms selected from O, S, N or substituted nitrogen atoms. The alkenyl group can be substituted at any available point of attachment, for example, by from 1 to 5 substituents, 1 to 3 substituents, or 1 substituent.

"$C_{2-6}$ alkynyl" refers to a straight or branched hydrocarbon group having from 2 to 6 carbon atoms, wherein at least one carbon-carbon triple bonds and optionally one or more unsaturated double bonds are contained. In some embodiments, $C_{2-4}$ alkynyl is preferred. Typical alkynyl includes ethynyl, propynyl, iso-propynyl, butynyl, iso-butynyl, pentynyl and hexynyl. The term "$C_{2-6}$ alkynyl" also includes heteroalkynyl groups in which carbon atoms may be replaced by 1 to 3 atoms selected from O, S, N or substituted nitrogen atoms. The alkynyl group can be substituted at any available point of attachment, for example, by from 1 to 5 substituents, 1 to 3 substituents, or 1 substituent.

"—$C_{1-6}$ alkylene-, —$C_{2-6}$ alkenylene- or —$C_{2-6}$ alkynylene-" refers to a divalent group of the "$C_{1-6}$ alkyl, $C_{2-6}$ alkenyl or $C_{2-6}$ alkynyl" as defined above.

"$C_{1-6}$ alkylene" refers to a $C_{1-6}$ alkyl group wherein another hydrogen is removed to provide a divalent radical of alkylene, and which may be substituted or unsubstituted alkylene. In some embodiments, $C_{1-4}$ alkylene is particularly preferred. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like.

"$C_{2-6}$ alkenylene" refers to a $C_{2-6}$ alkenyl group wherein another hydrogen is removed to provide a divalent radical of alkenylene, and which may be substituted or unsubstituted alkenylene. In some embodiments, $C_{2-4}$ alkenylene is particularly preferred. Exemplary unsubstituted alkenylene groups include, but are not limited to, ethenylene (—CH=CH—) and propenylene (e.g., —CH=CHCH$_2$—, —CH$_2$—CH=CH—). Exemplary substituted alkenylene groups, e.g., substituted with one or more alkyl (methyl) groups, include but are not limited to, substituted ethenylene (—C(CH$_3$)=CH—, —CH=C(CH$_3$)—), substituted propenylene (e.g., —C(CH$_3$)=CHCH$_2$—, —CH=C(CH$_3$)CH$_2$—, —CH=CHCH(CH$_3$)—, —CH=CHC(CH$_3$)$_2$—, —CH(CH$_3$)—CH=CH—, —C(CH$_3$)$_2$—CH=CH—, —CH$_2$—C(CH$_3$)=CH—, —CH$_2$—CH=C(CH$_3$)—), and the like.

"$C_{2-6}$ alkynylene" refers to a $C_{2-6}$ alkynyl group wherein another hydrogen is removed to provide a divalent radical of alkynylene, and which may be substituted or unsubstituted alkynylene. In some embodiments, $C_{2-4}$ alkynylene is particularly preferred. Exemplary alkynylene groups include, but are not limited to, ethynylene (—C≡C—), substituted or unsubstituted propynylene (—C≡CCH$_2$—), and the like.

"Halo" or "halogen" means fluorine (F), chlorine (Cl), bromine (Br) and iodine (I).

"$C_{1-6}$ haloalkyl" means the above "$C_{1-6}$ alkyl" which is substituted with one or more halogen groups. Examples include mono-, di-, and poly-halogenated, including perhalogenated, alkyl. A monohalogen substituent in the group may be an iodine, bromine, chlorine or fluorine atom; dihalogen substituents and polyhalogen substituents may be two or more identical halogen atoms or a combination of different halogens. Examples of preferred haloalkyl groups include monofluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The haloalkyl group can be substituted at any available point of attachment, for example, by 1 to 5 substituents, 1 to 3 substituents or 1 substituent.

"$C_{3-7}$ cycloalkyl" refers to a radical of a non-aromatic cyclic hydrocarbon group having from 3 to 7 ring carbon atoms and zero heteroatoms. In some embodiments, $C_{3-6}$ cycloalkyl is especially preferred, and $C_{5-6}$ cycloalkyl is more preferred. Cycloalkyl also includes ring systems wherein the cycloalkyl ring, as defined above, is fused with one or more aryl or heteroaryl groups wherein the point of attachment is on the cycloalkyl ring, and in such instances, the number of carbons continue to designate the number of carbons in the cycloalkyl ring system. Exemplary cycloalkyl groups include, but is not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), and the like.

"3- to 11-membered heterocyclyl" refers to a radical of a 3- to 11-membered non-aromatic ring system having ring carbon atoms and 1 to 5 ring heteroatoms, wherein each heteroatom is independently selected from nitrogen, oxygen, sulfur, boron, phosphorus, and silicon. In heterocyclyl groups that contain one or more nitrogen atoms, the point of attachment can be a carbon or nitrogen atom, as valency permits. In some embodiments, 3- to 9-membered heterocyclyl is preferred, which is a radical of a 3- to 9-membered non-aromatic ring system having ring carbon atoms and 1 to 5 ring heteroatoms; in some embodiments, 3- to 7-membered heterocyclyl is preferred, which is a radical of a 3- to 7-membered non-aromatic ring system having ring carbon atoms and 1 to 4 ring heteroatoms; 3- to 6-membered heterocyclyl is preferred, which is a radical of a 3- to 6-membered non-aromatic ring system having ring carbon atoms and 1 to 3 ring heteroatoms; 4- to 6-membered heterocyclyl is preferred, which is a radical of a 4- to 6-membered non-aromatic ring system having ring carbon atoms and 1 to 3 ring heteroatoms; 5- to 6-membered heterocyclyl is more preferred, which is a radical of a 5- to 6-membered non-aromatic ring system having ring carbon atoms and 1 to 3 ring heteroatoms. Heterocyclyl also includes ring systems wherein the heterocyclyl ring, as defined above, is fused with one or more cycloalkyl groups, wherein the point of attachment is on the cycloalkyl ring; or wherein the heterocyclyl ring, as defined above, is fused with one or more aryl or heteroaryl groups, wherein the point of attachment is on the heterocyclyl ring; and in such instances, the number of ring members continue to designate the number of ring members in the heterocyclyl ring system. Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thienyl. Exemplary 6-membered heterocyclyl groups containing two heteroatoms include, without limitation, piperazinyl, morpholinyl, dithianyl, dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to a $C_6$ aryl ring (also referred to herein as a 6,6-bicyclic heterocyclic ring) include, without limitation, tetrahydroquinolinyl, tetrahydroisoquinolinyl, and the like.

The 3- to 11-membered heterocyclyl also includes a spiroheterocyclic group, that is, a group in which two rings (e.g., a heterocyclyl and a carbocyclyl) share one carbon atom, wherein at least one ring is a heterocyclyl as defined above. More specifically, the spiroheterocyclyl is a spiro ring formed by two 4-membered rings, two 5-membered rings, two 6-membered rings, one 4-membered ring and one 5-membered ring, one 4-membered ring and one 6-membered ring, or one 5-membered ring and one 6-membered ring, wherein at least one ring is a 4- to 6-membered heterocyclyl as defined above, 4- to 6-membered heterocyclyl containing 1, 2 or 3 O, N or S heteroatoms is preferred, and 4- to 6-membered heterocyclyl containing 1 N heteroatom is more preferred. Specific spiroheterocyclyl groups include, but are not limited to:

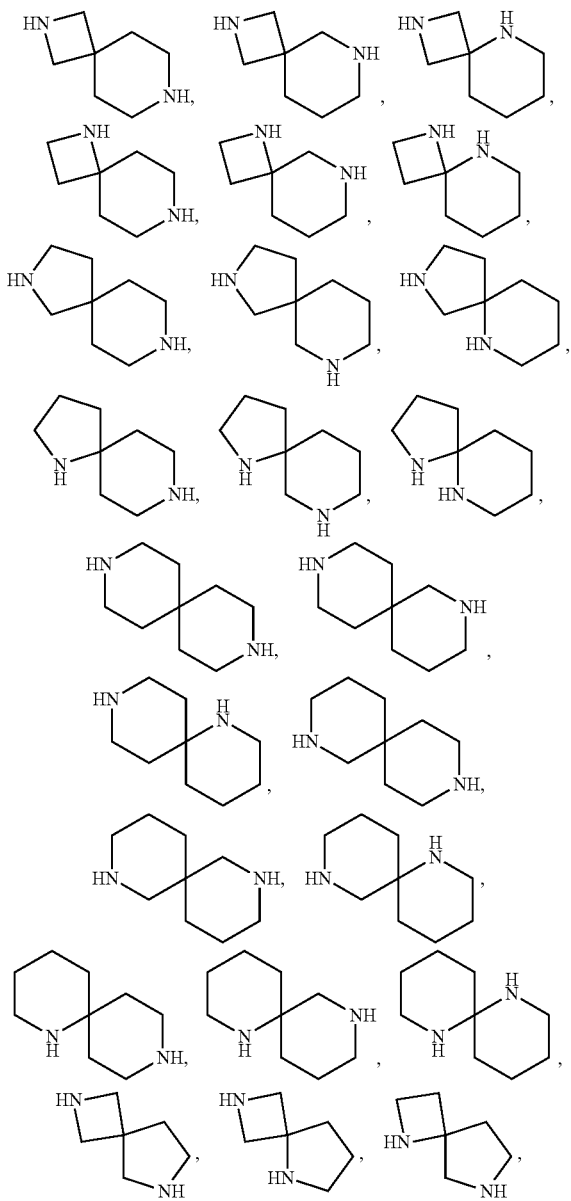

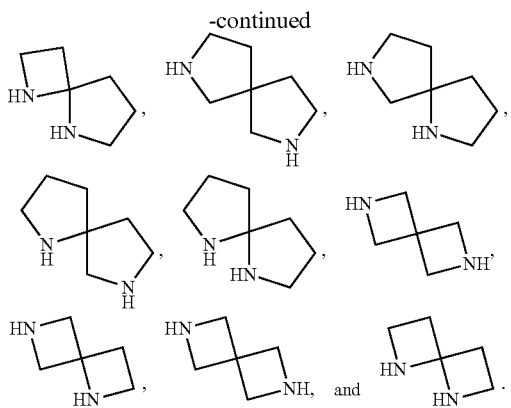

Specific examples of preferred heterocyclyl groups include: pyrrolinyl, imidazolidinyl, pyrazolidinyl, tetrahydropyranyl, dihydropyranyl, dihydrofuryl, thiazolidinyl, dihydrothiazolyl, 2,3-dihydro-benzo[1,4]dioxol, indolinyl, isoindolinyl, dihydrobenzothiophene, dihydrobenzofuranyl, isodihydrobenzopyranyl, dihydrobenzopyranyl, 1,2-dihydroisoquinoline, 1,2,3,4-tetrahydroisoquinoline, 1,2,3,4-tetrahydroquinoline, 2,3,4,4a,9,9a-hexahydro-1H-3-azafluorene, 5,6,7-trihydro-1,2,4-triazolo[3,4-a]isoquinolyl, 3,4-dihydro-2H-benzo[1,4]oxazinyl, benzo[1,4]dioxol, 2,3-dihydro-1H-1k'-benzo[d]isothiazol-6-yl, 2,3-di-benzo[1,4]dioxinyl, dihydrobenzofuran, 2-oxoazirdin-1-yl, 2-oxoazetidin-1-yl, 2-oxopyrrolidin-1-yl, 2-oxopiperidin-1-yl, 2-oxoazepan-1-yl, 2-oxoazocan-1-yl, 2-oxoazonan-1-yl, 2-oxoazecan-1-yl, aziridine, azetidine, pyrrolidinyl, piperidine, azepane, azocane, azonane, azecane, piperidinyl, piperazinyl, morpholinyl, diazaspiro[3.3]heptane, diazaspiro[3.4]octane, diazaspiro[3.5]nonane, diazaspiro[4.4]nonane, diazaspiro[4.5]decane, and diazaspiro[5.5]undecane.

"$C_{6-10}$ aryl" refers to a radical of a monocyclic or polycyclic (e.g., bicyclic) 4n+2 aromatic ring system (e.g., having 6 or 10 π electrons shared in a cyclic array) having 6-10 ring carbon atoms and zero heteroatoms. In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). Aryl also includes ring systems wherein the aryl ring, as defined above, is fused with one or more cycloalkyl, or heterocyclyl groups wherein the point of attachment is on the aryl ring, and in such instances, the number of carbon atoms continue to designate the number of carbon atoms in the aryl ring system.

"5- to 10-membered heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms, wherein each heteroatom is independently selected from nitrogen, oxygen and sulfur. In heteroaryl groups that contain one or more nitrogen atoms, the point of attachment can be a carbon or nitrogen atom, as valency permits. Heteroaryl bicyclic ring systems can include one or more heteroatoms in one or both rings. Heteroaryl further includes ring systems wherein the heteroaryl ring, as defined above, is fused with one or more cycloalkyl, or heterocyclyl groups wherein the point of attachment is on the heteroaryl ring, and in such instances, the number of ring members continue to designate the number of ring members in the heteroaryl ring system. In some embodiments, 5- to 6-membered heteroaryl is especially preferred, which is a radical of a 5-6 membered monocyclic or bicyclic 4n+2 aromatic ring system having ring carbon atoms and 1-4 ring heteroatoms. Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Specific examples of preferred heteroaryl groups include: pyrrolyl, imidazolyl, pyrazolyl, 2-pyridyl, 3-pyridyl, 4-pyridyl, pyrimidinyl, pyrazinyl, pyridazinyl, triazolyl (4H-1,2,4-triazolyl, 1H-1,2,3-triazolyl, 2H-1,2,3-triazolyl), pyranyl, 2-furyl, 3-furan and etc., 2-thienyl, 3-thienyl, oxazolyl, isoxazolyl, oxazolyl (1,2,4-oxazolyl, 1,3,4-oxazolyl, 1,2,5-oxazolyl), thiazolyl, thiadiazolyl (1,2,4-thiadiazolyl, 1,3,4-thiadiazolyl, 1,2,5-thiadiazolyl).

"carbonyl", whether used alone or in conjunction with other terms (e.g., aminocarbonyl), is represented by —C(O)—.

"Oxo" represents =O.

"Thioxo" represents =S.

Alkyl, alkenyl, alkynyl, carbocyclyl, heterocyclyl, aryl, and heteroaryl groups, as defined herein, are optionally substituted groups. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$_{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), alkyl, haloalkyl, alkenyl, alkynyl, carbocyclyl, heterocyclyl, aryl, and heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from alkyl, haloalkyl, alkenyl, alkynyl, carbocyclyl, heterocyclyl, aryl, and heteroaryl, or two R$^{aa}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{cc}$)$_2$, —P(=O)$_2$N(R$^{cc}$)$_2$, —P(=O)(NR$^{cc}$)$_2$, alkyl, haloalkyl, alkenyl, alkynyl, carbocyclyl, heterocyclyl, aryl, and heteroaryl, or two R$^{bb}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, alkyl, haloalkyl, alkenyl, alkynyl, carbocyclyl, heterocyclyl, aryl, and heteroaryl, or two R$^{cc}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{E}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, alkyl, haloalkyl, alkenyl, alkynyl, carbocyclyl, heterocyclyl, aryl, and heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from alkyl, haloalkyl, alkenyl, alkynyl, carbocyclyl, aryl, heterocyclyl, and heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, alkyl, haloalkyl, alkenyl, alkynyl, carbocyclyl, heterocyclyl, aryl and heteroaryl, or two $R^{ff}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$ X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ haloalkyl, C$_2$-C$_6$ alkenyl, C$_2$-C$_6$ alkynyl, C$_3$-C$_7$ carbocyclyl, C$_6$-C$_{10}$ aryl, C$_3$-C$_7$ heterocyclyl, C$_5$-C$_{10}$ heteroaryl; or two geminal $R^{gg}$ substituents can be joined to form =O or =S; wherein X$^-$ is a counterion.

Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R')$_2$, —P(=O)$_2$N(R$^{cc}$)$_2$, —P(=O)(NR$^{cc}$)$_2$, alkyl, haloalkyl, alkenyl, alkynyl, carbocyclyl, heterocyclyl, aryl, and heteroaryl, or two $R^{cc}$ groups attached to a nitrogen atom are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

Other Definitions

The term "cancer" includes, but is not limited to, the following cancers: breast, ovary, cervix, prostate, testis, esophagus, stomach, skin, lung, bone, colon, pancreas, thyroid, biliary tract, buccal cavity and pharynx (mouth), lips, tongue, mouth, pharynx, small intestine, colorectal, large intestine, rectum, cancer of brain and central nervous system, glioblastoma, neuroblastoma, keratoacanthoma, epidermoid carcinoma, large cell carcinoma, adenocarcinoma, adenoma, follicular carcinoma, undifferentiated carcinoma, papillary carcinoma, seminoma, melanoma, sarcoma, bladder cancer, liver cancer, kidney cancer, bone marrow disorder, lymphatic disorder, Hodgkin's disease, hairy cell carcinoma and leukemia.

The term "treating/treatment" as used herein relates to reversing, alleviating, inhibiting the progression or prophylaxis of a disorder or condition to which the term applies, or one or more symptoms of such disorder or condition. The noun "treating/treatment" as used herein relates to the action of treat, which is a verb, and the latter is as just defined.

The term "pharmaceutically acceptable salt" as used herein denotes those carboxylate salts, and amino acid addition salts of the compounds disclosed herein, which are, within the scope of sound medical judgment, suitable for use in contact with the patient's tissue without undue toxicity, irritation, allergic response and the like, and are commensurate with a reasonable benefit/risk ratio, and are effective for their intended use, including, if possible, the zwitterionic form of the compounds disclosed herein.

The term "salt" denotes relatively non-toxic, inorganic and organic acid addition salts of the compounds disclosed herein. These salts can be prepared in situ during the final isolation and purification of the compound, or by isolating salts produced by separately reacting the purified compound in the free base form with a suitable organic or inorganic acid. As long as the compounds disclosed herein are basic compounds, they are capable of forming a plurality of different salts with various inorganic and organic acids. Although such salts must be pharmaceutically acceptable for administration to animals, it is often happened in practice that the pharmaceutically unacceptable salts of the basic compounds are first isolated from the reaction mixture, and then they are simply treated with an alkaline agent to convert to the free base compound, followed by the conversion of the free base to pharmaceutically acceptable acid addition salts. The acid addition salts of the basic compound are prepared by contacting the free base form with a sufficient amount of the desired acid in a conventional manner to form the salts. The free base can be regenerated by contacting the salt form with a base in a conventional manner and then isolating the free base. The free base forms differ somewhat in their physical properties from their respective salt forms, such as solubility in polar solvents, but for the purposes of the present invention, the salts are also equivalent to their respective free bases.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound disclosed herein may vary depending on such factors as the desired biological endpoint, the pharmacokinetics of the compound, the disease being treated, the mode of administration, and the age, health, and condition of the subject. An effective amount encompasses therapeutically effective amount and prophylactically effective amount.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prophylaxis of the disease, disorder or condition. The term "prophylactically effective amount" can encompass an amount that improves overall prophylaxis or enhances the prophylactic efficacy of another prophylactic agent.

"Combination" and related terms mean the simultaneous or sequential administration of a compound disclosed herein and one or more other therapeutic agents. For example, the compound disclosed herein may be administered simultaneously or sequentially with other therapeutic agents in separate unit dosage forms, or together with one or more other therapeutic agents in a single unit dosage form.

DETAILED DESCRIPTION OF THE EMBODIMENTS

As used herein, the term "compound disclosed herein" refers to the following compound of formula (I), or a pharmaceutically acceptable salt, enantiomer, diastereomer, racemate, or mixture thereof.

Compounds are generally described herein using standard nomenclature. For compounds having an asymmetric center, it should be understood, unless otherwise stated, that all optical isomers and mixtures thereof are included. Furthermore, all isomer compounds and carbon-carbon double bonds included in the present disclosure may occur in the form of Z and E unless otherwise specified. Compounds which exist in different tautomeric forms, one of which is not limited to any particular tautomer, but is intended to cover all tautomeric forms. General formula is used for certain compounds, including descriptions and variables. Unless otherwise specified, each variable in such a formula is defined independently of any other variable and multiple variables that independently define any one of the variables in each occurrence.

In one embodiment, the present disclosure refers to a compound of formula (I), or a pharmaceutically acceptable salt, enantiomer, diastereomer, racemate, or mixture thereof:

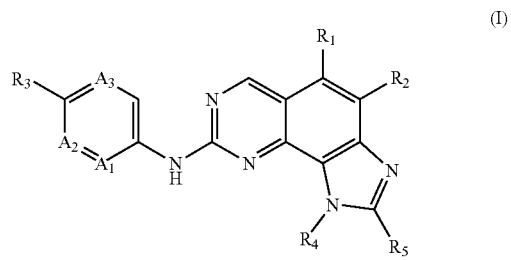

wherein:

$A_1$ is selected from $CR_3$ or N;

$A_2$ is selected from $CR_3$ or N;

$A_3$ is selected from $CR_3$ or N;

$R_1$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted with oxo or thioxo;

$R_2$ is selected from H, halogen, —CN, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted with oxo or thioxo;

$R_3$ is selected from H, halogen, —CN, —$NO_2$, -L-$OR_a$, -L-$SR_a$, -L-$NR_bR_c$, -L-C(O)$R_a$, -L-C(O)$OR_a$, -L-C(O)$NR_bR_c$, -L-S(O)$_mR_a$, -L-S(O)$_mOR_a$, -L-S(O)$_mNR_bR_c$, —O—$C_{1-6}$ alkylene-$R_6$, $C_{1-6}$ alkyl, $C_{1-6}$ haloalkyl, -L'-$C_{3-7}$ cycloalkyl, -L'-3- to 11-membered heterocyclyl, -L'-$C_{6-10}$ aryl, or -L'-5- to 10-membered heteroaryl, each of which is optionally substituted with 1, 2, 3, 4 or 5 $R_6$ groups;

$R_4$ is selected from —C(O)$R_a$, —C(O)$OR_a$, —C(O)$NR_bR_c$, $C_{1-6}$ alkyl, $C_{1-6}$ haloalkyl, $C_{3-7}$ cycloalkyl, or 3- to 7-membered heterocyclyl;

$R_5$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted with oxo or thioxo;

$R_6$ is selected from H, —$NH_2$, —$NHC_{1-6}$ alkyl, —$N(C_{1-6}$ alkyl)$_2$, $C_{1-6}$ alkyl, $C_{1-6}$ haloalkyl, —$C_{1-6}$ alkylene-$OR_a$, -L-$C_{3-7}$ cycloalkyl, -L-3- to 7-membered heterocyclyl, -L-$C_{6-10}$ aryl, or -L-5- to 10-membered heteroaryl;

or two $R_6$ groups on the same carbon atom are taken together to form oxo or thioxo;

wherein:

$R_4$ is optionally substituted with 1, 2 or 3 R' groups, wherein R' is independently selected from H, halogen, —CN, —NO$_2$, —OR$_a$, —SR$_a$, —NR$_b$R$_c$, —C(O)OR$_a$, —C(O)NR$_b$R$_c$, C$_{1-6}$ alkyl, C$_{1-6}$ haloalkyl, C$_{3-7}$ cycloalkyl, 3- to 7-membered heterocyclyl, C$_{6-10}$ aryl, or 5- to 10-membered heteroaryl;

each of R$_3$, R$_5$ and R$_6$ is optionally substituted with 1, 2 or 3 R″ groups, wherein R″ is independently selected from H, —OH, halogen, —NO$_2$, carbonyl, -L-CN, -L-OR$_a$, -L-SR$_a$, -L-NR$_b$R$_c$, -L-C(O)R$_a$, -L-C(S)R$_a$, -L-C(O)OR$_a$, -L-C(S)OR$_a$, -L-C(O)—NR$_b$R$_c$, -L-C(S)—NR$_b$R$_c$, -L-O—C(O)R$_a$, -L-O—C(S)R$_a$, -L-N(R$_b$)—C(O)—R$_a$, -L-N(R$_b$)—C(S)—R$_a$, -L-S(O)$_m$R$_a$, -L-S(O)$_m$OR$_a$, -L-S(O)$_m$NR$_b$R$_c$, -L-N(R$_b$)—S(O)$_m$—R$_a$, -L-N(R$_b$)—S(O)$_m$—NR$_b$R$_c$, -L-N(R$_b$)—C(O)OR$_a$, -L-N(R$_b$)—C(S)OR$_a$, -L-O—C$_{1-6}$ alkylene-OR$_a$, -L-C(O)—C$_{1-6}$ alkylene-NR$_b$R$_c$, -L-N(R$_b$)—C(O)—NR$_b$R$_c$, -L-N(R$_b$)—C(S)—NR$_b$R$_c$, -L-O—C(O)—NR$_b$R$_c$, -L-O—C(S)—NR$_b$R$_c$, C$_{1-6}$ alkyl, C$_{1-6}$ haloalkyl, C$_{2-6}$ alkenyl, C$_{2-6}$ alkynyl, -L-C$_{3-7}$ cycloalkyl, -L-3- to 7-membered heterocyclyl, -L-C$_{6-10}$ aryl, or -L-5- to 10-membered heteroaryl; wherein the said C$_{1-6}$ alkyl, C$_{1-6}$ haloalkyl, C$_{2-6}$ alkenyl, C$_{2-6}$ alkynyl, -L-C$_{3-7}$ cycloalkyl, -L-3- to 7-membered heterocyclyl, -L-C$_{6-10}$ aryl, or -L-5- to 10-membered heteroaryl is each optionally further substituted with one or more substituents independently selected from the group consisting of -L-CN, —NO$_2$, carbonyl, -L-OR$_a$, -L-SR$_a$, -L-NR$_b$R$_c$, -L-C(O)R$_a$, -L-C(S)R$_a$, -L-C(O)OR$_a$, -L-C(S)OR$_a$, -L-C(O)—NR$_b$R$_c$, -L-C(S)—NR$_b$R$_c$, -L-O—C(O)R$_a$, -L-O—C(S)R$_a$, -L-N(R$_b$)—C(O)—R$_a$, -L-N(R$_b$)—C(S)—R$_a$, -L-S(O)$_m$R$_a$, -L-S(O)$_m$OR$_a$, -L-S(O)$_m$NR$_b$R$_c$, -L-N(R$_b$)—S(O)$_m$—R$_a$, -L-N(R$_b$)—S(O)$_m$—R$_b$R$_c$, -L-N(R$_b$)—C(O)OR$_a$, -L-N(R$_b$)—C(S)OR$_a$, -L-O—C$_{1-6}$ alkylene-OR$_a$, -L-C(O)—C$_{1-6}$ alkylene-NR$_b$R$_c$, -L-N(R$_b$)—C(O)—NR$_b$R$_c$, -L-N(R$_b$)—C(S)—NR$_b$R$_c$, -L-O—C(O)—NR$_b$R$_c$, and -L-O—C(S)—NR$_b$R$_c$;

R$_a$ is independently selected from H, C$_{1-6}$ alkyl, C$_{2-6}$ alkenyl, C$_{2-6}$ alkynyl, C$_{1-6}$ haloalkyl, -L-C$_{3-7}$ cycloalkyl, -L-3- to 7-membered heterocyclyl, -L-C$_{6-10}$ aryl, or -L-5- to 10-membered heteroaryl;

R$_b$ and R$_c$ are independently selected from H, C$_{1-6}$ alkyl, C$_{2-6}$ alkenyl, C$_{2-6}$ alkynyl, C$_{1-6}$ haloalkyl, -L-C$_{3-7}$ cycloalkyl, -L-3- to 7-membered heterocyclyl, -L-C$_{6-10}$ aryl, or -L-5- to 10-membered heteroaryl; or, R$_b$ and R$_c$ are taken together with the nitrogen atom to which they are attached to form 3- to 7-membered heterocyclyl;

R$_a$, R$_b$ and R$_c$ are each optionally further substituted with one or more substituents independently selected from the group consisting of C$_{1-6}$ alkyl, C$_{2-6}$ alkenyl, C$_{2-6}$ alkynyl, C$_{1-6}$ haloalkyl, -L-C$_{3-7}$ cycloalkyl, -L-3- to 7-membered heterocyclyl, -L-C$_{6-10}$ aryl, and -L-5- to 10-membered heteroaryl;

L is selected from a chemical bond, —C$_{1-6}$ alkylene-, —C$_{2-6}$ alkenylene- or —C$_{2-6}$ alkynylene-;

L' is selected from a chemical bond, —O—, —NH—, —C(O)—, —C(O)NH—, —NHC(O)—, —C$_{1-6}$ alkylene-, —C$_{2-6}$ alkenylene- or —C$_{2-6}$ alkynylene-; and m represents 0, 1 or 2.

A$_1$, A$_2$ and A$_3$

In a specific embodiment, A$_1$ is CR$_3$; in another specific embodiment, A$_1$ is CH; in another specific embodiment, A$_1$ is N.

In a specific embodiment, A$_2$ is CR$_3$; in another specific embodiment, A$_2$ is CH; in another specific embodiment, A$_2$ is N.

In a specific embodiment, A$_3$ is CR$_3$; in another specific embodiment, A$_3$ is CH; in another specific embodiment, A$_3$ is N.

In a specific embodiment, A$_1$ is N, A$_2$ is CR$_3$ and A$_3$ is CR$_3$; in another specific embodiment, A$_1$ is CR$_3$, A$_2$ is CR$_3$ and A$_3$ is CR$_3$.

R$_1$

In a specific embodiment, R$_1$ is H; in another specific embodiment, R$_1$ is halogen; in another specific embodiment, R$_1$ is —CN; in another specific embodiment, R$_1$ is —OR$_a$; in another specific embodiment, R is —SR$_a$; in another specific embodiment, R$_1$ is —NR$_b$R$_c$; in another specific embodiment, R$_1$ is —C(O)R$_a$; in another specific embodiment, R$_1$ is —C(O)OR$_a$; in another specific embodiment, R$_1$ is —C(O)NR$_b$R$_c$; in another specific embodiment, R$_1$ is C$_{1-6}$ alkyl; in another specific embodiment, R$_1$ is C$_{1-6}$ haloalkyl; in another specific embodiment, R$_1$ is C$_{3-7}$ cycloalkyl; in another specific embodiment, R$_1$ is 3- to 7-membered heterocyclyl; in another specific embodiment, R$_1$ is C$_{6-10}$ aryl; in another specific embodiment, R$_1$ is 5- to 10-membered heteroaryl.

R$_2$

In a specific embodiment, R$_2$ is H; in another specific embodiment, R$_2$ is halogen; in another specific embodiment, R$_2$ is —CN; in another specific embodiment, R$_2$ is C$_{1-6}$ alkyl; in another specific embodiment, R$_2$ is C$_{1-6}$ haloalkyl; in another specific embodiment, R$_2$ is C$_{3-7}$ cycloalkyl; in another specific embodiment, R$_2$ is 3- to 7-membered heterocyclyl; in another specific embodiment, R$_2$ is C$_{6-10}$ aryl; in another specific embodiment, R$_2$ is 5- to 10-membered heteroaryl.

In a specific embodiment, R$_2$ is H, halogen, C$_{1-6}$ alkyl or C$_{1-6}$ haloalkyl; in another specific embodiment, R$_2$ is H, halogen or C$_{1-6}$ alkyl.

R$_3$

In a specific embodiment, R$_3$ is H; in another specific embodiment, R$_3$ is halogen; in another specific embodiment, R$_3$ is —CN; in another specific embodiment, R$_3$ is —NO$_2$; in another specific embodiment, R$_3$ is -L-OR$_a$; in another specific embodiment, R$_3$ is -L-SR$_a$; in another specific embodiment, R$_3$ is -L-NR$_b$R$_c$; in another specific embodiment, R$_3$ is -L-C(O)R$_a$; in another specific embodiment, R$_3$ is -L-C(O)OR$_a$; in another specific embodiment, R$_3$ is -L-C(O)NR$_b$R$_c$; in another specific embodiment, R$_3$ is -L-S(O)$_m$R$_a$; in another specific embodiment, R$_3$ is -L-S(O)$_m$OR$_a$; in another specific embodiment, R$_3$ is -L-S(O)$_m$NR$_b$R$_c$; in another specific embodiment, R$_3$ is —O—C$_{1-6}$ alkylene-R$_6$; in another specific embodiment, R$_3$ is C$_{1-6}$ alkyl; in another specific embodiment, R$_3$ is C$_{1-6}$ haloalkyl; in another specific embodiment, R$_3$ is -L'-C$_{3-7}$ cycloalkyl; in another specific embodiment, R$_3$ is -L'-3- to 11-membered heterocyclyl; in another specific embodiment, R$_3$ is -L'-3- to 9-membered heterocyclyl; in another specific embodiment, R$_3$ is -L'-C$_{6-10}$ aryl; in another specific embodiment, R$_3$ is -L'-5- to 10-membered heteroaryl.

In the specific embodiments of R$_3$ as mentioned above, each of the groups is optionally substituted with 1, 2, 3, 4 or 5 R$_6$ groups. In a specific embodiment, each of the groups is optionally substituted with 1 R$_6$ group; in another specific embodiment, each of the groups is optionally substituted with 2 R$_6$ groups; in another specific embodiment, each of the groups is optionally substituted with 3 R$_6$ groups; in another specific embodiment, each of the groups is optionally substituted with 4 R$_6$ groups; in another specific embodiment, each of the groups is optionally substituted with 5 R$_6$ groups.

In a more specific embodiment, $R_3$ is selected from -L'-3- to 11-membered heterocyclyl, wherein the said 3- to 11-membered heterocyclyl is selected from:

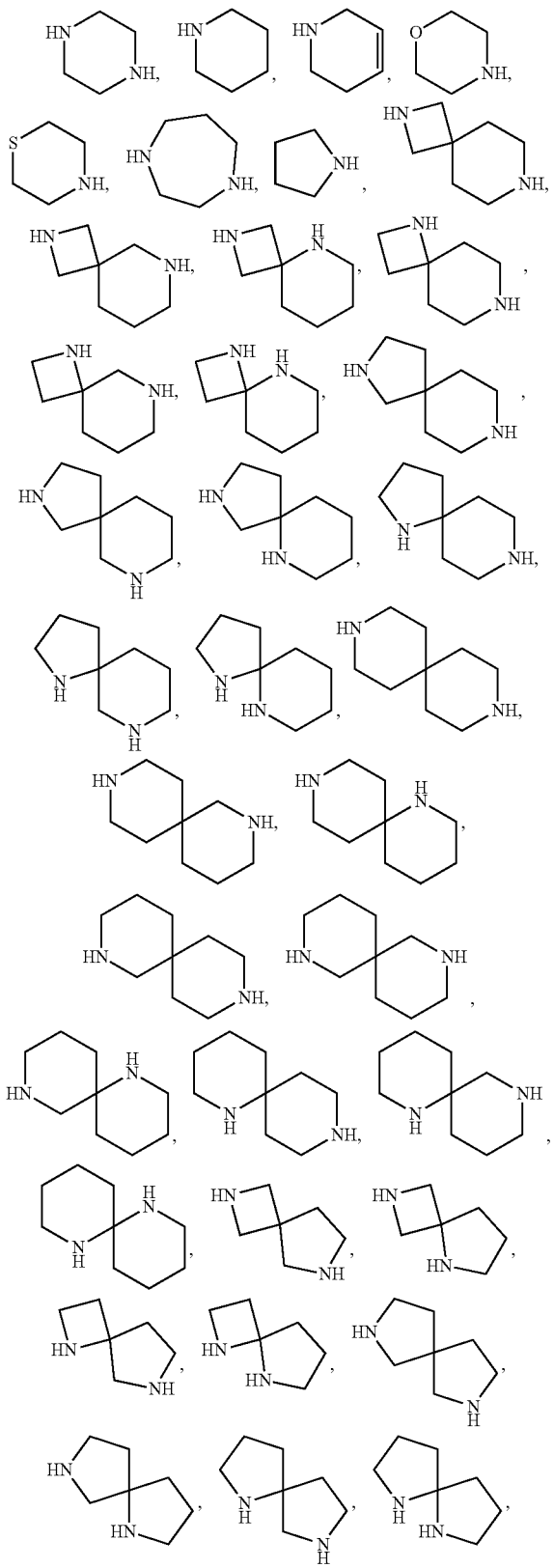

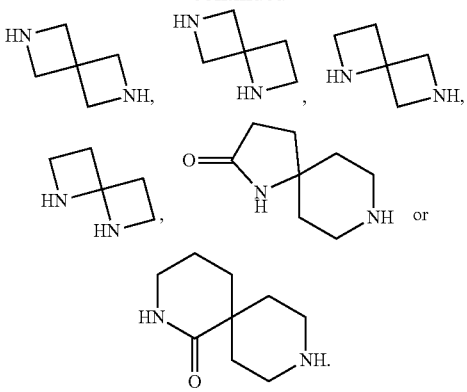

In another specific embodiment, $R_3$ is independently selected from H, halogen, —CN, —NO$_2$, $C_{1-6}$ alkyl, $C_{1-6}$ haloalkyl, or -L'-3- to 11-membered heterocyclyl (preferably, 3- to 11-membered heterocyclyl) which is optionally substituted with 1, 2, 3 or 4 $R_6$ groups; in another specific embodiment, $R_3$ is independently selected from H, $C_{1-6}$ alkyl, $C_{1-6}$ haloalkyl, or -L'-3- to 11-membered heterocyclyl (preferably, 3- to 11-membered heterocyclyl) which is optionally substituted with 1, 2, 3 or 4 $R_6$ groups; in another specific embodiment, $R_3$ is independently selected from H, halogen, —CN, —NO$_2$, $C_{1-6}$ alkyl, $C_{1-6}$ haloalkyl, or -L'-5- to 6-membered heterocyclyl (preferably, 5- to 6-membered heterocyclyl) which is optionally substituted with 1, 2, 3 or 4 $R_6$ groups; in another specific embodiment, $R_3$ is independently selected from H, $C_{1-6}$ alkyl, $C_{1-6}$ haloalkyl, or -L'-5- to 6-membered heterocyclyl (preferably, 5- to 6-membered heterocyclyl) which is optionally substituted with 1, 2, 3 or 4 $R_6$ groups.

In another specific embodiment, $R_3$ is independently selected from H, halogen, —CN, —NO$_2$, $C_{1-6}$ alkyl, $C_{1-6}$ haloalkyl, or is independently selected from

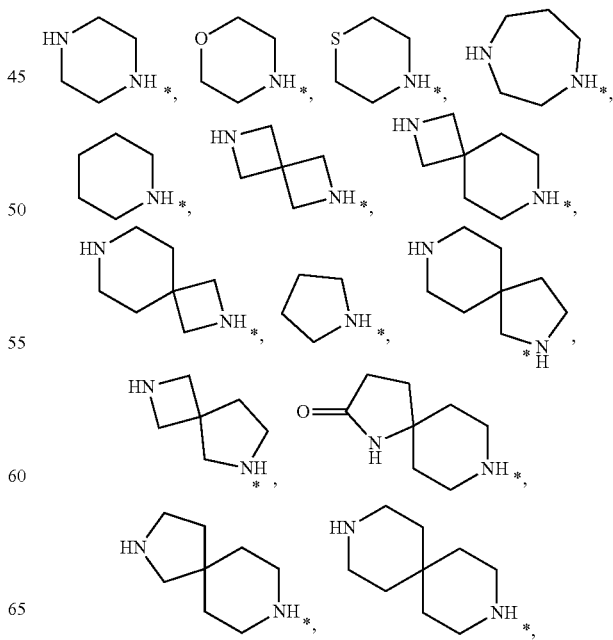

-continued

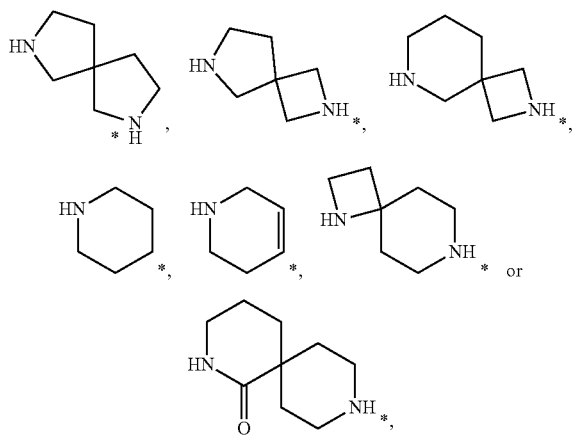

any of which is optionally substituted with 1, 2, 3 or 4 $R_6$ groups; in another specific embodiment, $R_3$ is independently selected from H, $C_{1-6}$ alkyl, $C_{1-6}$ haloalkyl, or is independently selected from

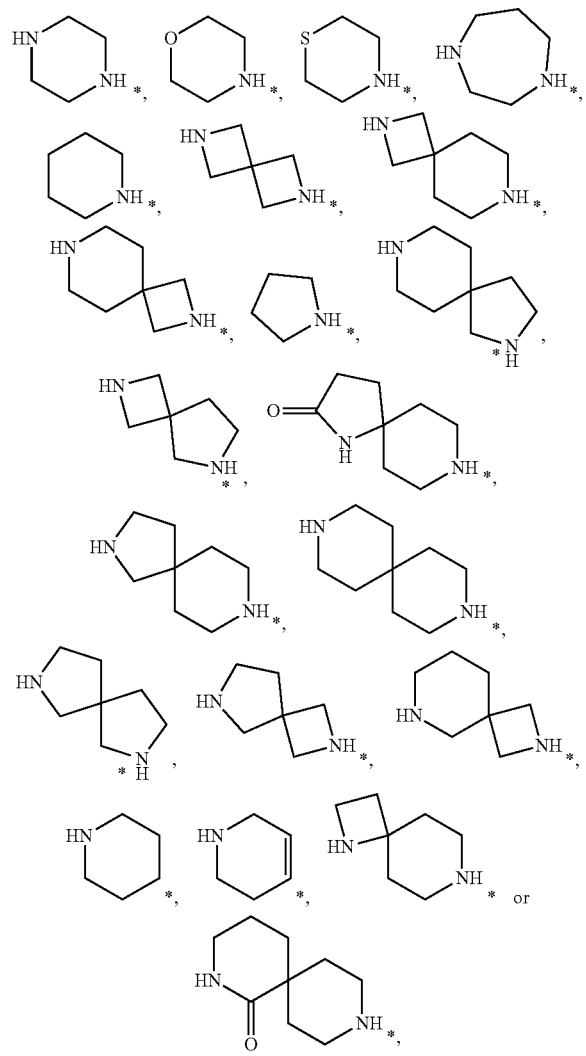

any of which is optionally substituted with 1, 2, 3 or 4 $R_6$ groups; in another specific embodiment, $R_3$ is selected from H, halogen, —CN, —$NO_2$, $C_{1-6}$ alkyl, $C_{1-6}$ haloalkyl, or is independently selected from

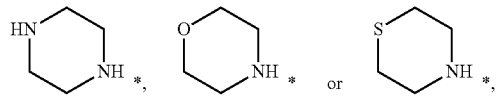 [SMILES: C1CNCCN1 ; C1COCCN1 ; C1CSCCN1]

any of which is optionally substituted with 1, 2, 3 or 4 $R_6$ groups; in another specific embodiment, $R_3$ is independently selected from H, $C_{1-6}$ alkyl, $C_{1-6}$ haloalkyl, or is independently selected from

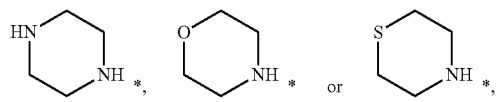 [SMILES: C1CNCCN1 ; C1COCCN1 ; C1CSCCN1]

any of which is optionally substituted with 1, 2, 3 or 4 $R_6$ groups.

In another specific embodiment, $R_3$ is independently selected from -L'-3- to 11-membered heterocyclyl (preferably, 3- to 11-membered heterocyclyl) which is optionally substituted with 1, 2, 3 or 4 $R_6$ groups; in another specific embodiment, $R_3$ is independently selected from -L'-5- to 6-membered heterocyclyl (preferably, 5- to 6-membered heterocyclyl) which is optionally substituted with 1, 2, 3 or 4 $R_6$ groups.

In another specific embodiment, $R_3$ is independently selected from

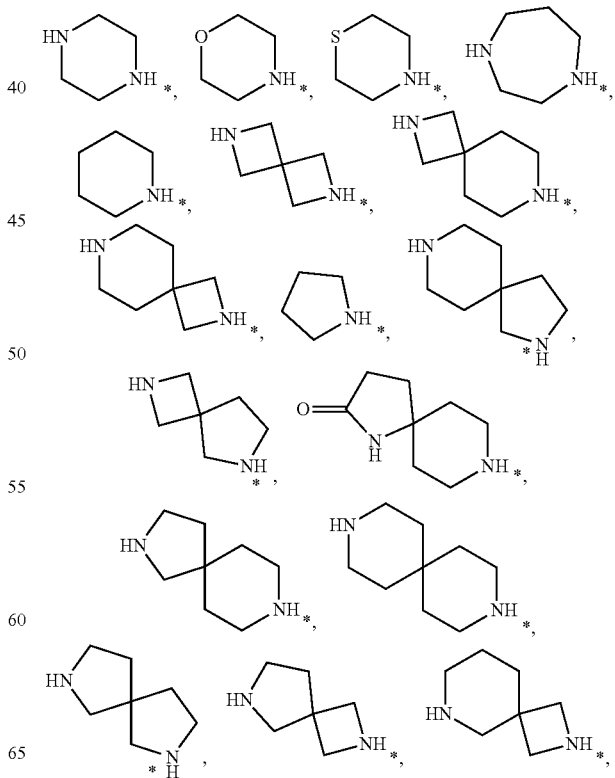

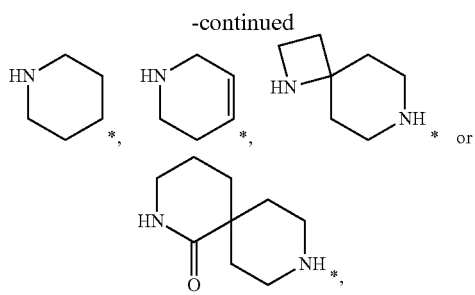

any of which is optionally substituted with 1, 2, 3 or 4 $R_6$ groups; in another specific embodiment, $R_3$ is selected from

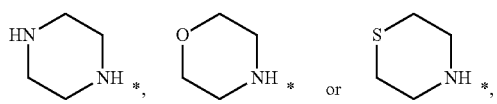 [SMILES: C1CNCCN1 ; C1COCCN1 ; C1CSCCN1]

any of which is optionally substituted with 1, 2 or 3 $R_6$ groups; in another specific embodiment, $R_3$ is selected from —O—$C_{1-6}$ alkylene-$R_6$, -L'-3- to 11-membered heterocyclyl or —C(O)$NR_bR_c$, each of which is optionally substituted with 1 or 2 $R_6$ groups.

In a specific embodiment, when $A_2$ or $A_3$ is $CR_3$, then $R_3$ is $R_3'$. In another specific embodiment, $R_3'$ is selected from H, halogen, $C_{1-6}$ alkyl or $C_{1-6}$ haloalkyl, and $R_3$ is as defined above; in another specific embodiment, $R_3'$ is selected from H, $C_{1-6}$ alkyl or $C_{1-6}$ haloalkyl, and $R_3$ is as defined above.

$R_4$

In a specific embodiment, $R_4$ is —C(O)$R_a$; in another specific embodiment, $R_4$ is —C(O)$OR_a$; in another specific embodiment, $R_4$ is —C(O)$NR_bR_c$; in another specific embodiment, $R_4$ is $C_{1-6}$ alkyl; in another specific embodiment, $R_4$ is $C_{1-6}$ haloalkyl; in another specific embodiment, $R_4$ is $C_{3-7}$ cycloalkyl; in another specific embodiment, $R_4$ is 3- to 7-membered heterocyclyl.

In another specific embodiment, $R_4$ is selected from $C_{1-6}$ alkyl, $C_{1-6}$ haloalkyl, $C_{3-7}$ cycloalkyl, or 3- to 7-membered heterocyclyl; in another specific embodiment, $R_4$ is selected from $C_{1-6}$ alkyl, $C_{1-6}$ haloalkyl or $C_{3-7}$ cycloalkyl; in another specific embodiment, $R_4$ is selected from $C_{1-6}$ alkyl or $C_{3-7}$ cycloalkyl; in another specific embodiment, $R_4$ is isopropyl; in another specific embodiment, $R_4$ is cyclopentyl; in another specific embodiment, $R_4$ is cyclopropyl.

$R_5$

In a specific embodiment, $R_5$ is H; in another specific embodiment, $R_5$ is halogen; in another specific embodiment, $R_5$ is —CN; in another specific embodiment, $R_5$ is —$OR_a$; in another specific embodiment, $R_5$ is —$SR_a$; in another specific embodiment, $R_5$ is —$NR_bR_c$; in another specific embodiment, $R_5$ is —C(O)$R_a$; in another specific embodiment, $R_5$ is —C(O)$OR_a$; in another specific embodiment, $R_5$ is —C(O)$NR_bR_c$; in another specific embodiment, $R_5$ is $C_{1-6}$ alkyl; in another specific embodiment, $R_5$ is $C_{1-6}$ haloalkyl; in another specific embodiment, $R_5$ is $C_{3-7}$ cycloalkyl; in another specific embodiment, $R_5$ is 3- to 7-membered heterocyclyl; in another specific embodiment, $R_5$ is $C_{6-10}$ aryl; in another specific embodiment, $R_5$ is 5- to 10-membered heteroaryl.

$R_6$

In a specific embodiment, $R_6$ is H; in another specific embodiment, $R_6$ is —$NH_2$; in another specific embodiment, $R_6$ is —$NHC_{1-6}$ alkyl; in another specific embodiment, $R_6$ is —N($C_{1-6}$ alkyl)$_2$; in another specific embodiment, $R_6$ is $C_{1-6}$ alkyl; in another specific embodiment, $R_6$ is $C_{1-6}$ haloalkyl; in another specific embodiment, $R_6$ is —$C_{1-6}$ alkylene-$OR_a$; in another specific embodiment, $R_6$ is -L-$C_{3-7}$ cycloalkyl; in another specific embodiment, $R_6$ is -L-3- to 7-membered heterocyclyl; in another specific embodiment, $R_6$ is -L-$C_{6-10}$ aryl; in another specific embodiment, $R_6$ is -L-5- to 10-membered heteroaryl; in another specific embodiment, two $R_6$ on the same carbon atom are taken together to form oxo. In another specific embodiment, two $R_6$ on the same carbon atom are taken together to form thioxo.

In a specific embodiment, $R_6$ is independently selected from H, —$NH_2$, —$NHC_{1-6}$ alkyl, —N($C_{1-6}$ alkyl)$_2$, $C_{1-6}$ alkyl, $C_{1-6}$ haloalkyl or —$C_{0-6}$ alkylene-$OR_a$; in another specific embodiment, $R_6$ is independently selected from H, —$NH_2$, —$NHC_{1-6}$ alkyl, —N($C_{1-6}$ alkyl)$_2$, $C_{1-6}$ alkyl or —$C_{0-6}$ alkylene-$OR_a$; in another specific embodiment, $R_6$ is independently selected from H, —$NH_2$, —$NHC_{1-6}$ alkyl, —N($C_{1-6}$ alkyl)$_2$, $C_{1-6}$ alkyl or $C_{1-6}$ haloalkyl; in another specific embodiment, $R_6$ is independently selected from H, $C_{1-6}$ alkyl, $C_{1-6}$ haloalkyl or —$C_{0-6}$ alkylene-$OR_a$; in another specific embodiment, $R_6$ is independently selected from H, $C_{1-6}$ alkyl or $C_{1-6}$ haloalkyl.

L

In a specific embodiment, L is a chemical bond; in another specific embodiment, L is —$C_{1-6}$ alkylene-; in another specific embodiment, L is —$C_{2-6}$ alkenylene-; in another specific embodiment, L is —$C_{2-6}$ alkynylene-.

L'

In a specific embodiment, L' is a chemical bond; in another specific embodiment, L' is —O—; in another specific embodiment, L' is —NH—; in another specific embodiment, L' is —C(O)—; in another specific embodiment, L' is —C(O)NH—; in another specific embodiment, L' is —NHC(O)—; in another specific embodiment, L' is —$C_{1-6}$ alkylene-; in another specific embodiment, L' is —$C_{2-6}$ alkenylene-; in another specific embodiment, L' is —$C_{2-6}$ alkynylene-.

m

In a specific embodiment, m is 0; in another specific embodiment, m is 1; in another specific embodiment, m is 2.

Any technical solution in any one of the above specific embodiments, or any combination thereof, may be combined with any technical solution in other specific embodiments or any combination thereof. For example, any technical solution of $A_1$ or any combination thereof may be combined with any technical solution of $A_2$, $A_3$, $R_1$-$R_6$, R', R", $R_a$, $R_b$, $R_c$, L, L' and m or any combination thereof. The present disclosure is intended to include all combination of such technical solutions, which are not exhaustively listed here to save space.

In a specific embodiment, the present disclosure refers to a compound of formula (I), or a pharmaceutically acceptable salt, enantiomer, diastereomer, racemate, or mixture thereof:

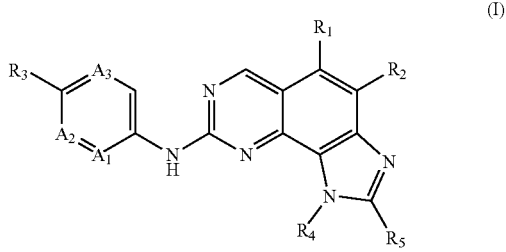

wherein:

A₁ is selected from CR₃ or N; preferably, A₁ is CR₃; preferably, A₁ is N;

A₂ is CR₃;

A₃ is CR₃;

R₁ is selected from H, $C_{1-6}$ alkyl or $C_{1-6}$ haloalkyl; preferably, R₁ is selected from H or $C_{1-6}$ alkyl; preferably, R₁ is H;

R₂ is selected from H, halogen, $C_{1-6}$ alkyl or $C_{1-6}$ haloalkyl; preferably, R₂ is selected from H, halogen or $C_{1-6}$ alkyl; preferably, R₂ is selected from halogen or $C_{1-6}$ alkyl; preferably, R₂ is H;

R₃ is independently selected from H, halogen, —CN, —NO₂, $C_{1-6}$ alkyl, $C_{1-6}$ haloalkyl, or -L'-3- to 11-membered heterocyclyl (preferably, 3- to 11-membered heterocyclyl) which is optionally substituted with 1, 2, 3 or 4 R₆ groups; preferably, R₃ is independently selected from H, $C_{1-6}$ alkyl, $C_{1-6}$ haloalkyl, or -L'-3- to 11-membered heterocyclyl (preferably, 3- to 11-membered heterocyclyl) which is optionally substituted with 1, 2, 3 or 4 R₆ groups; preferably, R₃ is independently selected from H, halogen, —CN, —NO₂, $C_{1-6}$ alkyl, $C_{1-6}$ haloalkyl, or -L'-5- to 6-membered heterocyclyl (preferably, 5- to 6-membered heterocyclyl) which is optionally substituted with 1, 2, 3 or 4 R₆ groups; preferably, R₃ is independently selected from H, $C_{1-6}$ alkyl, $C_{1-6}$ haloalkyl, or -L'-5- to 6-membered heterocyclyl (preferably, 5- to 6-membered heterocyclyl) which is optionally substituted with 1, 2, 3 or 4 R₆ groups; preferably, R₃ is independently selected from H, halogen, —CN, —NO₂, $C_{1-6}$ alkyl or $C_{1-6}$ haloalkyl, or is independently selected from

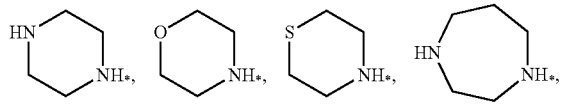
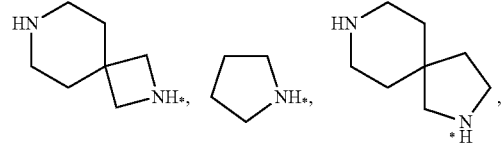
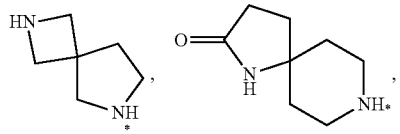
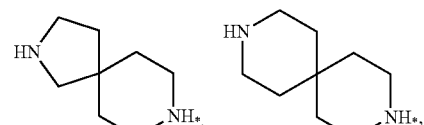
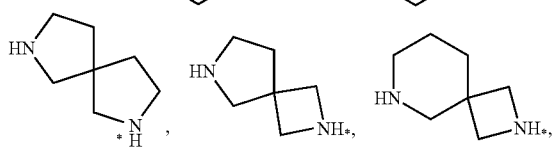
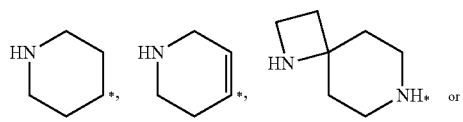
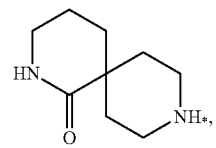

any of which is optionally substituted with 1, 2, 3 or 4 R₆ groups;

preferably, R₃ is independently selected from H, $C_{1-6}$ alkyl, $C_{1-6}$ haloalkyl, or is independently selected from

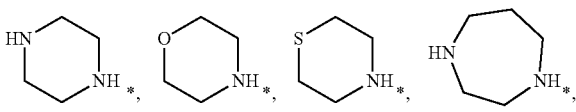
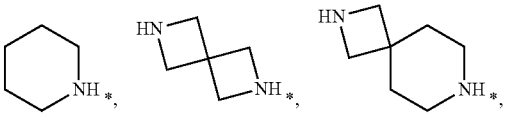
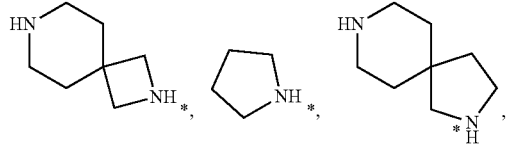
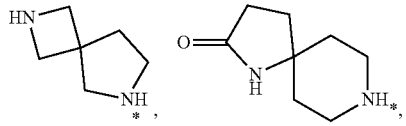
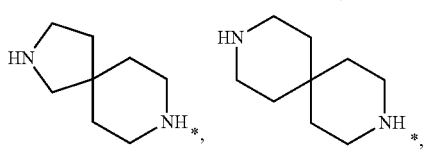
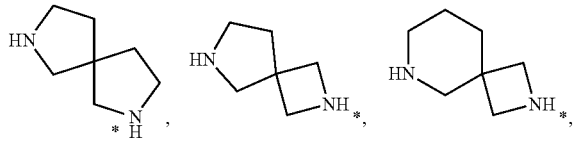
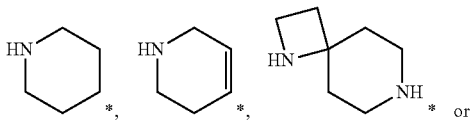
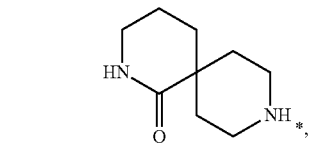

any of which is optionally substituted with 1, 2, 3 or 4 R₆ groups;

preferably, R₃ is independently selected from H, halogen, —CN, —NO₂, $C_{1-6}$ alkyl, $C_{1-6}$ haloalkyl, or is independently selected from

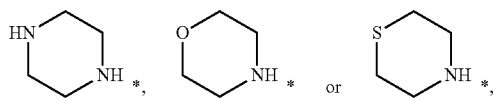

any of which is optionally substituted with 1, 2, 3 or 4 $R_6$ groups;

preferably, $R_3$ is independently selected from H, $C_{1-6}$ alkyl, $C_{1-6}$ haloalkyl, or is independently selected from

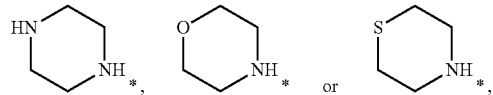 [SMILES: C1CNCCN1 ; C1COCCN1 ; C1CSCCN1]

any of which is optionally substituted with 1, 2, 3 or 4 $R_6$ groups;

or, $R_3$ is selected from H, halogen, $C_{1-6}$ alkyl, $C_{1-6}$ haloalkyl, —$OR_a$, —O—$C_{1-6}$ alkylene-$R_6$ or -L'-3- to 7-membered heterocyclyl, each of which is optionally substituted with 1 or 2 $R_6$ groups; preferably, $R_3$ is selected from —O—$C_{1-6}$ alkylene-$R_6$, -L'-3- to 11-membered heterocyclyl or —C(O)$NR_bR_c$, each of which is optionally substituted with 1 or 2 $R_6$ groups;

$R_4$ is selected from $C_{1-6}$ alkyl, $C_{1-6}$ haloalkyl, $C_{3-7}$ cycloalkyl, or 3- to 7-membered heterocyclyl; preferably, $R_4$ is selected from $C_{1-6}$ alkyl, $C_{1-6}$ haloalkyl or $C_{3-7}$ cycloalkyl; preferably, $R_4$ is selected from $C_{1-6}$ alkyl or $C_{3-7}$ cycloalkyl; preferably, $R_4$ is isopropyl; preferably, $R_4$ is cyclopentyl; preferably, $R_4$ is cyclopropyl;

$R_5$ is H;

$R_6$ is independently selected from H, —$NH_2$, —$NHC_{1-6}$ alkyl, —$N(C_{1-6}$ alkyl$)_2$, $C_{1-6}$ alkyl, $C_{1-6}$ haloalkyl or —$C_{0-6}$ alkylene-$OR_a$; preferably, $R_6$ is independently selected from H, —$NH_2$, —$NHC_{1-6}$ alkyl, —$N(C_{1-6}$ alkyl$)_2$, $C_{1-6}$ alkyl or —$C_{0-6}$ alkylene-$OR_a$; preferably, $R_6$ is independently selected from H, —$NH_2$, —$NHC_{1-6}$ alkyl, —$N(C_{1-6}$ alkyl$)_2$, $C_{1-6}$ alkyl or $C_{1-6}$ haloalkyl; preferably, $R_6$ is independently selected from H, $C_{1-6}$ alkyl, $C_{1-6}$ haloalkyl or —$C_{0-6}$ alkylene-$OR_a$; preferably, $R_6$ is independently selected from H, $C_{1-6}$ alkyl or $C_{1-6}$ haloalkyl;

$R_a$ is selected from H or $C_{1-6}$ alkyl;

$R_b$ and $R_c$ are independently selected from H or 3- to 7-membered heterocyclyl;

L' is selected from a chemical bond, —O—, —NH—, —C(O)—, —C(O)NH— or —NHC(O)—.

In a more specific embodiment, the present disclosure refers to a compound of formula (I), or a pharmaceutically acceptable salt, enantiomer, diastereomer, racemate, or mixture thereof, wherein the said compound of formula (I) has one of structures of the following general formulae:

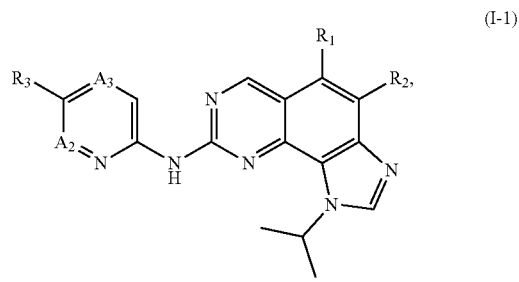
(I-1)

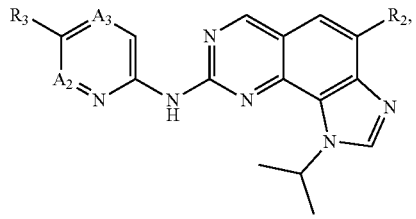
(I-2)

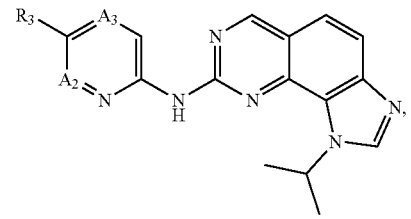
(I-3)

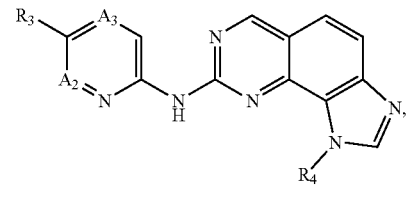
(I-4)

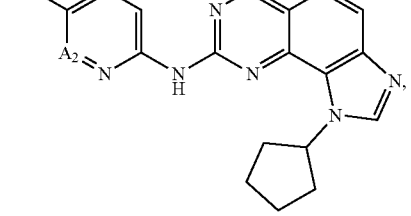
(I-5)

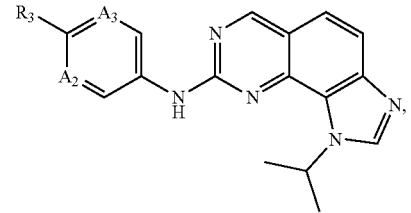
(I-6)

wherein the groups are as defined above.

In a specific embodiment, the present disclosure refers to a compound of formula (II), or a pharmaceutically acceptable salt, enantiomer, diastereomer, racemate, or mixture thereof:

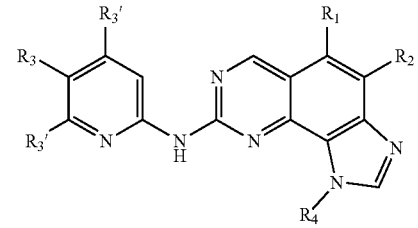
(II)

wherein:

R$_1$ is selected from H, C$_{1-6}$ alkyl or C$_{1-6}$ haloalkyl; preferably, R$_1$ is selected from H or C$_{1-6}$ alkyl; preferably, R$_1$ is selected from H or methyl; preferably, R$_1$ is H;

R$_2$ is selected from H, halogen, C$_{1-6}$ alkyl or C$_{1-6}$ haloalkyl; preferably, R$_2$ is selected from H, halogen or C$_{1-6}$ alkyl; preferably, R$_2$ is selected from H, halogen or methyl; preferably, R$_2$ is selected from halogen or C$_{1-6}$ alkyl; preferably, R$_2$ is selected from halogen or methyl; preferably, R$_2$ is H; preferably, wherein the said halogen is Br;

R$_3$ is selected from 3- to 11-membered heterocyclyl which is optionally substituted with 1, 2, 3 or 4 R$_6$ groups; R$_3$ is selected from 5- to 6-membered heterocyclyl which is optionally substituted with 1, 2, 3 or 4 R$_6$ groups;

preferably, R$_3$ is selected from

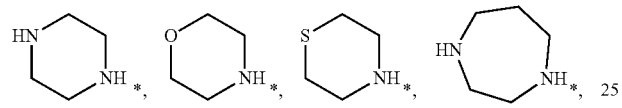

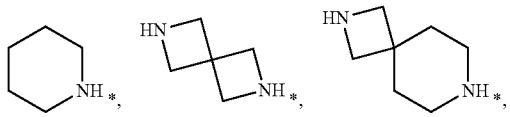

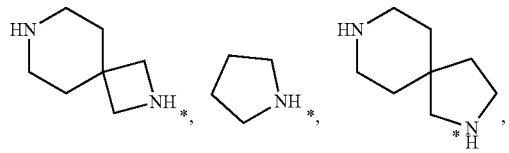

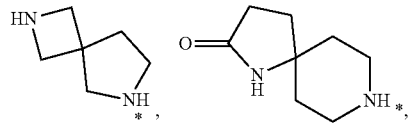

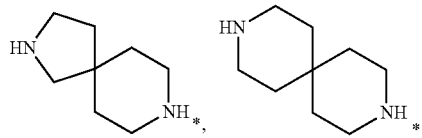

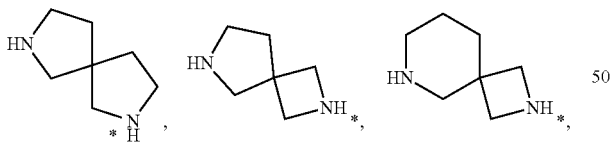

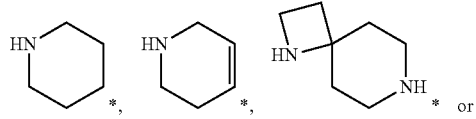

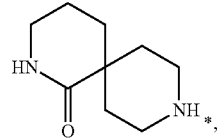

any of which is optionally substituted with 1, 2, 3 or 4 R$_6$ groups;

preferably, R$_3$ is selected from

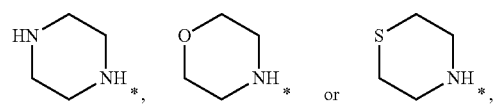 [SMILES: C1CNCCN1 ; C1COCCN1 ; C1CSCCN1]

any of which is optionally substituted with 1, 2, 3 or 4 R$_6$ groups;

preferably, R$_3$ is selected from

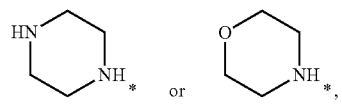

any of which is optionally substituted with 1, 2, 3 or 4 R$_6$ groups;

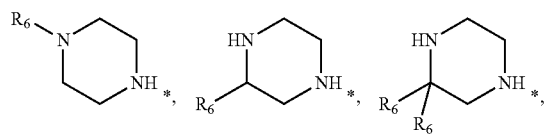

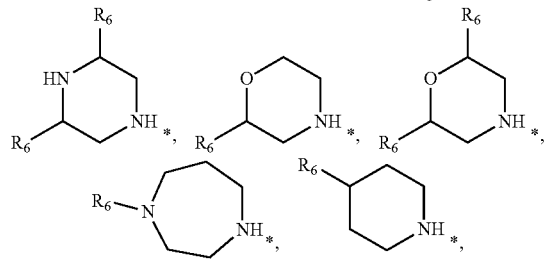

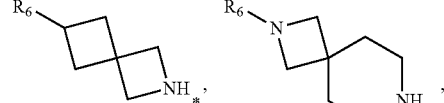

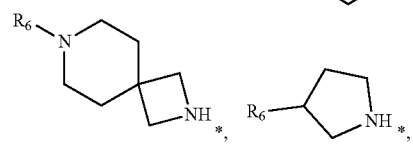

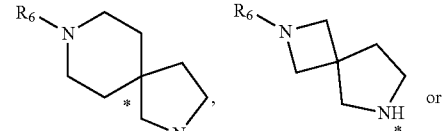

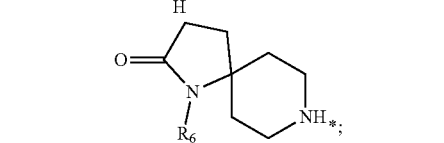

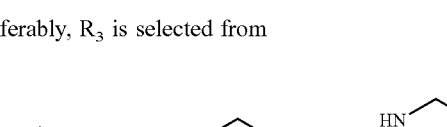

preferably, R$_3$ is selected from

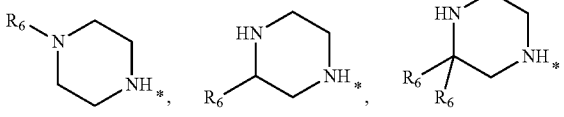

-continued

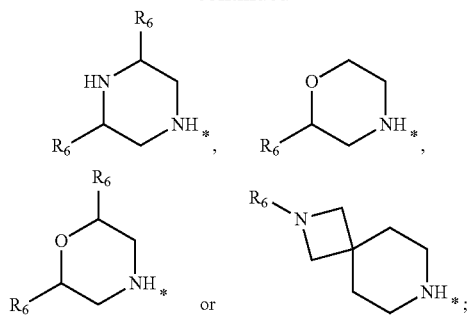

preferably, R₃ is selected from

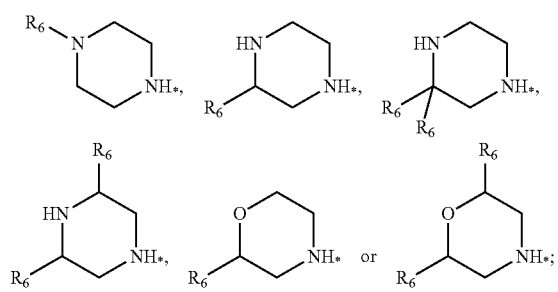

preferably, R₃ is selected from

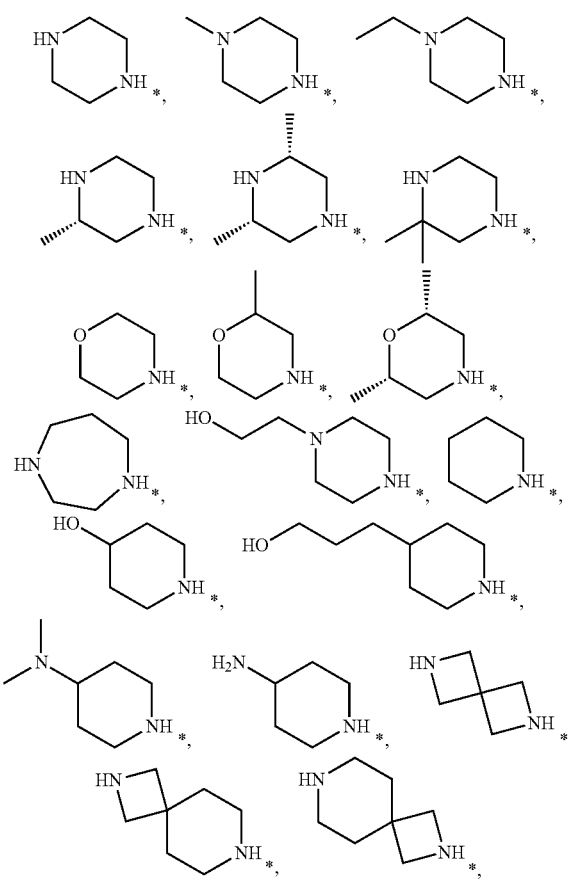

-continued

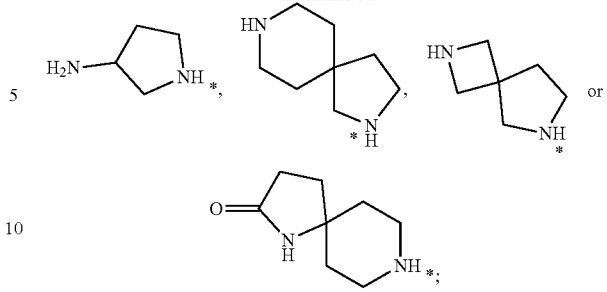

preferably, R₃ is selected from

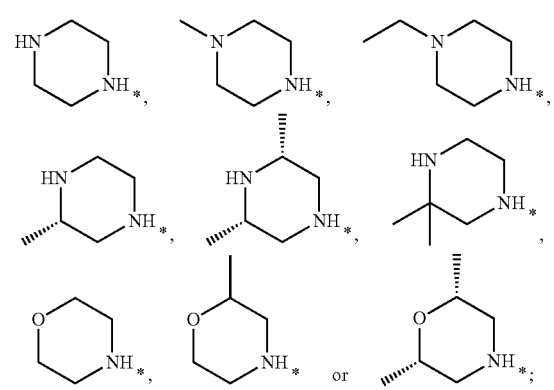

or, R₃ is selected from —O—C$_{1-6}$ alkylene-R₆, -L'-3- to 11-membered heterocyclyl or —C(O)NR$_b$R$_c$, each of which is optionally substituted with 1 or 2 R₆ groups; preferably, R₃ is selected from

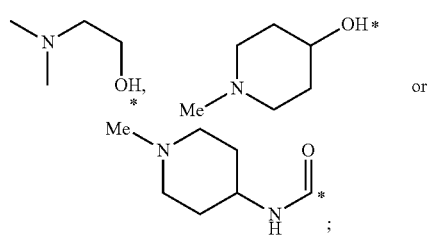

R₃' is independently selected from H, halogen, C$_{1-6}$ alkyl or C$_{1-6}$ haloalkyl; preferably, R₃' is independently selected from H, C$_{1-6}$ alkyl or C$_{1-6}$ haloalkyl; preferably, R₃' is independently selected from H or C$_{1-6}$ alkyl; preferably, R₃' is independently selected from H or methyl; preferably, R₃' is independently selected from H, halogen, C$_{1-6}$ alkyl or —OR$_a$; preferably, R₃' is independently —OR$_a$; preferably, R₃' is independently —OMe;

R₄ is selected from C$_{1-6}$ alkyl, C$_{1-6}$ haloalkyl, C$_{3-7}$ cycloalkyl, or 3- to 7-membered heterocyclyl; preferably, R₄ is selected from C$_{1-6}$ alkyl, C$_{1-6}$ haloalkyl or C$_{3-7}$ cycloalkyl; preferably, R₄ is selected from C$_{1-6}$ alkyl or C$_{3-7}$ cycloalkyl; preferably, R₄ is selected from cyclopropyl, cyclobutyl, cyclopentyl, ethyl or isopropyl; preferably, R₄ is selected from cyclopropyl, cyclopentyl or isopropyl; preferably, R₄ is selected from cyclopentyl or isopropyl;

$R_6$ is independently selected from H, —$NH_2$, —$NHC_{1-6}$ alkyl, —$N(C_{1-6}$ alkyl$)_2$, $C_{1-6}$ alkyl, $C_{1-6}$ haloalkyl or —$C_{0-6}$ alkylene-$OR_a$; preferably, $R_6$ is independently selected from H, —$NH_2$, —$NHC_{1-6}$ alkyl, —$N(C_{1-6}$ alkyl$)_2$, $C_{1-6}$ alkyl or —$C_{0-6}$ alkylene-$OR_a$; preferably, $R_6$ is independently selected from H, —$NH_2$, —$NHC_{1-6}$ alkyl, —$N(C_{1-6}$ alkyl$)_2$, $C_{1-6}$ alkyl or $C_{1-6}$ haloalkyl; preferably, $R_6$ is independently selected from H, $C_{1-6}$ alkyl, $C_{1-6}$ haloalkyl or —$C_{0-6}$ alkylene-$OR_a$; preferably, $R_6$ is independently selected from H, $C_{1-6}$ alkyl or $C_{1-6}$ haloalkyl; preferably, $R_6$ is independently selected from H or $C_{1-6}$ alkyl;

$R_a$ is selected from H or $C_{1-6}$ alkyl;

$R_b$ and $R_c$ are independently selected from H or 3- to 7-membered heterocyclyl.

In a more specific embodiment, the present disclosure refers to a compound of the formula (II), or a pharmaceutically acceptable salt, enantiomer, diastereomer, racemate, or mixture thereof, wherein the said compound of the formula (II) has one of structures of the following general formulae:

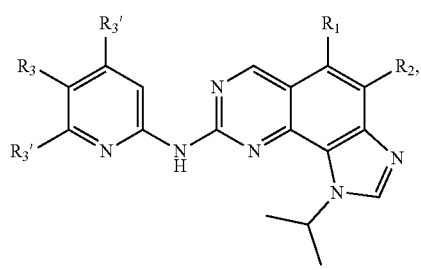
(II-1)

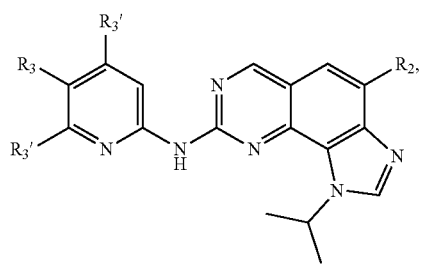
(II-2)

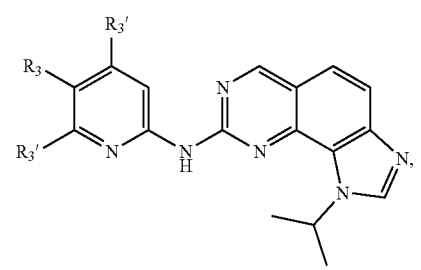
(II-3)

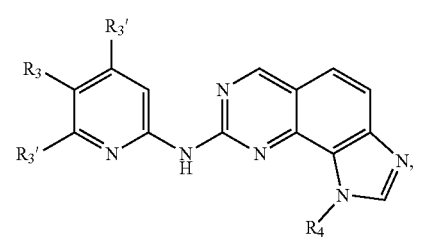
(II-4)

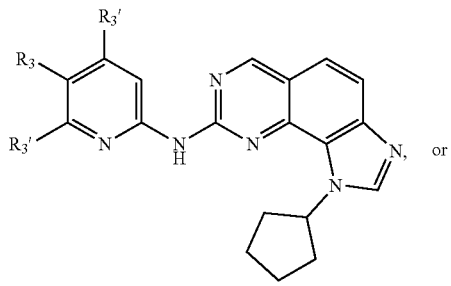
(II-5)

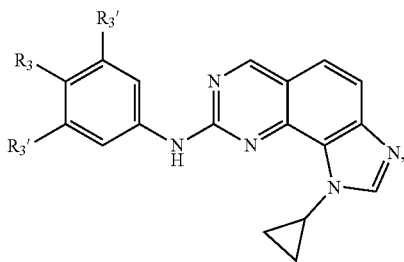
(II-6)

wherein the said groups are as defined above.

In a specific embodiment, the present disclosure refers to compound of the formula (III), or a pharmaceutically acceptable salt, enantiomer, diastereomer, racemate, or mixture thereof:

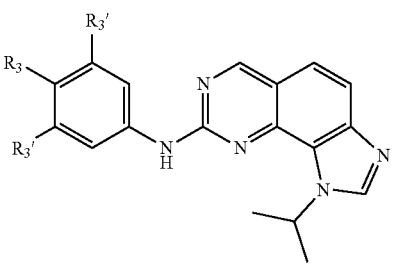
(III)

wherein, $R_3$ is selected from 5- to 6-membered heterocyclyl which is optionally substituted with 1, 2, 3 or 4 $R_6$ groups; preferably, $R_3$ is selected from

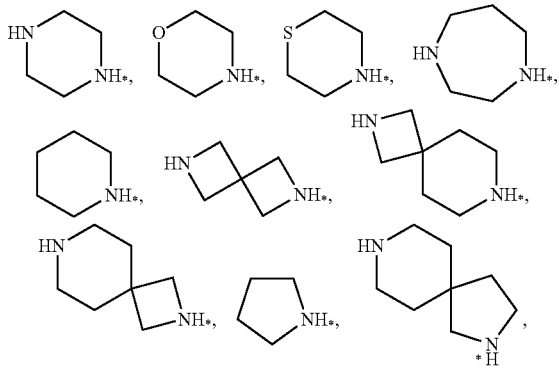

-continued

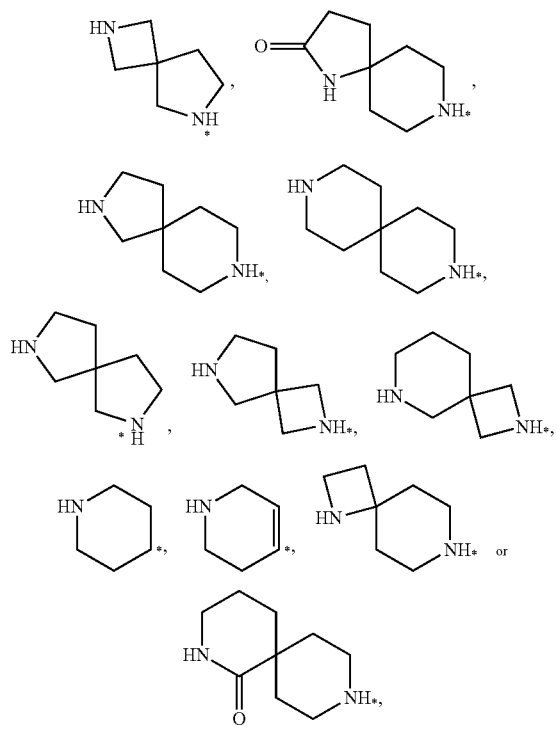

any of which is optionally substituted with 1, 2, 3 or 4 $R_6$ groups;

preferably, $R_3$ is selected from

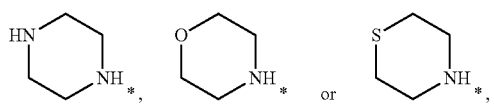

any of which is optionally substituted with 1, 2, 3 or 4 $R_6$ groups;

preferably, $R_3$ is selected from

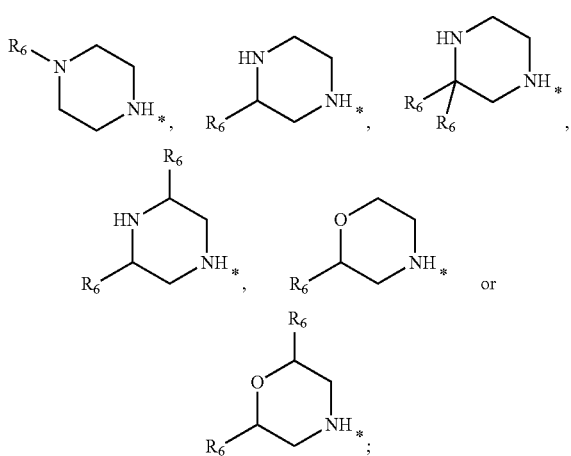

preferably, $R_3$ is selected from

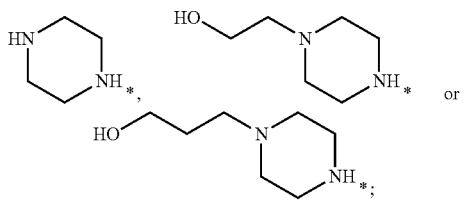

or, $R_3$ is selected from —O—$C_{1-6}$ alkylene-$R_6$ or -L'-3- to 11-membered heterocyclyl, each of which is optionally substituted with 1 or 2 $R_6$ groups; preferably, $R_3$ is selected from

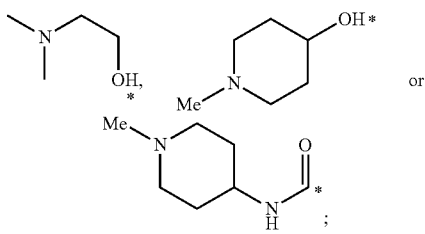

$R_3'$ is independently selected from H, halogen, $C_{1-6}$ alkyl or $C_{1-6}$ haloalkyl; preferably, $R_3'$ is independently selected from H, $C_{1-6}$ alkyl or $C_{1-6}$ haloalkyl; preferably, $R_3'$ is independently selected from H or $C_{1-6}$ alkyl; preferably, $R_3'$ is independently selected from H or methyl; preferably, $R_3'$ is independently selected from H, halogen, $C_{1-6}$ alkyl or —$OR_a$; preferably, $R_3'$ is independently —$OR_a$; preferably, $R_3'$ is independently —OMe;

$R_6$ is independently selected from H, —$NH_2$, —$NHC_{1-6}$ alkyl, —$N(C_{1-6}$ alkyl$)_2$, $C_{1-6}$ alkyl, $C_{1-6}$ haloalkyl or —$C_{0-6}$ alkylene-$OR_a$; preferably, $R_6$ is independently selected from H, —$NH_2$, —$NHC_{1-6}$ alkyl, —$N(C_{1-6}$ alkyl$)_2$, $C_{1-6}$ alkyl or —$C_{0-6}$ alkylene-$OR_a$; preferably, $R_6$ is independently selected from H, —$NH_2$, —$NHC_{1-6}$ alkyl, —$N(C_{1-6}$ alkyl$)_2$, $C_{1-6}$ alkyl or $C_{1-6}$ haloalkyl; preferably, $R_6$ is independently selected from H, $C_{1-6}$ alkyl, $C_{1-6}$ haloalkyl or —$C_{0-6}$ alkylene-$OR_a$; preferably, $R_6$ is independently selected from H, $C_{1-6}$ alkyl or $C_{1-6}$ haloalkyl; preferably, $R_6$ is independently selected from H or $C_{1-6}$ alkyl;

$R_a$ is selected from H or $C_{1-6}$ alkyl;

L' is selected from a chemical bond, —O—, —NH—, —C(O)—, —C(O)NH— or —NHC(O)—.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer (such as cis- and trans-isomer), or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses.

The present disclosure also provides a pharmaceutical formulation comprising a therapeutically effective amount of a compound of formula (I), or a therapeutically acceptable salt thereof, and a pharmaceutically acceptable carrier, diluent or excipient. All of these forms belong to the present disclosure.
The preferred compound disclosed herein includes but is not limited to the following compound:
I-1
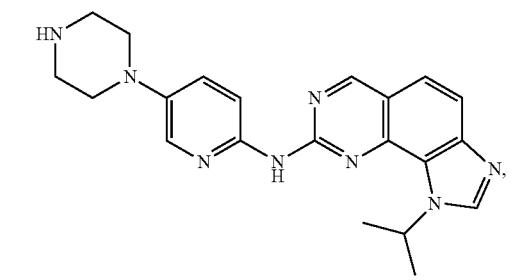
I-2
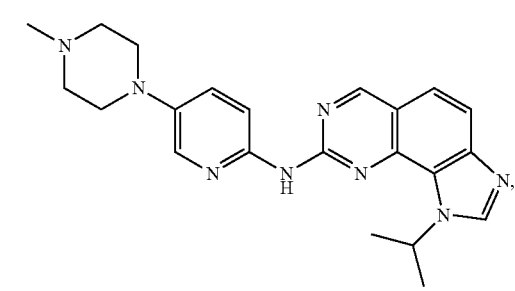
I-3
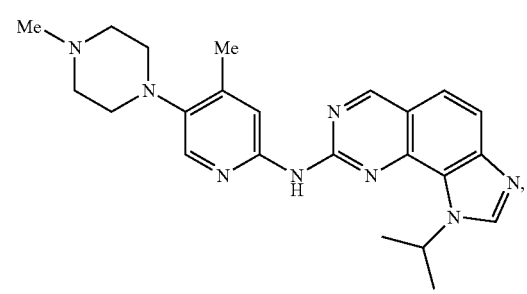
I-4
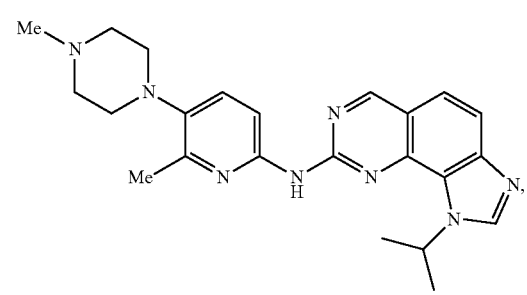
I-5
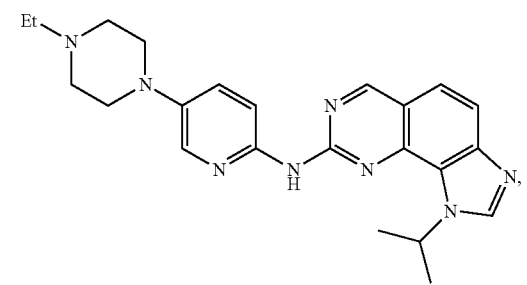
I-6
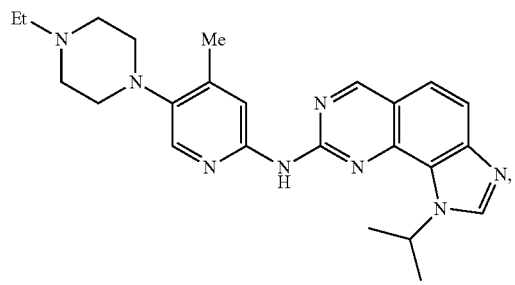
I-7
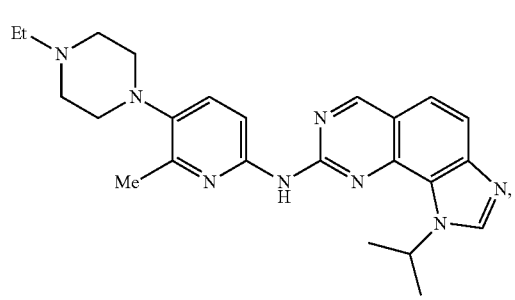
I-8
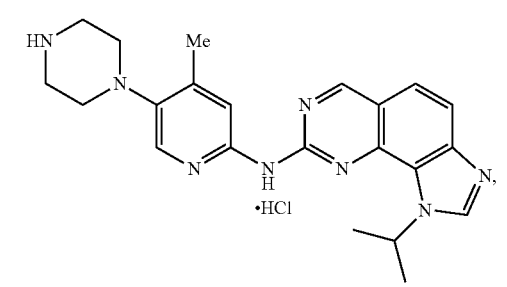
I-9
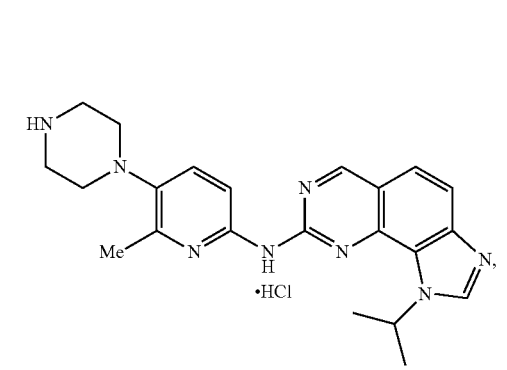
I-10
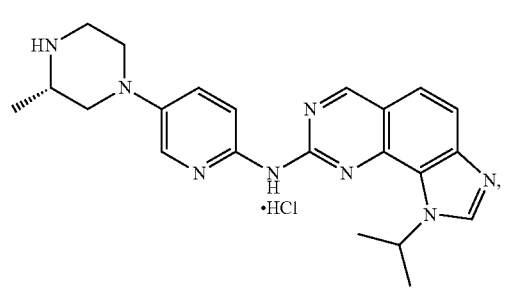

I-11
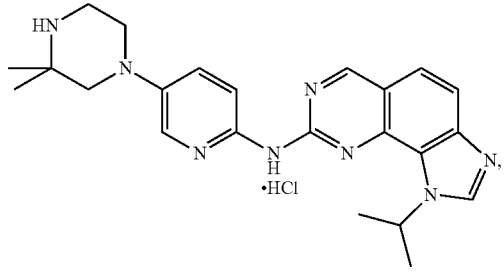
·HCl
I-12
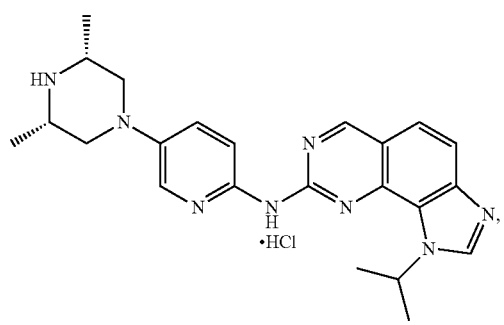
·HCl
I-13
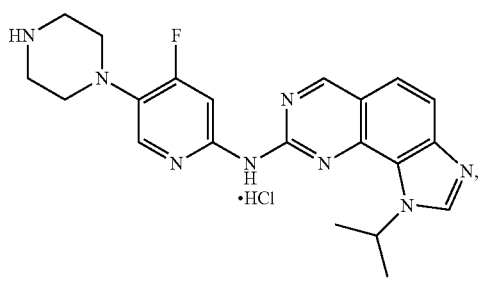
·HCl
I-14
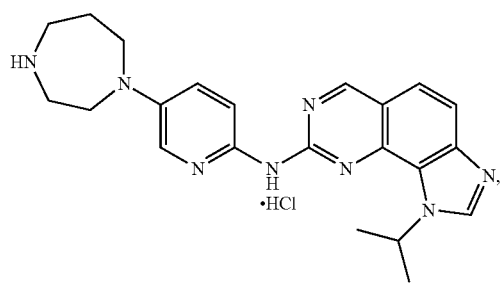
·HCl
I-15
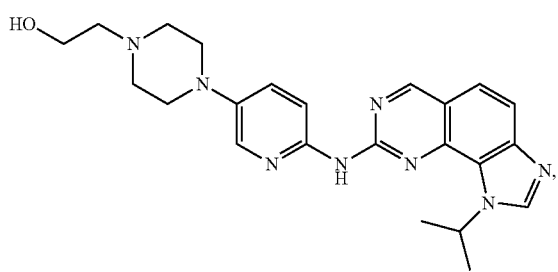
I-16
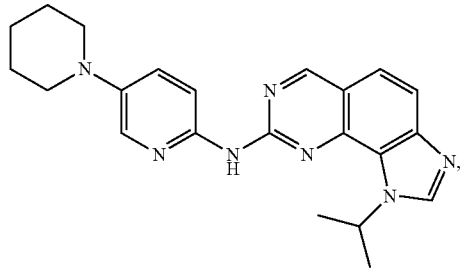
I-17
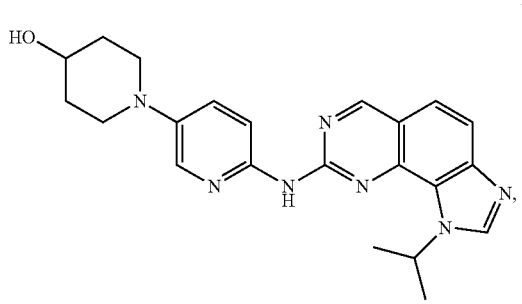
I-18
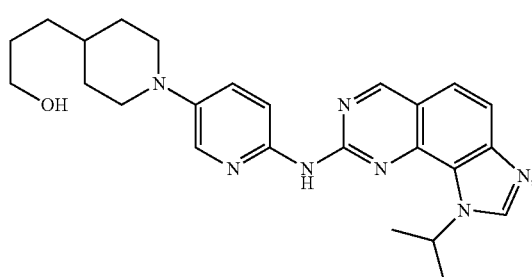
I-19
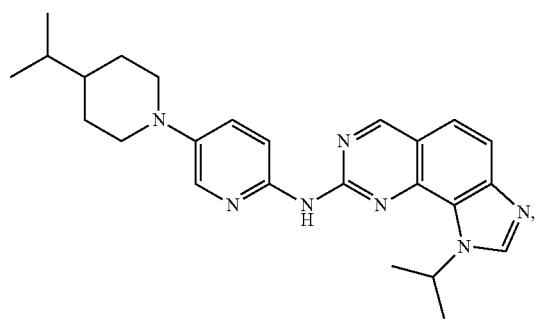
I-20
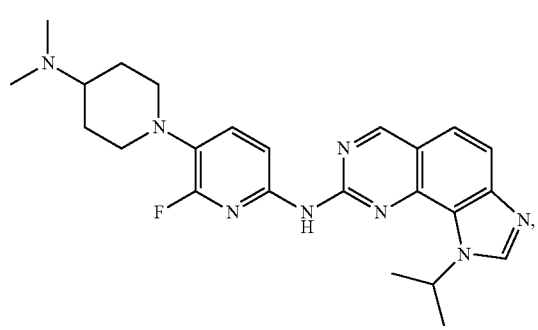

I-21
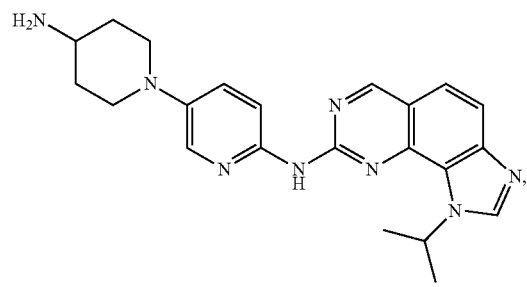
I-22
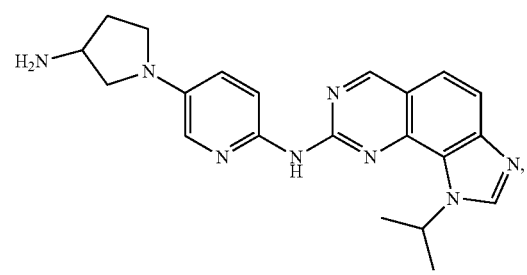
I-23
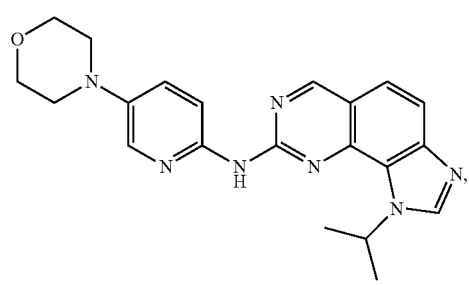
I-24
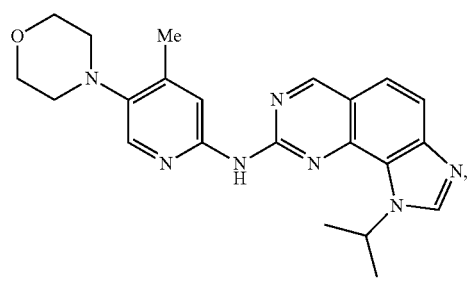
I-25
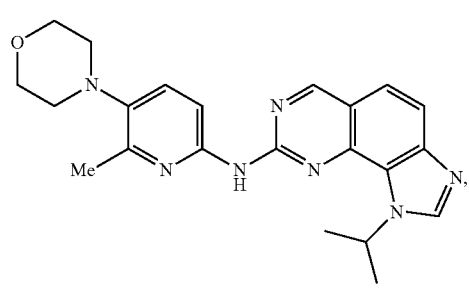
I-26
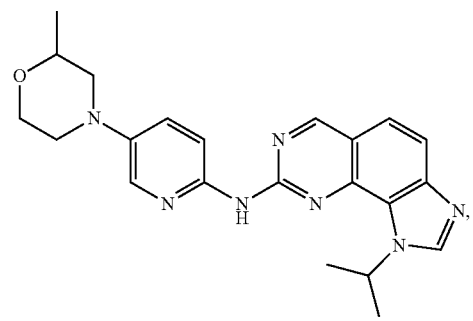
I-27
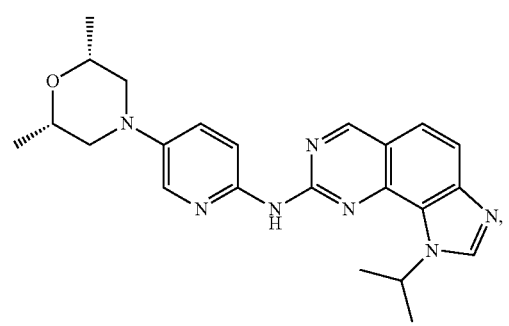
I-28
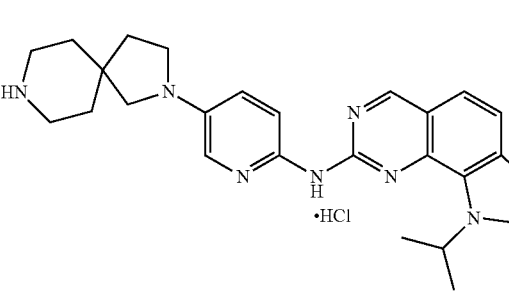
I-29
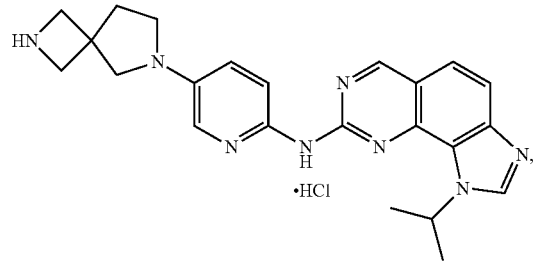
I-30
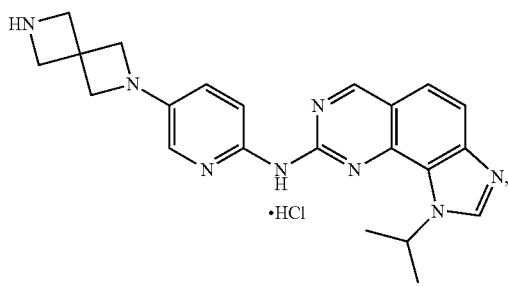

I-31
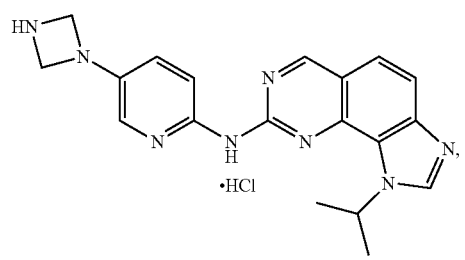
I-32
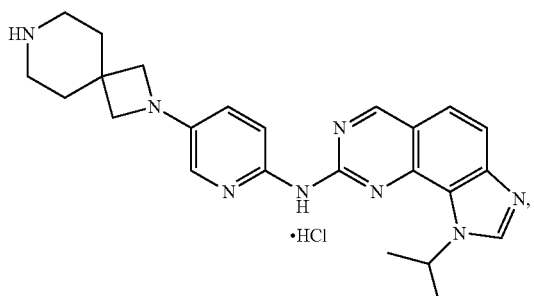
I-33
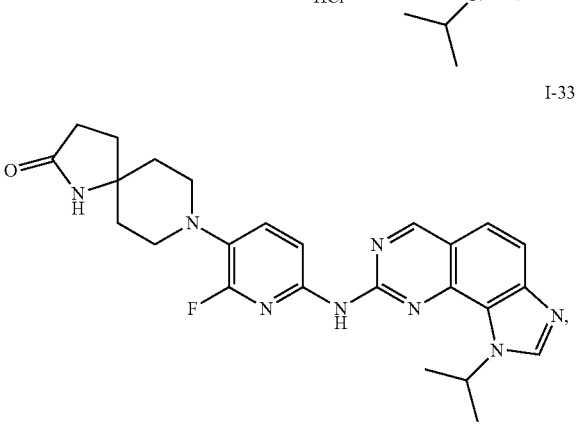
I-34
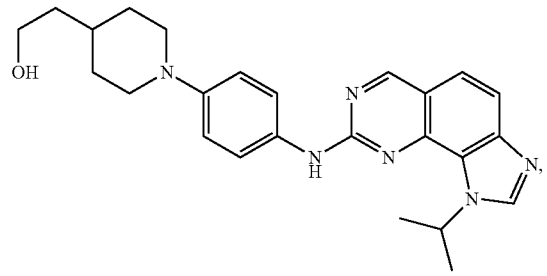
I-35
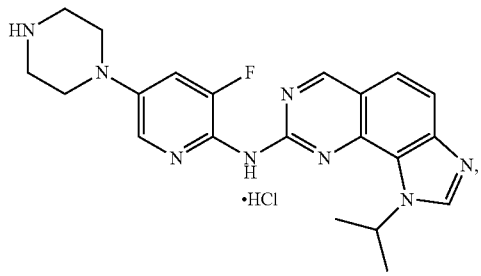
I-36
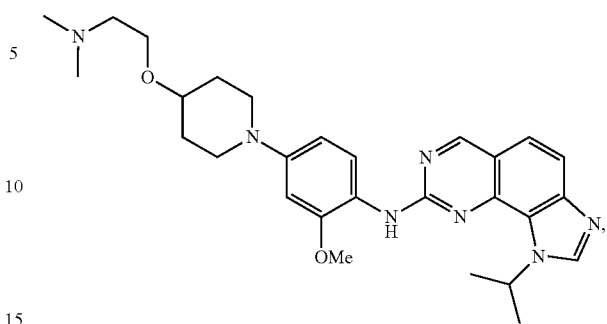
I-37
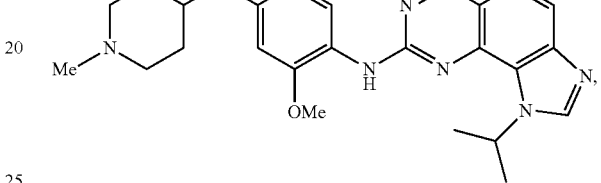
I-38
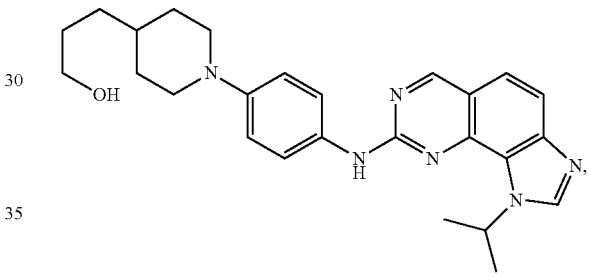
I-39
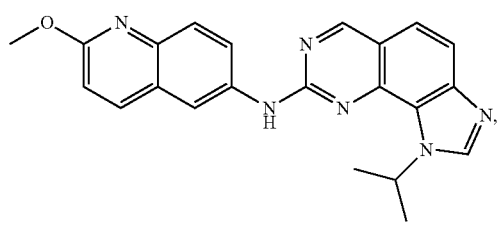
I-40
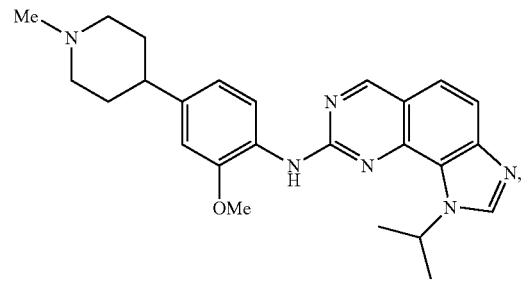

I-41
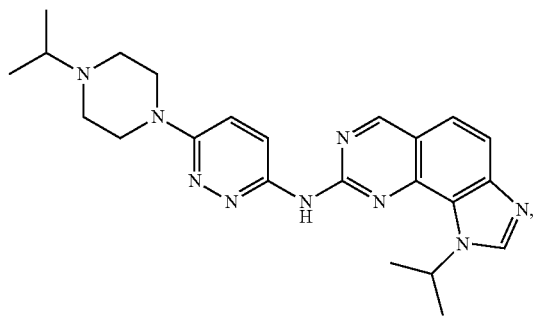
I-42
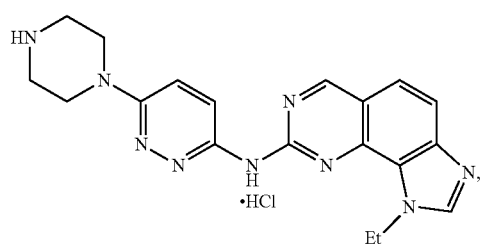
I-43
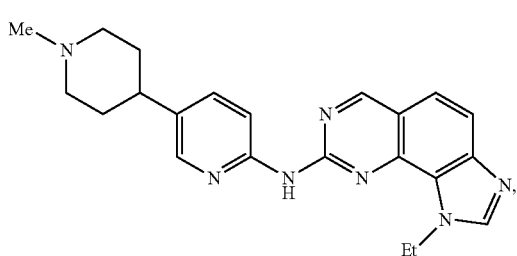
I-44
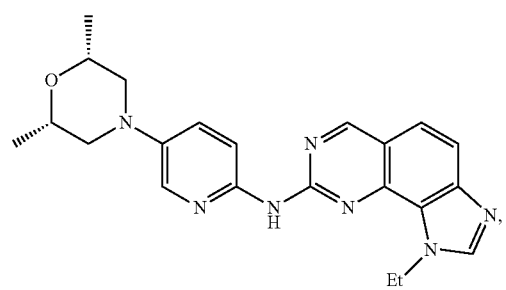
I-45
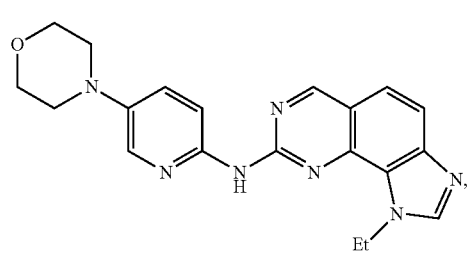
I-46
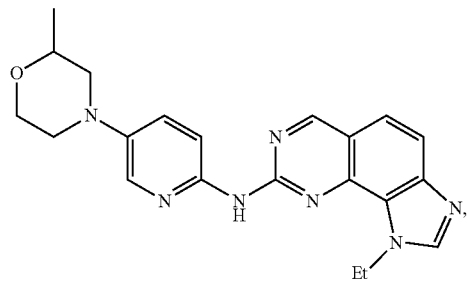
I-47
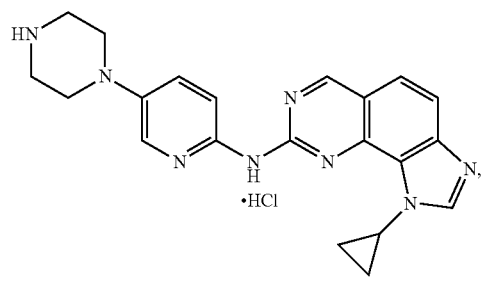
I-48
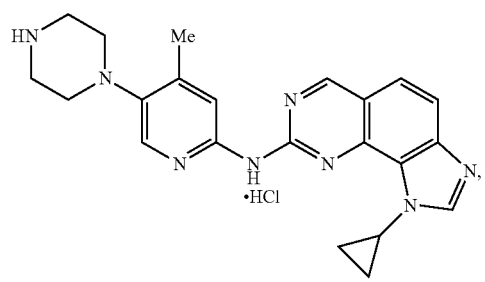
I-49
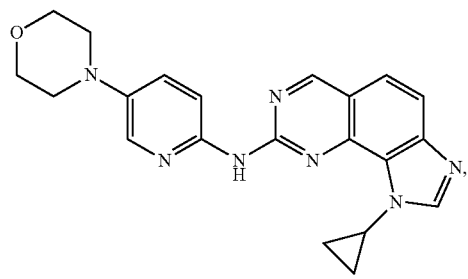
I-50
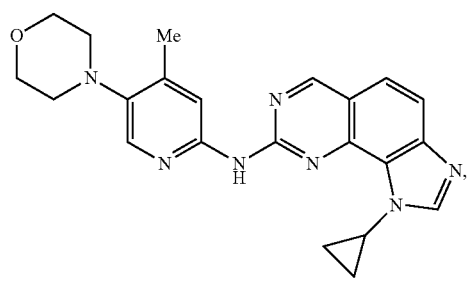

I-51
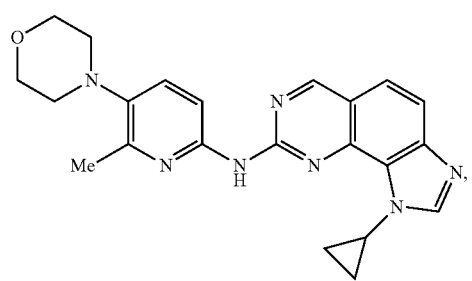
I-56
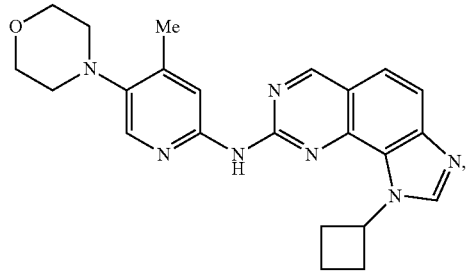
I-52
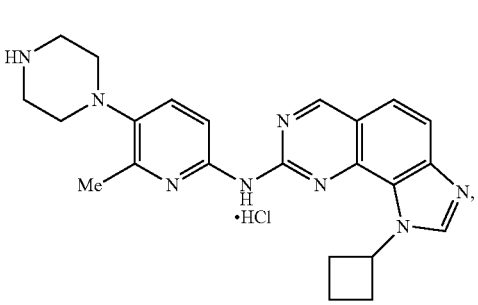
I-57
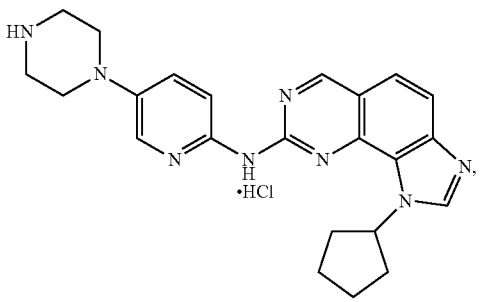
I-53
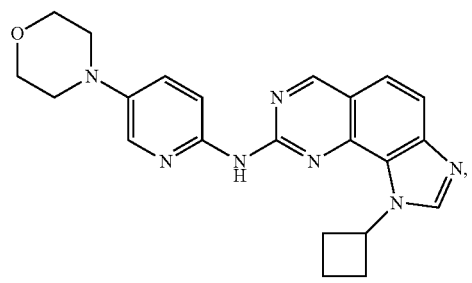
I-58
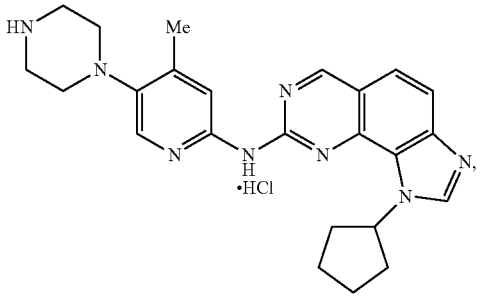
I-54
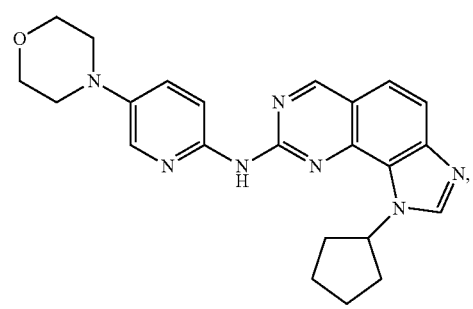
I-59
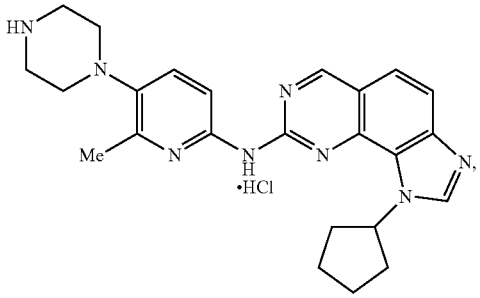
I-55
I-60

-continued
I-61
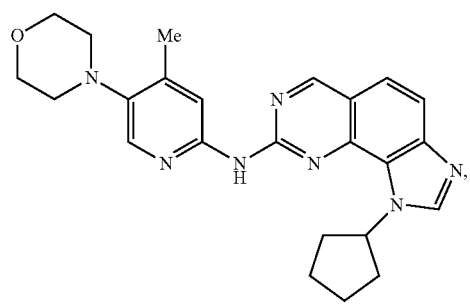
I-62
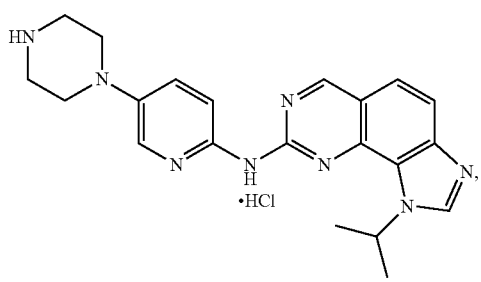
·HCl
I-63
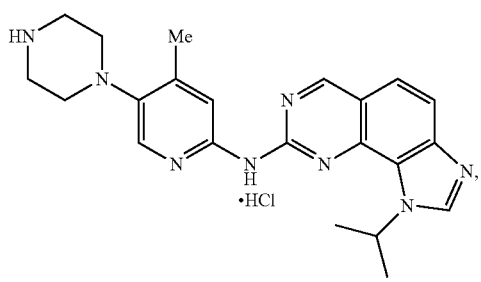
·HCl
I-64
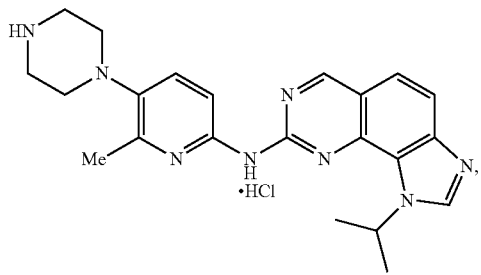
·HCl
I-65
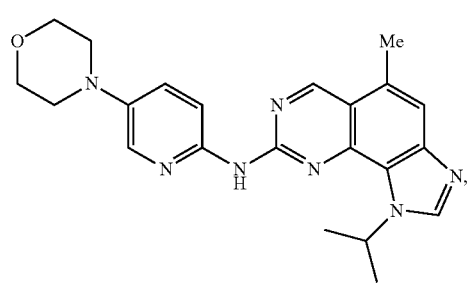
-continued
V-66
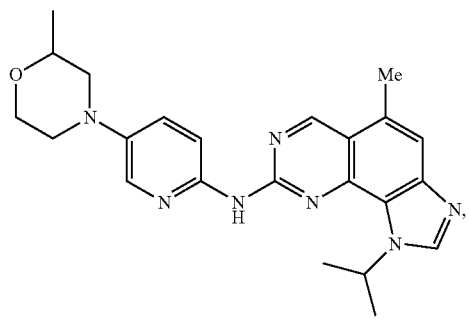
I-67
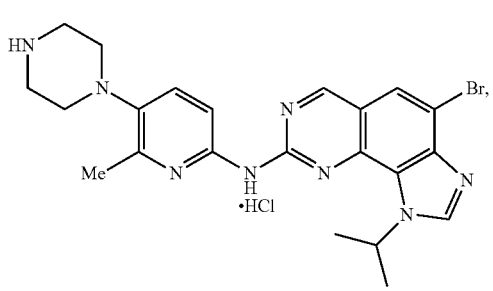
·HCl
I-68
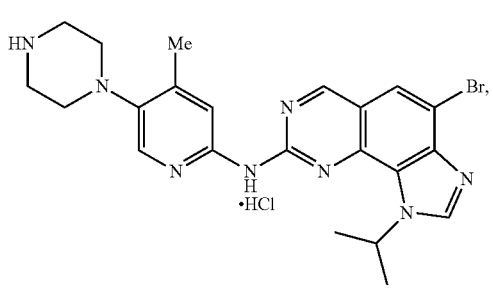
·HCl
I-69
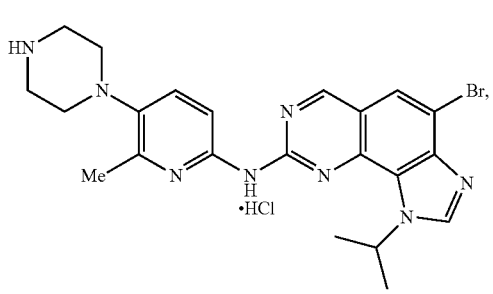
·HCl
I-70
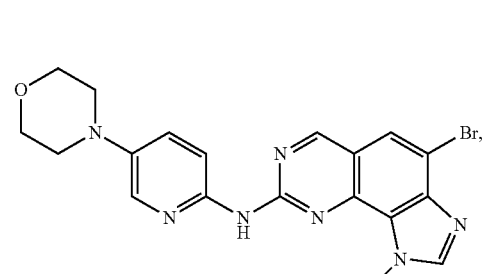

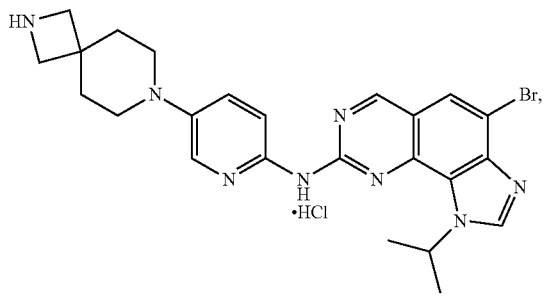

I-71

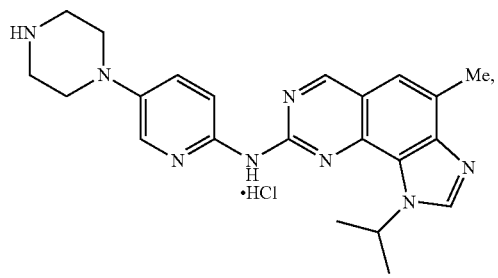

I-72

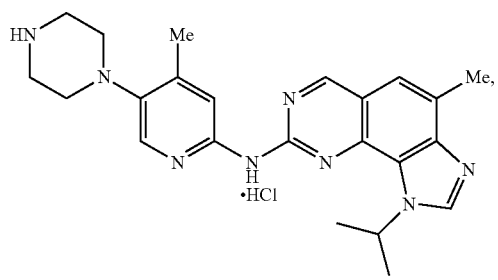

I-73

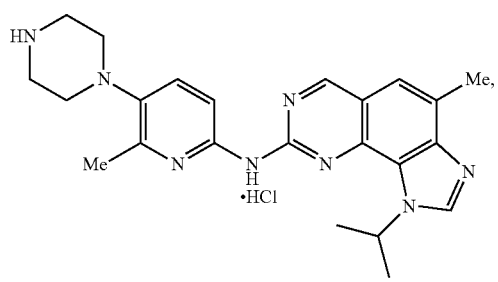

I-74

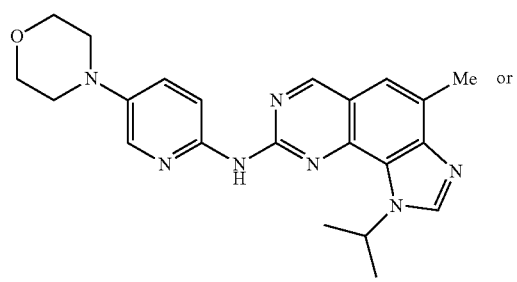

I-75

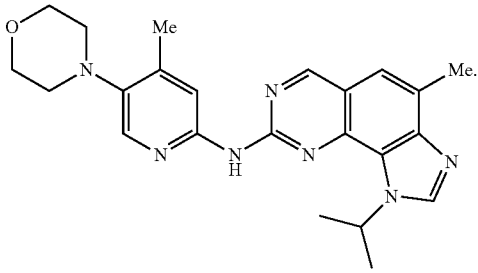

I-76

Pharmaceutical Compositions, Formulations and Kits

In another aspect, the disclosure provides a pharmaceutical composition comprising a compound of the present disclosure (also referred to as the "active ingredient") and a pharmaceutically acceptable excipient. In certain embodiments, the pharmaceutical composition comprises an effective amount of the compound of the present disclosure. In certain embodiments, the pharmaceutical composition comprises a therapeutically effective amount of the compound of the present disclosure. In certain embodiments, the pharmaceutical composition comprises a prophylactically effective amount of the compound of the present disclosure.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that can be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agent(s), and a first and a second containers (eg, vials, ampoules, bottles, syringes, and/or dispersible packages or other suitable container) containing the compound disclosed herein or other therapeutic agent(s). In some embodiments, kits provided can also optionally include a third container containing a pharmaceutically acceptable excipient for diluting or suspending the compound disclosed herein and/or other therapeutic agent(s). In some embodiments, the compound disclosed herein provided in the first container and the other therapeutic agent(s) provided in the second container is combined to form a unit dosage form.

Administration

The pharmaceutical composition provided by the present disclosure can be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present disclosure may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of the present disclosure can also be administered in sustained release forms or from sustained release drug delivery systems. A description of representative sustained release materials can be found in Remington's Pharmaceutical Sciences.

The present disclosure also relates to the pharmaceutically acceptable formulations of a compound of the present disclosure. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol. See, e.g., U.S. Pat. No. 5,376,645. In certain embodiments, the formulation comprises hexapropyl-β-cyclodextrin (e.g., 10-50% in water).

Treatment

The present disclosure provides methods for treating the following disorders or conditions in mammals, including humans: cell proliferative disorders such as cancer, vascular smooth muscle hyperplasia associated with atherosclerosis, postoperative vascular stenosis, restenosis, and endometriosis; infection, including viral infections such as DNA viruses e.g. herpes, and RNA viruses e.g. HIV, and fungal infections; autoimmune diseases such as psoriasis, inflammation, e.g. rheumatoid arthritis, lupus, type I diabetes, diabetic nephropathy, multiple sclerosis and glomerulonephritis; organ transplant rejection, including host versus graft disease, the method comprises administering to the mammal a therapeutically effective amount of a compound disclosed herein or a composition thereof.

The present disclosure further provides compounds disclosed herein useful in the treatment of abnormal cell proliferation, such as cancer. The disclosure further provides a method of treating abnormal cell proliferation, such as cancer selected from the following: breast, ovary, cervix, prostate, testis, esophagus, stomach, skin, lung, bone, colon, pancreas, thyroid, biliary tract, buccal cavity and pharynx (mouth), lips, tongue, mouth, pharynx, small intestine, colorectal, large intestine, rectum, cancer of brain and central nervous system, glioblastoma, neuroblastoma, keratoacanthoma, epidermoid carcinoma, large cell carcinoma, adenocarcinoma, adenoma, follicular carcinoma, undifferentiated carcinoma, papillary carcinoma, seminoma, melanoma, sarcoma, bladder cancer, liver cancer, kidney cancer, bone marrow disorder, lymphatic disorder, Hodgkin's disease, hairy cell carcinoma and leukemia, comprising administering to the patient in need of such treatment a therapeutically effective amount of a compound disclosed herein or a composition thereof.

Further, the present disclosure relates to a method of treating a subject having a disease caused by proliferation of vascular smooth muscle cells. The compounds disclosed herein effectively inhibit the proliferation and migration of vascular smooth muscle cells. The method comprises administering to a subject in need of treatment a compound disclosed herein or a composition thereof in an amount sufficient to inhibit vascular smooth muscle proliferation and/or migration.

The present disclosure further provides a method of treating a subject suffering from gout, comprising administering to the subject in need of treatment a compound disclosed herein or a composition thereof in an amount sufficient to treat the condition.

The present disclosure further provides a method of treating a subject having a renal disease, such as a polycystic kidney disease, comprising administering to the subject in need of treatment an amount of a compound disclosed herein or a composition thereof in an amount sufficient to treat the condition.

Due to their inhibitory activity against CDK and other kinases, the compounds disclosed herein are also useful research tools for studying the mechanism of action of these kinases in vitro and in vivo.

The compounds disclosed herein are useful in the treatment of cancer (e.g., leukemia and cancers of lung, breast, prostate and skin, such as melanoma) and other proliferative diseases including, but not limited to, psoriasis, HSV, HIV, restenosis, and atherosclerosis. To treat cancer with a compound disclosed herein, a therapeutically effective amount of a pharmaceutically acceptable composition comprising at least one compound disclosed herein is administered to a patient in need of such treatment, for example, who has cancer or another proliferative disorder.

An effective amount of a compound disclosed herein will generally be administered in a single or multiple doses at an average daily dose of from 0.01 mg to 50 mg of compound per kilogram of patient body weight, preferably from 0.1 mg to 25 mg of compound per kilogram of patient body weight. In general, the compounds disclosed herein may be administered to a patient in need of such treatment in a daily dosage range of from about 1 mg to about 3500 mg per patient, preferably from 10 mg to 1000 mg. For example, the daily dose per patient can be 10, 20, 30, 40, 50, 60, 70, 80, 90, 100, 150, 200, 250, 300, 350, 400, 500, 600, 700, 800, 900 or 1000 mg. It can be administered one or more times daily, weekly (or several days apart) or on an intermittent schedule. For example, the compound can be administered one or more times per day on a weekly basis (e.g., every Monday), continually or for several weeks, such as 4-10 weeks. Alternatively, the administration may be continued for several days (e.g., 2-10 days), followed by a few days (e.g., 1-30 days) without administration of the compound, and the cycle may be repeated indefinitely or repeated for a given number of times, such as 4-10. Cycles. For example, the compounds disclosed herein may be administered daily for 5 days, then intermittently for 9 days, then administered daily for 5 days, then intermittent for 9 days, and so on, and the cycle is repeated indefinitely or repeated 4-10 times.

EXAMPLES

The following examples are provided to provide those skilled in the art with a complete disclosure and description of how to implement, prepare and evaluate the methods and compounds claimed herein, and are intended to be illustrative only and not limiting the scope of the invention.

The preparation protocol of the compound disclosed herein is shown, for example, in Scheme 1.

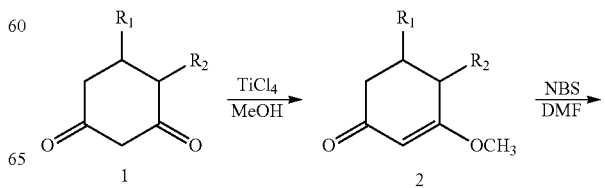

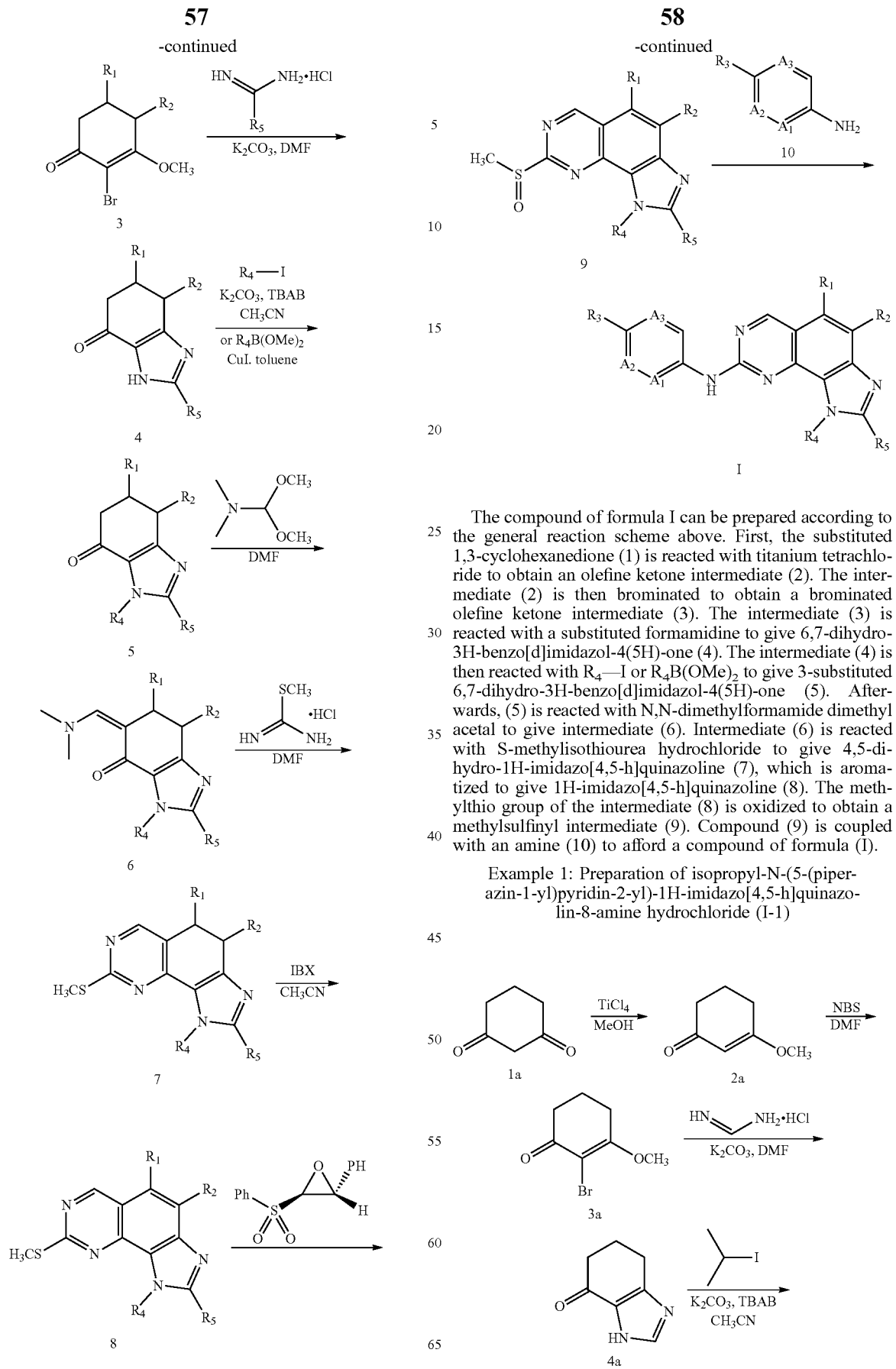

The compound of formula I can be prepared according to the general reaction scheme above. First, the substituted 1,3-cyclohexanedione (1) is reacted with titanium tetrachloride to obtain an olefine ketone intermediate (2). The intermediate (2) is then brominated to obtain a brominated olefine ketone intermediate (3). The intermediate (3) is reacted with a substituted formamidine to give 6,7-dihydro-3H-benzo[d]imidazol-4(5H)-one (4). The intermediate (4) is then reacted with $R_4$—I or $R_4B(OMe)_2$ to give 3-substituted 6,7-dihydro-3H-benzo[d]imidazol-4(5H)-one (5). Afterwards, (5) is reacted with N,N-dimethylformamide dimethyl acetal to give intermediate (6). Intermediate (6) is reacted with S-methylisothiourea hydrochloride to give 4,5-dihydro-1H-imidazo[4,5-h]quinazoline (7), which is aromatized to give 1H-imidazo[4,5-h]quinazoline (8). The methylthio group of the intermediate (8) is oxidized to obtain a methylsulfinyl intermediate (9). Compound (9) is coupled with an amine (10) to afford a compound of formula (I).

Example 1: Preparation of isopropyl-N-(5-(piperazin-1-yl)pyridin-2-yl)-1H-imidazo[4,5-h]quinazolin-8-amine hydrochloride (I-1)

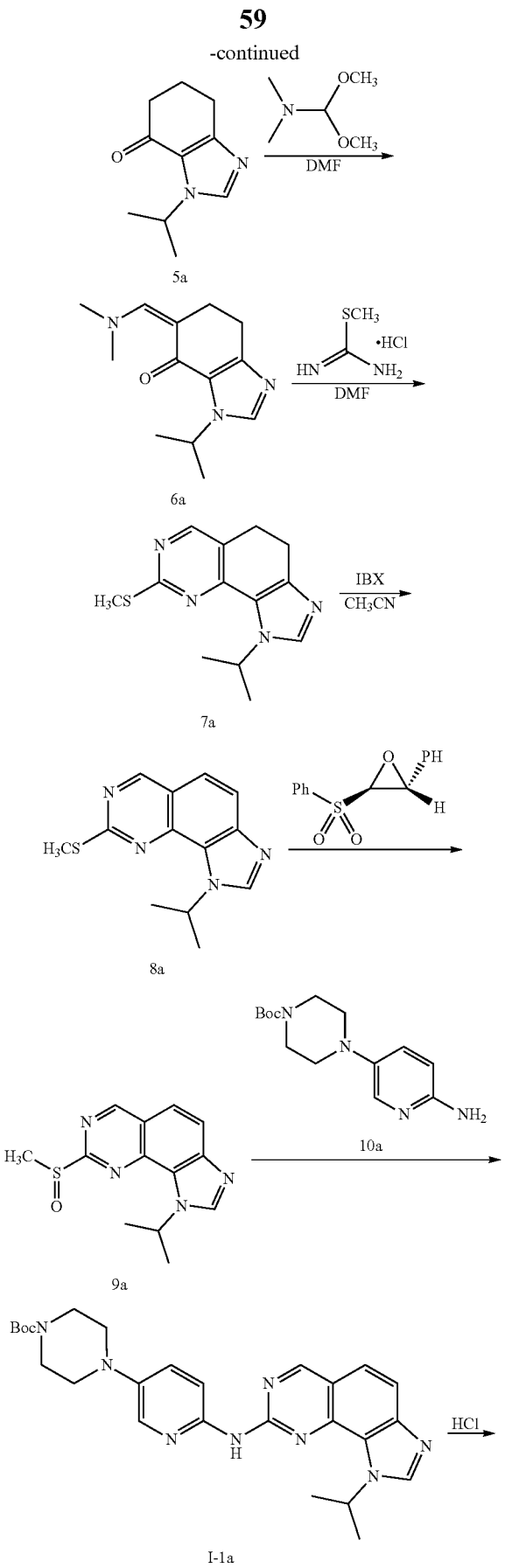

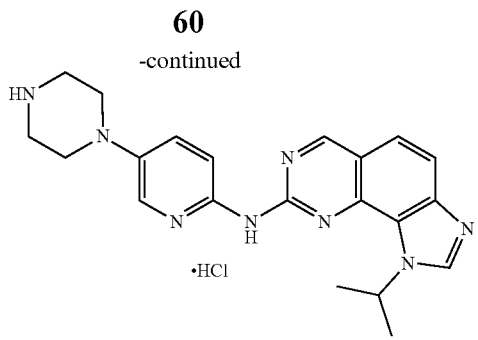

I-1

1): 3-Methoxycyclohex-2-enone (2a)

1,3-cyclohexanedione 1a (90 g, 804 mmol) was dissolved in methanol (800 mL), and to which titanium tetrachloride (2.6 mL, 24.2 mmol, 0.03 equiv.) was slowly added dropwise in an ice-water bath. After the addition, the reaction mixture was stirred for 1 hour at this temperature, and then saturated ammonium chloride aqueous solution (600 mL) was added to quench the reaction. After being concentrated, the reaction mixture was directly purified by flash silica gel column chromatography (petroleum ether/ethyl acetate=2:1) to afford a light yellow oil as the title compound 2a (86 g, 682 mmol, 84.9%). $^1$H NMR (600 MHz, chloroform-d, ppm) δ 5.37 (s, 1H), 3.68 (s, 3H), 2.39 (t, J=6.3 Hz, 2H), 2.33 (t, J=6.6 Hz, 2H), 1.99-1.94 (m, 2H); LC-MS (ESI), $C_7H_{11}O_2$ [M+H]$^+$: m/z=127.1.

2): 2-Bromo-3-methoxycyclohex-2-enone (3a)

2a (84 g, 666.6 mmol) was dissolved in dichloromethane/N,N-dimethylformamide (9:1, 1000 mL), and to the reaction mixture N-bromosuccinimide (132.6 g, 700 mmol, 1.05 equiv.) was added at 5-10° C. in five portions. After the addition, the reaction was continued at this temperature for 1 hour. After sucking filtration, the filtrate was concentrated. The resulting residue was diluted with toluene (1000 mL), and immediately washed with ice water (200 mL) twice. After drying, the filtrate was concentrated to around 200 mL, and the residue was moved to an ice-water bath for 5 minutes' stirring. After sucking filtration, the resulting filter residue was dried in vacuo with an oil pump to afford a light yellow powder as the title compound 3a, which was directly used in the next step without further purification (110.2 g, 540 mmol, 81%). LC-MS (ESI), $C_7H_{10}BrO_2$ [M+H]$^+$: m/z=205.0, 207.1.

3): 6,7-Dihydro-3H-benzo[d]imidazol-4(5H)-one (4a)

3a (101 g, 500 mmol) was dissolved in N,N-dimethylformamide (800 mL), and to which potassium carbonate (206 g, 1.5 mol, 3 equiv.) and formamidine hydrochloride (60.4 g, 750 mmol, 1.5 equiv.) were added in an ice-water bath. The resulting reaction mixture was heated to 80° C., and reacted for 16 hours under the stirring with a mechanical stirrer. The reaction mixture was cooled to room temperature, diluted with dichloromethane (1000 mL) and filtered. The filtrate was concentrated and purified with flash silica gel column chromatography (petroleum ether/ethyl acetate=2:1) to afford a grey solid as the title compound (4a, 24.6 g, 180 mmol, 36%). $^1$H NMR (400 MHz, chloroform-d, ppm) δ 7.89 (s, 1H), 2.93 (t, J=6.2 Hz, 2H), 2.63-2.50 (m, 2H), 2.27-2.14 (m, 2H); LC-MS (ESI), $C_7H_9N_2O$ [M+H]$^+$: m/z=137.3.

4): 3-Isopropyl-6,7-dihydro-3H-benzo[d]imidazol-4(5H)-one (5a)

4a (24 g, 176.5 mmol), potassium carbonate (73 g, 529.4 mmol, 3.0 equiv.), tetrabutylammonium bromide (5.68 g, 17.65 mmol, 0.1 equiv.) were suspended in acetonitrile (400 mL). The resulting reaction mixture was stirred at room temperature for 30 mins, then 2-iodopropane (43.4 mL, 441.2 mmol, 2.5 equiv.) was added, and then the reaction mixture was heated to 50° C. and stirred for 14 hours. The reaction mixture was cooled to room temperature and filtered, concentrated, and the residue was purified by flash silica gel column chromatography (petroleum ether/ethyl acetate=2:1 to 0:1) to afford a brown oil as the title compound 5a (8.16 g, 45.9 mmol, 26%). $^1$H NMR (600 MHz, chloroform-d, ppm) δ 7.76 (s, 1H), 5.12 (p, J=6.7 Hz, 1H), 2.87 (t, J=6.2 Hz, 2H), 2.52 (t, J=6.4 Hz, 2H), 2.13 (p, J=6.3 Hz, 2H), 1.48 (d, J=6.7 Hz, 6H); LC-MS (ESI), $C_{10}H_{15}N_2O$ [M+H]$^+$: m/z=179.1.

5): (Z)-5-((dimethylamino)methylene)-3-isopropyl-6,7-dihydro-3H-benzo[d]imidazol-4(5H)-one (6a)

A solution of 5a (8.0 g, 44.94 mmol) and N,N-dimethylformamide dimethyl acetal (59.6 mL, 449.4 mmol, 10 equiv.) in N,N-dimethylformamide (60 mL) was stirred at 130° C. for 13 hours. After the reaction mixture was cooled to room temperature, it was concentrated under reduced pressure to afford a brown oil as the title compound 6a (8.6 g, 37.0 mmol, 82.3%), which is a crude, and can be directly used in the next step without further purification. LC-MS (ESI), $C_{13}H_{20}N_3O$ [M+H]$^+$: m/z=234.2.

6): 1-Isopropyl-8-methylthio-4,5-dihydro-1H-imidazo[4,5-h]quinazoline (7a)

6a (8.3 g, 35.6 mmol) and S-methylisothiourea hydrochloride (13.46 g, 106.8 mmol, 3 equiv.) were suspended in N,N-dimethylformamide (100 mL), and heated to 110° C., stirred for 16 hours. After the reaction mixture was cooled to room temperature, it was diluted with about 200 mL ice water, and then extracted with ethyl acetate three times. The combined organic phase was washed with brine, dried over anhydrous sodium sulfate, and filtered, and the filtrate was concentrated and purified with flash silica gel column chromatography (petroleum ether/ethyl acetate=1:1 to 0:1) to afford a brown solid as the title compound (7a, 4.54 g, 17.44 mmol, 49%). $^1$H NMR (400 MHz, chloroform-d, ppm) δ 8.31 (s, 1H), 8.24 (s, 1H), 3.08 (t, J=8.2 Hz, 2H), 2.99 (t, J=7.4 Hz, 2H), 2.55 (s, 3H), 1.62 (d, J=6.7 Hz, 6H); LC-MS (ESI), $C_{13}H_{17}N_4S$ [M+H]$^+$: m/z=261.2.

7): 1-Isopropyl-8-methylthio-1H-imidazo[4,5-h]quinazoline (8a)

7a (4.2 g, 16.16 mmol) was dissolved in acetonitrile (150 mL), to which 2-iodoxybenzoic acid (9.06 g, 32.4 mmol, 2 eqiuv.) was added, and the mixture was heated to 75° C., and stirred for 16 hours. After the reaction mixture was cooled to room temperature, it was filtered, and concentrated. The resulting residue was purified with flash silica gel column chromatography to afford a light yellow solid as the title compound (8a, 3.66 g, 14.22 mmol, 88%). $^1$H NMR (300 MHz, methanol-d$_4$, ppm): δ 9.29 (s, 1H), 8.61 (s, 1H), 7.88-7.80 (m, 2H), 6.12-6.03 (m, 1H), 2.73 (s, 3H), 1.76 (d, J=6.6 Hz, 6H); LC-MS (ESI), $C_{13}H_{15}N_4S$ [M+H]$^+$: m/z=259.2.

8): 1-Isopropyl-8-methylsulfinyl-1H-imidazo[4,5-h]quinazoline (9a)

8a (1.4 g, 5.43 mmol) was dissolved in chloroform (15 mL), to which 2-phenylsulfonyl-3-phenyloxaziridine (1.7 g, 6.52 mmol, 1.2 equiv.) was added, and the mixture was stirred at room temperature for 18 hours. After concentration, the resulting crude was purified with flash silica gel column chromatography (petroleum ether/acetone=1:1 to 0:1) to afford a white solid as the title compound (9a, 1.34 g, 4.89 mmol, 90%). $^1$H NMR (400 MHz, chloroform-d, ppm): δ 9.53 (s, 1H), 8.36 (s, 1H), 8.15 (d, J=8.4 Hz, 1H), 7.82 (d, J=8.4 Hz, 1H), 6.04-5.98 (m, 1H), 3.05 (s, 3H), 1.76 (t, J=7.6 Hz, 6H); LC-MS (ESI), $C_{13}H_{15}N_4OS$ [M+H]$^+$: m/z=275.3.

9): Tert-butyl 4-(6-(1-isopropyl-1H-imidazo[4,5-h]quinazolin-8-ylamino)pyridin-3-yl)piperazine-1-carboxylate (I-1a)

9a (44.3 mg, 0.16 mmol) and tert-butyl 4-(6-aminopyridin-3-yl)piperazine-1-carboxylate (10a, 89.9 mg, 0.32 mmol) were suspended in xylene (1.6 mL), which was sealed with rubber stopper and the atmosphere was replaced with argon for 3 times, and the mixture was heated to 150° C. and reacted for 24 hours. After the reaction mixture was cooled to room temperature, ethyl acetate (0.3 mL) was added, and the stirring was continued for about 2 hours. After the precipitated solid was filtered off, the solution was purified with column chromatography to afford yellow powder as the title compound I-1a (17.2 mg, 21.8%). $^1$H NMR (400 MHz, chloroform-d, ppm): δ 9.19 (s, 1H), 8.40 (s, 1H), 8.32 (d, J=9.2 Hz, 1H), 8.24 (s, 1H), 8.08 (d, J=2.4 Hz, 1H), 7.75 (d, J=8.4 Hz, 1H), 7.56 (d, J=8.4 Hz, 1H), 7.35 (dd, J=9.0, 3.0 Hz, 1H), 6.13-6.03 (m, 1H), 3.63 (t, J=5.2 Hz, 4H), 3.13 (t, J=5.0 Hz, 4H), 1.73 (d, J=6.8 Hz, 6H), 1.50 (s, 9H).

10): 1-Isopropyl-N-(5-(piperazin-1-yl)pyridin-2-yl)-1H-imidazo[4,5-h]quinazolin-8-amine hydrochloride (I-1)

I-1a (14.9 mg, 0.03 mmol) was dissolved in dichloromethane (2 mL), to which HCl in 1,4-dioxane (4 N, 0.76 mL) was added, and the mixture was stirred at room temperature for 2 hours. After sucking filtration, the resulting filter residue was subjected to vacuum drying to a constant weight with an oil pump to give a yellow powder as the title compound I-1 (13 mg, 99%). $^1$H NMR (400 MHz, water-d$_2$, ppm): δ 9.55 (s, 1H), 9.39 (s, 1H), 8.12-8.09 (m, 2H), 7.85 (d, J=8.8 Hz, 1H), 7.81 (s, 1H), 7.85 (d, J=9.6 Hz, 1H), 6.00-5.93 (m, 1H), 3.56-3.51 (m, 8H), 1.79 (d, J=6.8 Hz, 6H).

Example 2: Preparation of 1-isopropyl-N-(5-(4-methylpiperazin-1-yl)pyridin-2-yl)-1H-imidazo[4,5-h]quinazolin-8-amine (I-2)

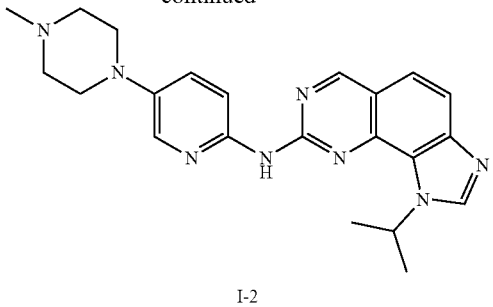

I-2

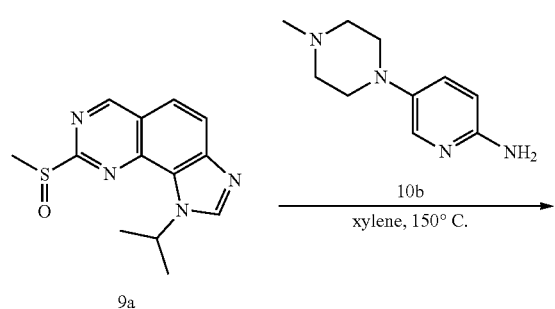

9a (30 mg, 0.11 mmol) and 10b (42.2 mg, 0.22 mmol) were suspended in xylene (0.3 mL), and the atmosphere was replaced by argon for 3 times. The mixture was heated to 150° C., and reacted overnight with stirring. After the mixture was cooled to room temperature, ethyl acetate (0.3 mL) was added, and the stirring was continued for about 2 hours. The mixture was filtered, and the filter residue was washed with ethyl acetate to afford a yellow solid as the title compound I-2 (13 mg, 32.5 mmol, 29.5%). $^1$H NMR (600 MHz, chloroform-d, ppm) δ 9.17 (s, 1H), 8.32 (brs, 1H), 8.28 (d, J=9.0 Hz, 1H), 8.21 (s, 1H), 8.09 (d, J=3.0 Hz, 1H), 7.73 (d, J=8.6 Hz, 1H), 7.56 (d, J=8.6 Hz, 1H), 7.33 (dd, J=9.0, 3.0 Hz, 1H), 6.07 (p, J=6.8 Hz, 1H), 3.22 (t, J=5.0 Hz, 4H), 2.63 (t, J=4.9 Hz, 4H), 2.38 (s, 3H), 1.73 (d, J=6.8 Hz, 6H).

TABLE 1

Examples I-3 to I-41

| Side chains | Products |
|---|---|
| 10c | I-3 |
| 10d | I-4 |

TABLE 1-continued
Examples I-3 to I-41
| Side chains | | Products | |
|---|---|---|---|
| 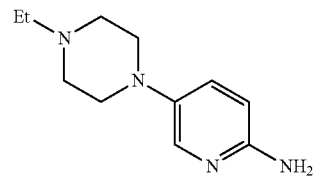 [SMILES: CCN1CCN(c2ccc(N)nc2)CC1] | 10e | 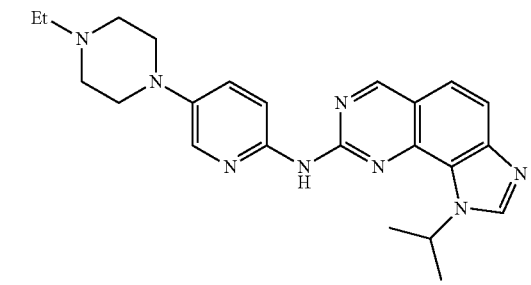 [SMILES: CCN1CCN(c2ccc(Nc3ncc4ccc5ncn(C(C)C)c5c4n3)nc2)CC1] | I-5 |
| 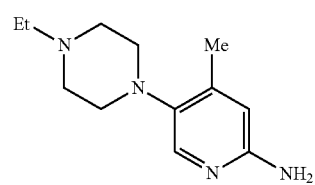 [SMILES: CCN1CCN(c2cnc(N)cc2C)CC1] | 10f | 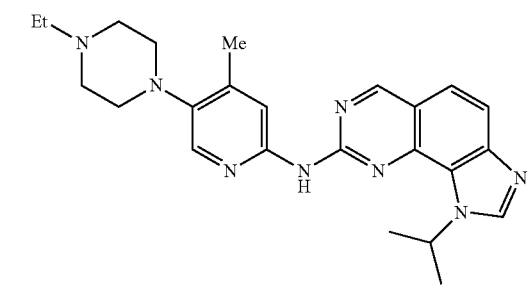 [SMILES: CCN1CCN(c2cnc(Nc3ncc4ccc5ncn(C(C)C)c5c4n3)cc2C)CC1] | I-6 |
| 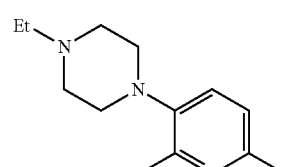 | 10g | 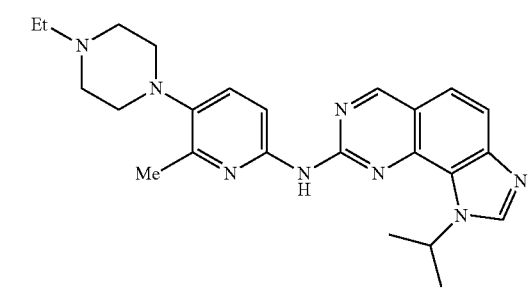 [SMILES: CCN1CCN(c2ccc(Nc3ncc4ccc5ncn(C(C)C)c5c4n3)nc2C)CC1] | I-7 |
| 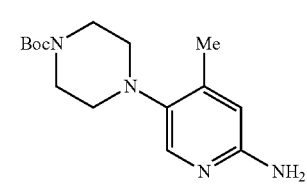 | 10h | 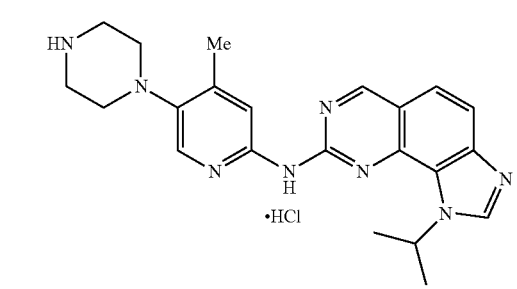 [SMILES: Cc1cc(Nc2ncc3ccc4ncn(C(C)C)c4c3n2)ncc1N1CCNCC1 ; Cl] | I-8 |
| 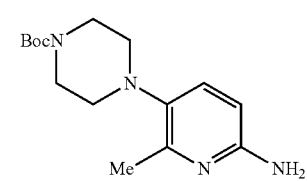 [SMILES: Cc1nc(N)ccc1N1CCN(C(=O)OC(C)(C)C)CC1] | 10i | 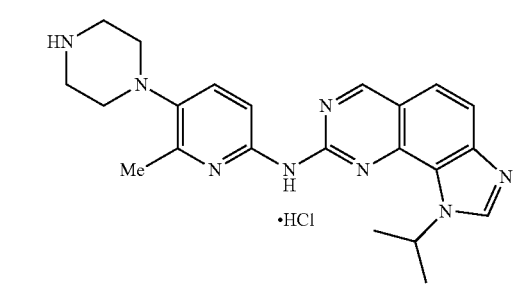 [SMILES: Cc1nc(Nc2ncc3ccc4ncn(C(C)C)c4c3n2)ccc1N1CCNCC1 ; Cl] | I-9 |

TABLE 1-continued

Examples I-3 to I-41

| Side chains | | Products | |
|---|---|---|---|
| [structure] | 10j | [structure] | I-10 |
| [structure] | 10k | [structure] | I-11 |
| [structure] | 10l | [structure] | I-12 |
| [structure] | 10m | [structure] | I-13 |
| [structure] | 10n | [structure] | I-14 |

TABLE 1-continued

Examples I-3 to I-41

| Side chains | | Products | |
|---|---|---|---|
| (structure) | 10o | (structure) | I-15 |
| (structure) | 10p | (structure) | I-16 |
| (structure) | 10q | (structure) | I-17 |
| (structure) | 10r | (structure) | I-18 |
| (structure) | 10s | (structure) | I-19 |

TABLE 1-continued

Examples I-3 to I-41

| Side chains | Products |
|---|---|
| 10t | I-20 |
| 10u | I-21 |
| 10v | I-22 |
| 10w | I-23 |
| 10x | I-24 |

TABLE 1-continued

Examples I-3 to I-41

| Side chains | | Products | |
|---|---|---|---|
| (structure) | 10y | (structure) | I-25 |
| (structure) | 10z | (structure) | I-26 |
| (structure) | 10za | (structure) | I-27 |
| (structure) | 10zb | (structure) ·HCl | I-28 |
| (structure) | 10zc | (structure) ·HCl | I-29 |

TABLE 1-continued

Examples I-3 to I-41

| Side chains | | Products | |
|---|---|---|---|
| [structure] | 10zd | [structure] ·HCl | I-30 |
| [structure] | 10ze | [structure] ·HCl | I-31 |
| [structure] | 10zf | [structure] ·HCl | I-32 |
| [structure] | 10zg | [structure] | I-33 |
| [structure] | 10zh | [structure] | I-34 |

TABLE 1-continued
Examples I-3 to I-41
| Side chains | | Products | |
|---|---|---|---|
| 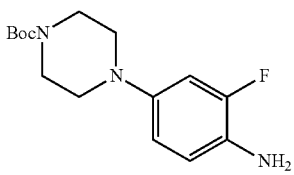 [SMILES: CC(C)(C)OC(=O)N1CCN(c2ccc(N)c(F)c2)CC1] | 10zi | 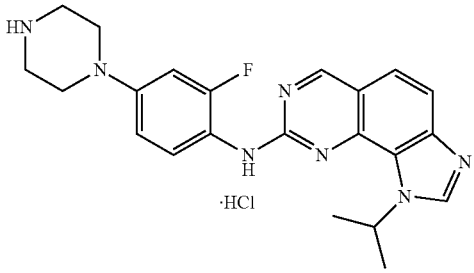 [SMILES: CC(C)n1cnc2ccc3cnc(Nc4ccc(N5CCNCC5)cc4F)nc3c21] | I-35 |
| 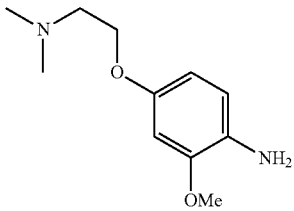 | 10zj | 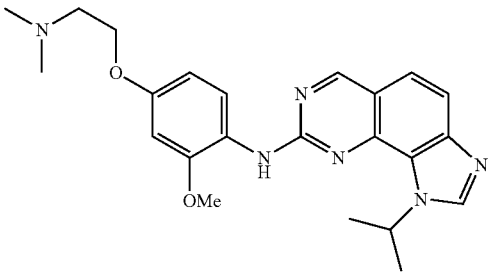 [SMILES: COc1cc(OCCN(C)C)ccc1Nc1ncc2ccc3ncn(C(C)C)c3c2n1] | I-36 |
| 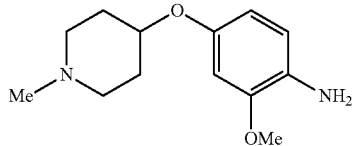 [SMILES: COc1cc(OC2CCN(C)CC2)ccc1N] | 10zk | 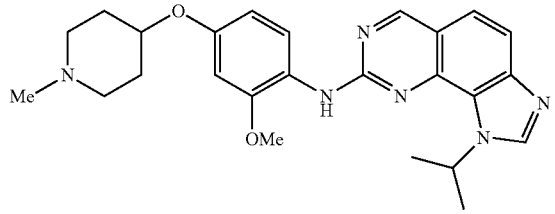 [SMILES: COc1cc(OC2CCN(C)CC2)ccc1Nc1ncc2ccc3ncn(C(C)C)c3c2n1] | I-37 |
| 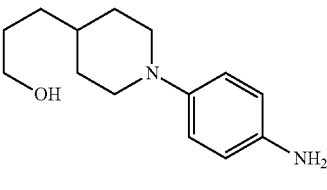 [SMILES: Nc1ccc(N2CCC(CCCO)CC2)cc1] | 10zl | 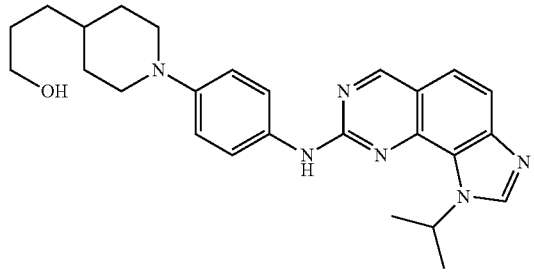 [SMILES: CC(C)n1cnc2ccc3cnc(Nc4ccc(N5CCC(CCCO)CC5)cc4)nc3c21] | I-38 |
| 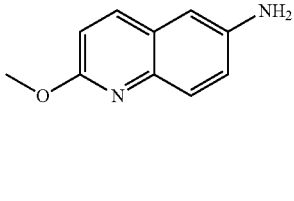 | 10zm | 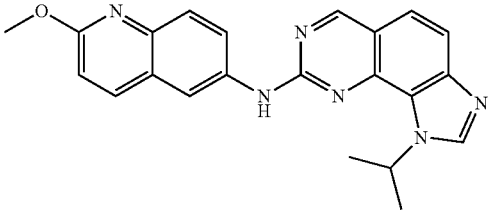 [SMILES: COc1ccc2cc(Nc3ncc4ccc5ncn(C(C)C)c5c4n3)ccc2n1] | I-39 |

TABLE 1-continued

Examples I-3 to I-41

| Side chains | Products |
|---|---|
| 10zn (Me-N-piperidine-NH-C(O)-phenyl(OMe)(NH2)) | I-40 |
| 10zo (isopropyl-piperazine-pyridazine-NH2) | I-41 |

By referring to the synthetic method of I-2 in Example 2, compounds I-3 (8.7 mg, 20.9 μmmol, 19%), I-4 (10.5 mg, 25.3 μmmol, 23%), I-5 (11.9 mg, 28.6 μmmol, 26%), I-6 (9.9 mg, 23.1 μmmol, 21%), I-7 (8.5 mg, 19.8 μmmol, 18%), I-15 (5.2 mg, 12.1 μmmol, 11%), I-16 (12.3 mg, 31.9 μmmol, 29%), I-17 (5.8 mg, 14.3 μmmol, 13%), I-18 (5.4 mg, 12.1 μmmol, 11%), I-19 (5.2 mg, 12.1 μmmol, 11%), I-20 (5.9 mg, 13.2 μmmol, 12%), I-23 (13.3 mg, 34.1 μmmol, 31%), I-24 (6.6 mg, 16.5 μmmol, 11%), I-25 (xx mg, 27.5 μmmol, 12%), I-26 (12.0 mg, 29.7 μmmol, 27%), I-27 (19.7 mg, 31.9 μmmol, 29%), I-33 (9.0 mg, 11.1 μmmol, 10%), I-34 (3.3 mg, 7.7 μmmol, 7%), I-36 (3.7 mg, 8.8 μmmol, 29%), I-37 (5.4 mg, 12.1 μmmol, 11%), I-38 (5.4 mg, 12.1 μmmol, 11%), I-39 (8.0 mg, 20.9 μmmol, 19%), I-40 (5.4 mg, 7.7 μmmol, 7%), and I-41 (4.3 mg, 9.9 μmmol, 9%) were prepared from 9a (30 mg, 0.11 mmol) and 10 (0.22 mmol, 2 equiv.).

I-3 LC-MS (ESI), $C_{24}H_{29}N_8$ [M+H]$^+$: m/z=417.1.

I-4 LC-MS (ESI), $C_{24}H_{29}N_8$ [M+H]$^+$: m/z=4317.2.

I-5 $^1$H NMR (400 MHz, chloroform-d) δ 9.17 (s, 1H), 8.28 (d, J=9.0 Hz, 1H), 8.25 (s, 1H), 8.21 (s, 1H) 8.09 (d, J=2.9 Hz, 1H), 7.74 (d, J=8.6 Hz, 1H), 7.56 (d, J=8.6 Hz, 1H) 7.34 (dd, J=9.1, 3.0 Hz, 1H), 6.07 (p, J=6.8 Hz, 1H), 3.24 (t, J=5.0 Hz, 4H), 2.68 (t, J=5.0 Hz, 4H), 2.52 (q, J=7.2 Hz 2H), 2.51 (s, 3H), 1.73 (d, J=6.8 Hz, 6H), 1.16 (t, J=7.2 Hz, 3H).

I-6 $^1$H NMR (400 MHz, chloroform-d, ppm) δ 9.19 (s, 1H) 8.39 (s, 1H), 8.21 (d, J=9.2 Hz, 2H), 8.11 (s, 1H), 7.75 (d, J=8.6 Hz, 1H), 7.57 (d, J=8.6 Hz, 1H), 6.10 (dt, J=13.4, 6.7 Hz, 1H), 3.08 (t, J=4.4 Hz, 4H), 2.70 (s, 4H), 2.57 (q, J=7.2 Hz, 2H), 2.41 (s, 3H), 1.73 (d, J=6.7 Hz, 6H), 1.18 (t, J=7.2 Hz, 3H).

I-7 $^1$H NMR (400 MHz, chloroform-d, ppm) δ 9.21 (s, 1H), 8.35-8.09 (m, 3H), 7.73 (d, J=8.6 Hz, 1H), 7.55 (d, J=8.6 Hz, 1H), 7.42 (d, J=8.7 Hz, 1H), 6.07 (dt, J=13.4, 6.7 Hz, 1H), 2.99 (t, J=4.5 Hz, 4H), 2.67 (s, 4H), 2.59-2.44 (m, 5H), 1.71 (d, J=6.7 Hz, 6H), 1.16 (t, J=7.2 Hz, 3H).

I-15 LC-MS (ESI), $C_{23}H_{29}N_8O$ [M+H]$^+$: m/z=433.1.

I-16 $^1$H NMR (400 MHz, chloroform-d, ppm) δ 9.20 (s, 1H), 8.62 (s, 1H), 8.26 (d, J=9.0 Hz, 1H), 8.20 (s, 1H), 8.16-8.05 (m, 1H), 7.73 (d, J=8.6 Hz, 1H), 7.55 (d, J=8.6 Hz, 1H), 7.34 (dd, J=9.0, 2.5 Hz, 1H), 6.08 (dt, J=13.5, 6.7 Hz, 1H), 3.37-2.90 (m, 4H), 1.76 (m, 4H), 1.74 (d, J=6.7 Hz, 6H), 1.60 (dt, J=11.2, 5.8 Hz, 2H).

I-17 LC-MS (ESI), $C_{22}H_{26}N_7O$ [M+H]$^+$: m/z=404.2.

I-18 LC-MS (ESI), $C_{25}H_{32}N_7O$ [M+H]$^+$: m/z=446.3.

I-19 $^1$H NMR (400 MHz, chloroform-d, ppm) δ 9.23 (s, 1H), 8.51 (s, 1H), 8.05-7.89 (m, 2H), 7.73-7.60 (m, 3H), 5.93 (p, J=6.8 Hz, 1H), 3.83 (d, J=12.5 Hz, 2H), 3.39 (t, J=12.2 Hz, 1H), 2.92 (s, 6H), 2.84 (m, 2H), 2.26 (d, J=12.2 Hz, 2H), 1.89 (qd, J=12.5, 4.2 Hz, 2H), 1.67 (d, J=6.7 Hz, 6H).

I-20 LC-MS (ESI), $C_{24}H_{30}FN_8$ [M+H]$^+$: m/z=449.3.

I-23 $^1$H NMR (400 MHz, chloroform-d, ppm) δ 9.19 (s, 1H), 8.42 (s, 1H), 8.31 (d, J=9.0 Hz, 1H), 8.21 (s, 1H), 8.09 (d, J=2.9 Hz, 1H), 7.74 (d, J=8.6 Hz, 1H), 7.56 (d, J=8.6 Hz, 1H), 7.32 (dd, J=9.0, 3.0 Hz, 1H), 6.07 (p, J=6.8 Hz, 1H), 3.98-3.81 (m, 4H), 3.19-3.10 (m, 4H), 1.73 (d, J=6.7 Hz, 6H).

I-24 $^1$H NMR (400 MHz, chloroform-d, ppm) δ 9.17 (s, 1H), 8.22 (s, 2H), 8.04 (s, 2H), 7.77 (d, J=8.7 Hz, 1H), 7.58 (d, J=8.3 Hz, 1H), 6.14-6.05 (m, 1H), 3.95-3.78 (m, 4H), 3.05-2.87 (m, 4H), 2.43 (s, 3H), 1.74 (d, J=6.7 Hz, 6H).

I-25 $^1$H NMR (400 MHz, chloroform-d, ppm) δ 9.18 (s, 1H), 8.31-8.14 (m, 2H), 8.07 (s, 1H), 7.75 (d, J=8.7 Hz, 1H), 7.56 (d, J=8.6 Hz, 1H), 7.40 (d, J=8.7 Hz, 1H), 6.08 (dt, J=13.3, 6.6 Hz, 1H), 4.01-3.76 (m, 4H), 3.04-2.83 (m, 4H), 2.53 (s, 3H), 1.74 (d, J=6.7 Hz, 6H).

I-26 LC-MS (ESI), $C_{22}H_{26}N_7O$ [M+H]$^+$: m/z=404.2.

I-27 $^1$H NMR (400 MHz, chloroform-d, ppm) δ 9.23 (s, 1H), 9.05 (brs, 1H), 8.31 (d, J=9.0 Hz, 1H), 8.22 (s, 1H), 8.11 (d, J=2.9 Hz, 1H), 7.73 (d, J=8.6 Hz, 1H), 7.55 (d, J=8.5 Hz, 1H), 7.31 (dd, J=9.1, 2.9 Hz, 1H), 6.07 (p, J=6.7 Hz, 1H), 3.85 (dqd, J=12.4, 6.1, 2.2 Hz, 2H), 3.49-3.32 (m, 2H), 2.47 (dd, J=11.6, 10.2 Hz, 2H), 1.73 (d, J=6.7 Hz, 6H), 1.29 (s, 3H). 1.28 (s, 3H).

I-33 LC-MS (ESI), $C_{25}H_{29}N_8O$ [M+H]$^+$: m/z=457.1.

I-34 LC-MS (ESI), $C_{24}H_{30}N_7O$ [M+H]$^+$: m/z=432.2.

I-36 LC-MS (ESI), $C_{23}H_{29}N_6O_2$ [M+H]$^+$: m/z=421.1.

I-37 LC-MS (ESI), $C_{25}H_{31}N_6O_2$ [M+H]$^+$: m/z=447.3.

I-38 LC-MS (ESI), $C_{26}H_{33}N_6O$ [M+H]$^+$: m/z=445.2.

I-39 $^1$H NMR (400 MHz, chloroform-d, ppm) δ 9.13 (s, 1H), 8.22 (s, 1H), 8.07 (d, J=2.1 Hz, 1H), 7.97-7.82 (m, 3H), 7.74 (d, J=8.6 Hz, 1H), 7.56 (d, J=8.6 Hz, 2H), 6.94 (d, J=8.8 Hz, 1H), 6.11 (hept, J=7.1, 6.5 Hz, 1H), 4.09 (s, 3H), 1.69 (d, J=6.7 Hz, 6H).

I-40 LC-MS (ESI), $C_{26}H_{32}N_7O_2$ [M+H]$^+$: m/z=474.3.

I-41 LC-MS (ESI), $C_{23}H_{30}N_9$[M+H]$^+$: m/z=432.1.

By referring to the synthetic method of I-1 in Example 1, compounds I-8 (12.5 mg, 28.6 μmmol, 26%), I-9 (15.9 mg, 36.3 μmmol, 33%), I-10 (10.6 mg, 24.2 μmmol, 22%), I-11 (11.4 mg, 25.3 μmmol, 23%), I-12 (10.4 mg, 23.1 μmmol, 21%), I-13 (7.8 mg, 17.6 μmmol, 16%), I-14 (9.2 mg, 20.9 μmmol, 19%), I-21 (5.3 mg, 12.1 μmmol, 11%), I-22 (6.1 mg, 14.3 μmmol, 13%), I-28 (8.9 mg, 18.7 μmmol, 17%), I-29 (4.5 mg, 9.9 μmmol, 9%), I-30 (6.7 mg, 15.4 μmmol, 14%), I-31 (6.6 mg, 14.3 μmmol, 13%), I-32 (5.6 mg, 12.1 μmmol, 11%), and I-35 (6.3 mg, 14.3 μmmol, 13%) were prepared from 9a (30 mg, 0.11 mmol) and 10 (0.22 mmol, 2 equiv.).

I-8 $^1$H NMR (400 MHz, water-d$_2$, ppm) δ 9.73 (s, 1H), 9.68 (s, 1H), 8.22 (d, J=8.9 Hz, 1H), 8.07 (s, 1H), 7.88 (d, J=8.9 Hz, 1H), 7.52 (s, 1H), 6.21 (p, J=6.7 Hz, 1H), 3.24 (m, 4H), 3.21-3.14 (m, 4H), 2.52 (s, 3H), 1.74 (d, J=6.5 Hz, 6H).

I-9a $^1$H NMR (400 MHz, chloroform-d, ppm) δ 9.19 (s, 1H), 8.21 (s, 1H), 8.18 (d, J=8.7 Hz, 1H), 8.13 (d, J=4.2 Hz, 1H), 7.75 (d, J=8.7 Hz, 1H), 7.56 (d, J=8.7 Hz, 1H), 7.37 (d, J=8.7 Hz, 1H), 6.07 (p, J=6.7 Hz, 1H), 3.60 (t, J=4.9 Hz, 4H), 2.87 (d, J=5.0 Hz, 4H), 2.52 (s, 3H), 1.73 (d, J=6.7 Hz, 6H), 1.50 (s, 9H).

I-9 LC-MS (ESI), $C_{22}H_{27}N_8$[M+H]$^+$: m/z=403.1.

I-10 LC-MS (ESI), $C_{22}H_{27}N_8$[M+H]$^+$: m/z=403.2.

I-11 LC-MS (ESI), $C_{23}H_{29}N_8$[M+H]$^+$: m/z=417.3.

I-12 $^1$H NMR (400 MHz, water-d$_2$, ppm) δ 9.56 (s, 1H), 9.43 (s, 1H), 8.12 (t, J=9.3 Hz, 2H), 7.89-7.77 (m, 2H), 7.52 (d, J=9.7 Hz, 1H), 6.00 (dt, J=13.2, 6.7 Hz, 1H), 3.89 (d, J=11.5 Hz, 2H), 3.58 (d, J=6.7 Hz, 2H), 2.98-2.84 (m, 2H), 1.77 (d, J=6.7 Hz, 6H), 1.41 (d, J=6.6 Hz, 6H).

I-13 LC-MS (ESI), $C_{21}H_{24}FN_8$ [M+H]$^+$: m/z=407.1.

I-14a $^1$H NMR (400 MHz, chloroform-d, ppm) δ 9.14 (s, 1H), 8.26-8.13 (m, 2H), 8.01 (s, 1H), 7.90 (s, 1H), 7.72 (d, J=8.6 Hz, 1H), 7.54 (d, J=8.6 Hz, 1H), 7.09 (d, J=9.1 Hz, 1H), 6.08 (dt, J=13.3, 6.7 Hz, 1H), 3.60 (d, J=12.5 Hz, 6H), 3.37 (s, 1H), 3.27 (t, J=5.9 Hz, 1H), 2.01 (d, J=5.8 Hz, 2H), 1.72 (d, J=6.8 Hz, 6H), 1.41 (d, J=21.7 Hz, 9H).

I-14 LC-MS (ESI), $C_{22}H_{27}N_8$[M+H]$^+$: m/z=403.3.

I-21 LC-MS (ESI), $C_{22}H_{27}N_8$[M+H]$^+$: m/z=403.2.

I-22 LC-MS (ESI), $C_{21}H_{25}N_8$[M+H]$^+$: m/z=389.2.

I-28a $^1$H NMR (400 MHz, chloroform-d, ppm) δ 9.16 (s, 1H), 8.93 (brs, 1H), 8.29 (d, J=9.1 Hz, 1H), 8.22 (s, 1H), 7.73 (d, J=8.5 Hz, 1H), 7.62 (d, J=2.9 Hz, 1H), 7.55 (d, J=8.6 Hz, 1H), 7.02 (dd, J=9.2, 2.8 Hz, 1H), 6.08 (p, J=6.7 Hz, 1H), 3.57-3.34 (m, 8H), 1.94 (t, J=6.9 Hz, 2H), 1.73 (d, J=6.7 Hz, 4H), 1.69-1.53 (m, 6H), 1.47 (s, 9H).

I-28 LC-MS (ESI), $C_{25}H_{31}N_8$[M+H]$^+$: m/z=443.2.

I-29 LC-MS (ESI), $C_{23}H_{27}N_8$[M+H]$^+$: m/z=415.3.

I-30a $^1$H NMR (400 MHz, chloroform-d) δ 9.18 (s, 1H), 8.96 (brs, 1H), 8.41-8.24 (m, 2H), 7.82-7.72 (m, 1H), 7.64-7.50 (m, 2H), 6.95 (d, J=8.7 Hz, 1H), 6.06 (p, J=6.8 Hz, 1H), 4.13 (s, 4H), 4.03 (s, 4H), 1.73 (dd, J=6.8, 1.7 Hz, 6H), 1.45 (s, 9H).

I-30 LC-MS (ESI), $C_{22}H_{25}N_8$[M+H]$^+$: m/z=401.1.

I-31a $^1$H NMR (400 MHz, chloroform-d, ppm) δ 9.15 (s, 1H), 8.28 (d, J=9.0 Hz, 1H), 8.21 (s, 1H), 8.04 (d, J=2.8 Hz, 1H), 7.94 (s, 1H), 7.74 (d, J=8.7 Hz, 1H), 7.56 (d, J=8.6 Hz, 1H), 7.34 (dd, J=9.1, 2.9 Hz, 1H), 6.07 (p, J=6.8 Hz, 1H), 3.71 (s, 4H), 3.10 (t, J=5.5 Hz, 4H), 1.94 (t, J=5.5 Hz, 4H), 1.73 (d, J=6.7 Hz, 6H), 1.46 (s, 9H).

I-31 LC-MS (ESI), $C_{24}H_{29}N_8$[M+H]$^+$: m/z=429.2.

I-32a $^1$H NMR (400 MHz, chloroform-d) δ 9.15 (s, 1H), 8.20 (t, J=4.4 Hz, 2H), 8.11 (s, 1H), 7.72 (d, J=8.6 Hz, 1H), 7.66 (d, J=2.9 Hz, 1H), 7.54 (d, J=8.7 Hz, 1H), 6.86 (dd, J=8.8, 2.9 Hz, 1H), 6.07 (p, J=6.7 Hz, 1H), 3.69 (s, 4H), 3.41 (d, J=5.8 Hz, 4H), 1.82 (t, J=5.7 Hz, 8H), 1.72 (d, J=6.7 Hz, 6H), 1.47 (s, 9H).

I-32 LC-MS (ESI), $C_{24}H_{29}N_8$[M+H]$^+$: m/z=429.1.

I-35a $^1$H NMR (400 MHz, chloroform-d) δ 9.10 (s, 1H), 8.18 (s, 1H), 8.13 (t, J=9.2 Hz, 1H), 7.71 (d, J=8.4 Hz, 1H), 7.53 (d, J=8.4 Hz, 1H), 7.19 (s, 1H), 6.74 (m, 2H), 5.97 (p, J=6.7 Hz, 1H), 3.61 (m, 4H), 3.13 (m, 4H), 1.66 (d, J=6.7 Hz, 6H), 1.50 (s, 9H).

I-35 LC-MS (ESI), $C_{22}H_{25}FN_7$ [M+H]$^+$: m/z=406.2.

Preparation of the Key Intermediate 1-ethyl-8-(methylsulfinyl)-1H-imidazo[4,5-h]quinazoline (9b)

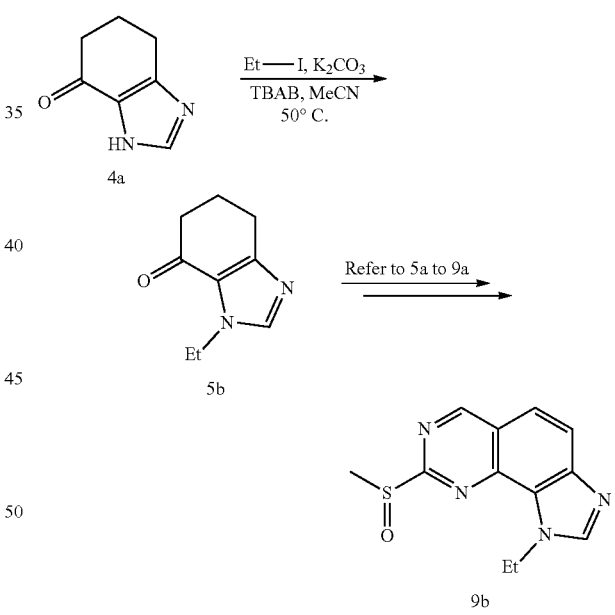

1): By referring to the synthetic method of 5a in Example 1, 3-ethyl-3,5,6,7-tetrahydrogen-4H-benzo[d]imidazol-4-one (5b, 3.05 g, 18.6 mmol, 23%) was obtained from reaction of the compound 4a (11.0 g, 80.9 mmol). LC-MS (ESI), $C_9H_{13}N_2O$ [M+H]$^+$: m/z=165.3.

2): By referring to the synthetic steps of 5a to 9a in Example 1, the title compound (9b, 523 mg, 2.0 mmol, yield of four steps: 11%) was prepared from 5b (3.0 g, 18.3 mmol) via four reaction steps. $^1$H NMR (400 MHz, chloroform-d) δ 9.54 (s, 1H), 8.21 (s, 1H), 8.15 (d, J=8.7 Hz, 1H), 7.83 (d, J=8.7 Hz, 1H), 5.05-4.88 (m, 2H), 3.06 (s, 3H), 1.69 (t, J=7.3 Hz, 3H).

TABLE 2

Examples I-42 to I-46

| Side chains | Products |
|---|---|
| 10a | I-42 |
| 10b | I-43 |
| 10za | I-44 |
| 10w | I-45 |
| 11z | I-46 |

By referring to the synthetic method of I-1 in Example 1, the title compound I-42 (11.1 mg, 27.2 μmmol, 24%) was prepared from 9b (30 mg, 0.115 mmol).

I-42a ¹H NMR (400 MHz, chloroform-d, ppm) δ 9.17 (s, 1H), 8.36 (d, J=9.0 Hz, 1H), 8.17 (s, 1H), 8.07 (d, J=2.9 Hz, 1H), 8.05 (s, 1H), 7.74 (d, J=8.6 Hz, 1H), 7.57 (d, J=8.6 Hz, 1H), 7.36 (dd, J=9.0, 3.0 Hz, 1H), 4.90 (q, J=7.2 Hz, 2H), 3.63 (t, J=5.0 Hz, 4H), 3.12 (t, J=5.1 Hz, 4H), 1.70-1.62 (t, J=7.2 Hz, 3H), 1.50 (s, 9H).

I-42 LC-MS (ESI), $C_{20}H_{23}N_8[M+H]^+$: m/z=375.2.

By referring to the synthetic method of I-2 in Example 2, compounds I-43 (13.4 mg, 34.5 μmmol, 30%), I-44 (11.6 mg, 28.7 μmmol, 25%), I-45 (13.0 mg, 34.5 μmmol, 33%), and I-46 (10.3 mg, 26.5 μmmol, 23%) were prepared from 9b (30 mg, 0.115 mmol).

I-43 ¹H NMR (400 MHz, methanol-d₄, ppm) δ 9.03 (s, 1H), 8.19 (d, J=9.0 Hz, 1H), 7.99 (s, 1H), 7.88 (d, J=3.0 Hz, 1H), 7.56 (d, J=8.7 Hz, 1H), 7.48 (d, J=8.7 Hz, 1H), 7.29 (dd, J=9.1, 3.0 Hz, 1H), 4.79 (q, J=7.2 Hz, 2H), 3.11 (t, J=5.0 Hz, 4H), 2.55 (t, J=5.0 Hz, 4H), 2.27 (s, 3H), 1.53 (t, J=7.2 Hz, 3H).

I-44 ¹H NMR (400 MHz, chloroform-d:methanol-d₄=1:1, ppm) δ 8.34 (d, J=9.1 Hz, 1H), 8.20 (s, 1H), 8.10-8.02 (m, 2H), 7.74 (d, J=8.7 Hz, 1H), 7.56 (d, J=8.7 Hz, 1H), 7.33 (dd, J=9.0, 3.0 Hz, 1H), 4.90 (q, J=7.2 Hz, 2H), 3.86 (dtt, J=12.6, 6.4, 4.0 Hz, 2H), 3.44-3.35 (m, 2H), 2.47 (t, J=10.9 Hz, 2H), 1.72-1.60 (t, J=7.2 Hz, 6H), 1.29 (d, J=6.2 Hz, 6H).

I-45 ¹H NMR (400 MHz, chloroform-d, ppm) δ 9.17 (s, 1H), 8.36 (d, J=9.0 Hz, 1H), 8.17 (s, 1H), 8.07 (d, J=2.9 Hz, 1H), 8.05 (s, 1H), 7.74 (d, J=8.6 Hz, 1H), 7.57 (d, J=8.7 Hz, 1H), 7.35 (dd, J=9.1, 3.0 Hz, 1H), 4.90 (q, J=7.2 Hz, 2H), 3.95-3.84 (m, 4H), 3.21-3.12 (m, 4H), 1.65 (t, J=7.0 Hz, 3H).

I-46 LC-MS (ESI), $C_{21}H_{24}N_7O [M+H]^+$: m/z=390.1.

Preparation of the Key Intermediate 1-cyclopropyl-8-(methylsulfinyl)-1H-imidazo[4,5-h]quinazoline (9c)

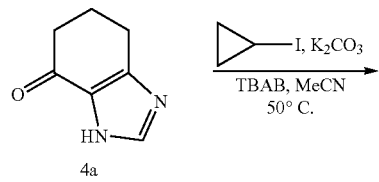

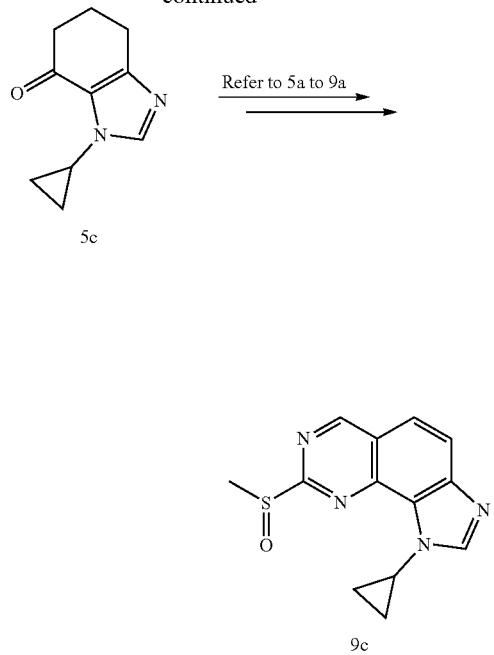

1): By referring to the synthetic method of 5a in Example 1, the compound 3-cyclopropyl-3,5,6,7-tetrahydrogen-4H-benzo[d]imidazol-4-one (5c, 2.2 g, 12.6 mmol, 19%) was prepared from compound 4a (9 g, 66.2 mmol). ¹H NMR (600 MHz, chloroform-d, ppm) δ 7.48 (s, 1H), 3.53 (dt, J=7.3, 3.5 Hz, 1H), 2.73 (t, J=6.2 Hz, 2H), 2.43 (dd, J=7.2, 5.8 Hz, 2H), 2.07-1.96 (m, 2H), 1.07-0.94 (m, 2H), 0.88-0.77 (m, 2H).

2): By referring to the synthetic steps of 5a to 9a in Example 1, 9c (490 mg, 1.8 mmol, 16%) was prepared from 5c (2.0 g, 11.4 mmol) via four reaction steps. ¹H NMR (400 MHz, chloroform-d, ppm) δ 9.54 (d, J=1.1 Hz, 1H), 8.20 (s, 1H), 8.12 (dd, J=8.7, 1.1 Hz, 1H), 7.83 (dd, J=8.8, 1.1 Hz, 1H), 4.16 (tt, J=7.5, 4.0 Hz, 1H), 3.06 (d, J=1.1 Hz, 3H), 1.48-1.36 (m, 2H), 1.20 (qd, J=10.5, 3.9 Hz, 2H).

TABLE 3

| Examples I-47 to I-51 |
| --- |

| Side chains | Products |
| --- | --- |

TABLE 3-continued

Examples I-47 to I-51

| Side chains | Products |
|---|---|
| 10h | I-48 (·HCl) |
| 10w | I-49 |
| 10x | I-50 |
| 10y | I-51 |

By referring to the synthetic method of I-1 in Example 1, the title compounds I-47 (9.7 mg, 23.1 μmmol, 21%), and I-48 (11.5 mg, 28.6 μmmol, 26%) were prepared from 9c (30 mg, 0.11 mmol).

I-47a $^1$H NMR (600 MHz, methanol-$d_4$, ppm) δ 9.19 (s, 1H), 8.48 (d, J=9.0 Hz, 1H), 8.26 (d, J=3.4 Hz, 1H), 7.99 (d, J=2.9 Hz, 1H), 7.74 (dt, J=6.9, 2.2 Hz, 1H), 7.68-7.59 (m, 2H), 7.45 (d, J=8.7 Hz, 1H), 4.49 (d, J=5.1 Hz, 1H), 3.60 (m, 4H), 3.13 (t, J=5.1 Hz, 4H), 1.48 (s, 9H), 1.31-1.23 (m, 2H), 1.22 (d, J=4.3 Hz, 2H).

I-47 LC-MS (ESI), $C_{21}H_{23}N_8[M+H]^+$: m/z=387.1.

I-48a $^1$H NMR (400 MHz, chloroform-d, ppm) δ 9.19 (s, 1H), 8.49 (s, 1H), 8.25 (s, 1H), 8.06 (s, 1H), 8.03 (s, 1H), 7.74 (d, J=8.6 Hz, 1H), 7.58 (d, J=8.6 Hz, 1H), 4.28 (tt, J=7.4, 4.0 Hz, 1H), 3.59 (t, J=4.9 Hz, 4H), 2.92 (t, J=4.9 Hz, 4H), 2.29 (s, 3H), 1.33-1.26 (m, 2H), 1.20 (dt, J=5.1, 2.2 Hz, 2H).

I-48 LC-MS (ESI), $C_{22}H_{25}N_8[M+H]^+$: m/z=401.3.

By referring to the synthetic method of I-2 in Example 2, compounds I-49 (9.8 mg, 25.3 μmmol, 23%), I-50 (9.3 mg, μmmol, 21%), and I-51 (12.8 mg, 31.9 μmmol, 29%) were prepared from 9c (30 mg, 0.11 mmol).

I-49 $^1$H NMR (400 MHz, chloroform-d/methanol-$d_4$=1:1, ppm) δ 9.11 (d, J=2.3 Hz, 1H), 8.48 (dd, J=9.1, 2.7 Hz, 1H), 8.04 (s, 1H), 7.93 (t, J=3.0 Hz, 1H), 7.62 (dd, J=8.6, 3.4 Hz, 1H), 7.54 (dd, J=8.6, 2.2 Hz, 1H), 7.24 (dt, J=9.1, 2.2 Hz, 1H), 4.17 (dq, J=7.2, 3.4 Hz, 1H), 3.90-3.79 (m, 4H), 3.10 (t, J=3.4 Hz, 4H), 1.36-1.21 (m, 2H), 1.21-1.10 (m, 2H).

I-50 ¹H NMR (400 MHz, chloroform-d, ppm) δ 9.19 (s, 1H), 8.48 (s, 1H), 8.11 (s, 1H), 7.99 (s, 1H), 7.77-7.67 (m, 1H), 7.62 (d, J=8.6 Hz, 1H), 7.33 (s, 1H), 4.29 (tt, J=7.4, 4.0 Hz, 1H), 3.88 (t, J=4.5 Hz, 4H), 2.98 (t, J=4.5 Hz, 4H), 2.30 (s, 3H), 1.31 (d, J=7.0 Hz, 2H), 1.28-1.17 (m, 2H).

I-51 ¹H NMR (400 MHz, chloroform-d/methanol-d₄=1:1, ppm) δ 9.14 (s, 1H), 8.40 (d, J=8.7 Hz, 1H), 8.05 (s, 1H), 7.67 (d, J=8.6 Hz, 1H), 7.56 (d, J=8.6 Hz, 1H), 7.32 (d, J=8.7 Hz, 1H), 4.22 (dd, J=7.3, 3.9 Hz, 1H), 3.84 (t, J=4.5 Hz, 4H), 2.87 (t, J=4.6 Hz, 4H), 2.49 (s, 3H), 1.30 (d, J=6.9 Hz, 2H), 1.18 (tt, J=7.5, 4.5 Hz, 2H).

Preparation of the Key Intermediate 1-cyclobutyl-8-(methylsulfinyl)-1H-imidazo[4,5-h]quinazoline (9d)

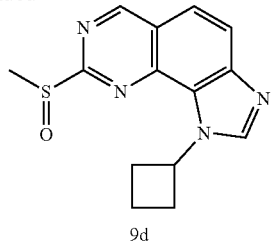

9d

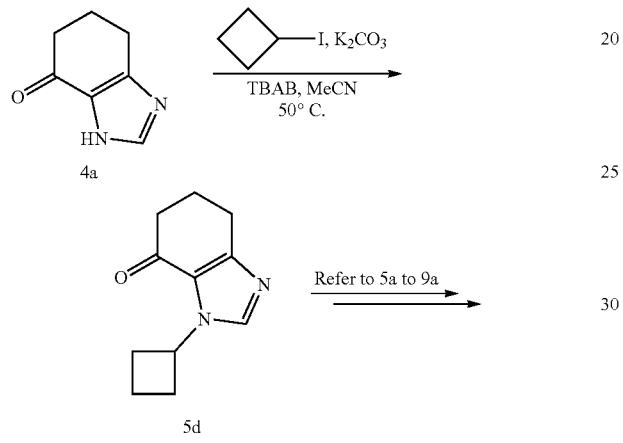

1): By referring to the synthetic method of 5a in Example 1, the compound 3-cyclobutyl-3,5,6,7-tetrahydrogen-4H-benzo[d]imidazol-4-one (5d, 1.56 g, 8.23 mmol, 14%) was obtained from reaction of compound 4a (8 g, 58.8 mmol). LC-MS (ESI) for $C_{11}H_{15}N_2O$ [M+H]⁺: m/z=191.3.

2): By referring to the synthetic steps of 5a to 9a in Example 1, 9d (429 mg, 1.5 mmol, 19%) was prepared from 5d (1.5 g, 7.89 mmol) via four reaction steps. ¹H NMR (400 MHz, chloroform-d, ppm) δ 9.51 (d, J=1.0 Hz, 1H), 8.38 (s, 1H), 8.14 (d, J=8.7 Hz, 1H), 7.82 (d, J=8.7 Hz, 1H), 5.88 (p, J=8.5 Hz, 1H), 3.05 (d, J=1.0 Hz, 3H), 2.96-2.85 (m, 2H), 2.55 (pd, J=9.9, 4.1 Hz, 2H), 2.19-1.97 (m, 2H).

TABLE 4

Examples I-52 to I-56

| Side chains | Products | |
|---|---|---|
| [structure 10a: BocN-piperazine-pyridine-NH₂] | [structure I-52: HN-piperazine-pyridine-NH-imidazoquinazoline-cyclobutyl ·HCl] | I-52 |
| [structure 10h: BocN-piperazine-(Me)pyridine-NH₂] | [structure I-53: HN-piperazine-(Me)pyridine-NH-imidazoquinazoline-cyclobutyl ·HCl] | I-53 |

TABLE 4-continued

Examples I-52 to I-56

| Side chains | Products |
|---|---|
| 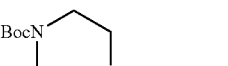 | 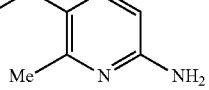 I-54 |
| 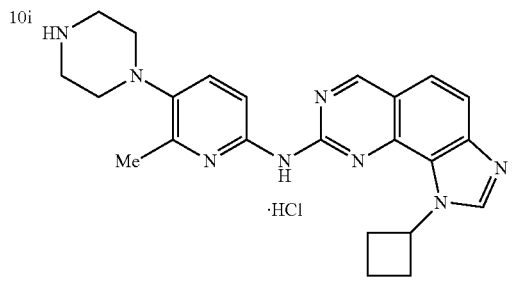 | 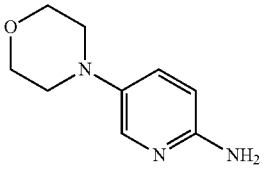 I-55 |
| 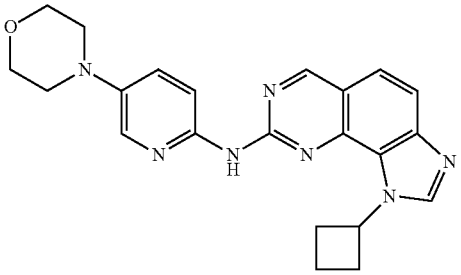 [SMILES: c1cc(Nc2ncc3ccc4ncn(C5CCC5)c4c3n2)ncc1N1CCOCC1] | 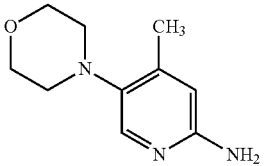 I-56 |

By referring to the synthetic method of I-1 in Example 1, compounds I-52 (11.5 mg, 26.3 μmmol, 25%), I-53 (10.9 mg, 24.2 μmmol, 23%), and I-54 (13.7 mg, 30.5 μmmol, 29%) were prepared from 9d (30 mg, 0.105 mmol).

I-52a $^1$H NMR (400 MHz, chloroform-d, ppm) δ 9.16 (s, 1H), 8.39 (d, J=9.0 Hz, 1H), 8.29 (s, 1H), 8.12 (s, 1H), 8.09 (d, J=2.9 Hz, 1H), 7.74 (d, J=8.6 Hz, 1H), 7.56 (d, J=8.7 Hz, 1H), 7.41 (dd, J=9.0, 2.9 Hz, 1H), 6.16-6.04 (m, 1H), 3.64 (t, J=5.1 Hz, 4H), 3.13 (t, J=5.2 Hz, 4H), 2.74 (tdd, J=9.9, 5.1, 2.5 Hz, 2H), 2.50 (pd, J=9.4, 2.8 Hz, 2H), 2.08-1.90 (m, 2H), 1.50 (s, 9H).

I-52 LC-MS (ESI), $C_{22}H_{25}N_8[M+H]^+$: m/z=401.2.

I-53a $^1$H NMR (400 MHz, chloroform-d, ppm) δ 9.32 (s, 1H), 8.76 (s, 1H), 8.71 (s, 1H), 8.01-7.94 (m, 1H), 7.76 (d, J=8.8 Hz, 1H), 7.72 (s, 1H), 6.18-5.96 (m, 1H), 3.62 (t, J=4.5 Hz, 4H), 2.90 (t, J=4.5 Hz, 4H), 2.58 (s, 3H), 2.54-2.40 (m, 2H), 2.32 (q, J=9.3 Hz, 1H), 2.03 (q, J=10.0 Hz, 1H), 1.50 (d, J=1.7 Hz, 9H).

I-53 LC-MS (ESI), $C_{23}H_{27}N_8[M+H]^+$: m/z=415.3.

I-54a $^1$H NMR (400 MHz, chloroform-d, ppm) δ 9.17 (s, 1H), 8.28 (s, 1H), 8.26 (d, J=8.6 Hz, 1H), 8.06 (s, 1H), 7.73 (d, J=8.7 Hz, 1H), 7.55 (d, J=8.7 Hz, 1H), 7.43 (d, J=8.7 Hz, 1H), 6.16-6.02 (m, 1H), 3.61 (t, J=4.9 Hz, 4H), 2.87 (t, J=4.9 Hz, 4H), 2.74 (qt, J=7.6, 2.6 Hz, 2H), 2.53 (s, 3H), 2.51-2.44 (m, 2H), 1.98 (ddd, J=18.3, 9.1, 2.7 Hz, 2H), 1.50 (s, 9H).

I-54 LC-MS (ESI), $C_{23}H_{27}N_8[M+H]^+$: m/z=415.2.

By referring to the synthetic method of I-2 in Example 2, compounds I-55 (8.9 mg, 22.1 μmmol, 21%), and I-56 (14.4 mg, 34.6 μmmol, 33%) were prepared from 9d (30 mg, 0.105 mmol).

I-55 $^1$H NMR (400 MHz, chloroform-d, ppm) δ 9.16 (s, 1H), 8.39 (d, J=9.0 Hz, 1H), 8.28 (s, 1H), 8.13 (s, 1H), 8.08 (d, J=3.0 Hz, 1H), 7.73 (d, J=8.6 Hz, 1H), 7.56 (d, J=8.7 Hz, 1H), 7.39 (dd, J=9.0, 3.0 Hz, 1H), 6.11 (dq, J=17.1, 8.5, 8.0 Hz, 1H), 3.92 (t, J=4.8 Hz, 4H), 3.18 (t, J=4.8 Hz, 4H), 2.80-2.67 (m, 2H), 2.50 (pd, J=9.6, 2.6 Hz, 2H), 2.07-1.90 (m, 2H).

I-56 $^1$H NMR (400 MHz, chloroform-d, ppm) δ 9.18 (s, 1H), 8.30 (s, 1H), 8.25 (s, 1H), 8.09 (s, 1H), 8.06 (s, 1H), 7.75 (d, J=8.6 Hz, 1H), 7.57 (d, J=8.6 Hz, 1H), 6.08 (p, J=8.5 Hz, 1H), 3.88 (t, J=4.5 Hz, 4H), 3.00 (t, J=4.5 Hz, 4H), 2.85-2.73 (m, 2H), 2.51 (dd, J=9.6, 2.8 Hz, 2H), 2.48 (s, 3H), 1.98 (tt, J=11.0, 8.6 Hz, 2H).

Preparation of the Key Intermediate 1-cyclopentyl-8-(methylsulfinyl)-1H-imidazo[4,5-h]quinazoline (9e)

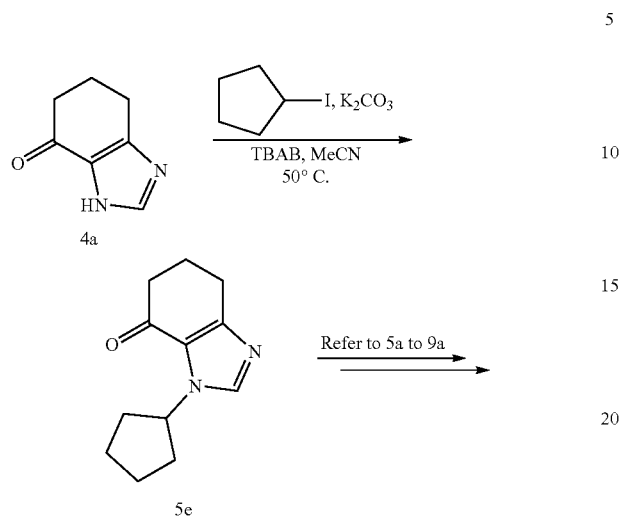

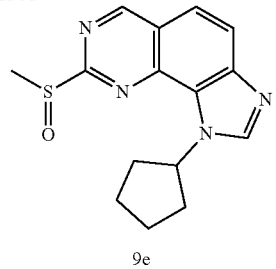

1): By referring to the synthetic method of 5a in Example 1, the title compound 3-cyclopentyl-3,5,6,7-tetrahydrogen-4H-benzo[d]imidazol-4-one (5e, 3.6 g, 17.64 mol, 24%) was prepared from the compound 4a (10.0 g, 73.5 mmol). LC-MS (ESI) for $C_{12}H_{17}N_2O$ [M+H]$^+$: m/z=205.3.

2): By referring to the synthetic steps of 5a to 9a in Example 1, the title compound 9e (594 mg, 1.98 mmol, 13%) was prepared from 5e (3.1 g, 15.2 mmol) via four reaction steps. $^1$H NMR (400 MHz, chloroform-d, ppm) δ 9.53 (s, 1H), 8.32 (s, 1H), 8.15 (d, J=8.7 Hz, 1H), 7.82 (d, J=8.7 Hz, 1H), 6.05 (p, J=6.7 Hz, 1H), 3.05 (d, J=1.1 Hz, 3H), 2.50 (dq, J=13.3, 6.6 Hz, 2H), 2.09 (td, J=13.8, 6.8 Hz, 2H), 1.95 (d, J=8.1 Hz, 4H).

TABLE 5

Examples I-57 to I-61

TABLE 5-continued

Examples I-57 to I-61

| Side chains | Products |
|---|---|
| ![I-57/58/59 side chain: morpholine-pyridine-Me-NH2] | 10x → I-60 [morpholinopyridinyl-Me-NH-imidazoquinazoline with cyclopentyl] |
| ![I-60/61 side chain: morpholine-pyridine-Me-NH2] | 10x → I-61 [morpholinopyridinyl-Me-NH-imidazoquinazoline with cyclopentyl] |

By referring to the synthetic method of I-1 in Example 1, the title compounds I-57 (11.3 mg, 25.0 μmmol, 25%), I-58 (12.1 mg, 26.0 μmmol, 26%), and I-59 (12.5 mg, 27.0 μmmol, 27%) were prepared from 9e (30 mg, 0.10 mmol).

I-57 $^1$H NMR (400 MHz, methanol-d$_4$) δ 9.55 (s, 1H), 9.05 (s, 1H), 8.14 (d, J=9.6 Hz, 1H), 8.06-7.94 (m, 2H), 7.85 (d, J=8.8 Hz, 1H), 7.71 (d, J=9.5 Hz, 1H), 6.23 (p, J=7.1 Hz, 1H), 3.55-3.48 (m, 4H), 3.48-3.39 (m, 4H), 2.51 (dt, J=12.2, 6.0 Hz, 2H), 2.15-2.04 (m, 2H), 1.99-1.86 (m, 4H).

I-58a $^1$H NMR (600 MHz, chloroform-d, ppm) δ 9.17 (s, 1H), 8.22 (s, 1H), 8.17 (s, 1H), 8.04 (s, 1H), 8.01 (s, 1H), 7.76 (d, J=8.6 Hz, 1H), 7.57 (d, J=8.6 Hz, 1H), 6.18 (ddd, J=12.9, 7.3, 5.5 Hz, 1H), 3.59 (t, J=4.8 Hz, 4H), 2.93 (t, J=5.0 Hz, 4H), 2.43 (m, 2H), 2.40 (s, 3H), 2.08 (dd, J=12.7, 6.5 Hz, 2H), 1.94 (m, 2H), 1.86 (m, 2H), 1.50 (s, 9H).

I-58 LC-MS (ESI), C$_{24}$H$_{29}$N$_8$[M+H]$^+$: m/z=429.1.

I-59a $^1$H NMR (400 MHz, chloroform-d, ppm) δ 9.37 (s, 1H), 8.89 (s, 1H), 8.80 (d, J=9.3 Hz, 1H), 8.07 (d, J=8.9 Hz, 1H), 7.88 (d, J=9.1 Hz, 2H), 6.27-6.11 (m, 1H), 3.62 (d, J=5.0 Hz, 4H), 2.90 (d, J=5.0 Hz, 4H), 2.78 (s, 3H), 2.71-2.64 (m, 2H), 2.07 (d, J=18.9 Hz, 4H), 1.95 (m, 2H). 1.50 (s, 9H)

I-59 LC-MS (ESI), C$_{24}$H$_{29}$N$_8$[M+H]$^+$: m/z=429.3.

By referring to the synthetic method of I-2 in Example 2, compounds I-60 (7.9 mg, 19.0 μmmol, 19%), and I-61 (1 mg, 31.0 μmmol, 31%) were prepared from 9e (30 mg, 0.10 mmol).

I-60 $^1$H NMR (400 MHz, chloroform-d, ppm) δ 9.17 (s, 1H), 8.29 (d, J=9.0 Hz, 1H), 8.20 (s, 1H), 8.18 (s, 1H), 8.07 (d, J=2.9 Hz, 1H), 7.74 (d, J=8.7 Hz, 1H), 7.56 (d, J=8.6 Hz, 1H), 7.31 (dd, J=9.1, 3.0 Hz, 1H), 6.15 (p, J=7.0 Hz, 1H), 3.91 (dd, J=5.8, 3.7 Hz, 4H), 3.16 (dd, J=5.9, 3.7 Hz, 4H), 2.45 (dt, J=13.8, 7.3 Hz, 2H), 2.09-1.94 (m, 4H), 1.87 (dq, J=9.9, 3.9 Hz, 2H).

I-61 $^1$H NMR (400 MHz, chloroform-d, ppm) δ 9.18 (s, 1H), 8.22 (s, 1H), 8.17 (s, 1H), 8.13 (s, 1H), 8.05 (s, 1H), 7.76 (d, J=8.7 Hz, 1H), 7.57 (d, J=8.7 Hz, 1H), 6.23-6.13 (m, 1H), 3.92-3.83 (m, 4H), 3.02-2.94 (m, 4H), 2.41 (m, 2H), 2.40 (s, 3H) 2.14-2.05 (m, 2H), 1.97-1.80 (m, 4H).

Preparation of the Key Intermediate 1-isopropyl-5-methyl-8-(methylsulfinyl)-1H-imidazo[4,5-h]quinazoline (9f)

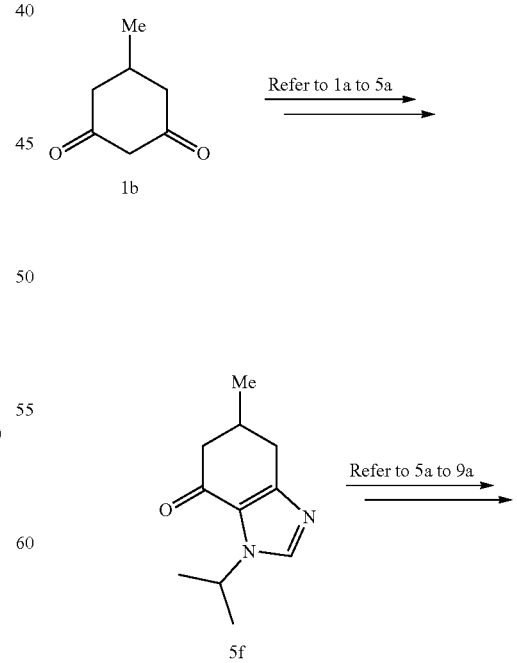

-continued

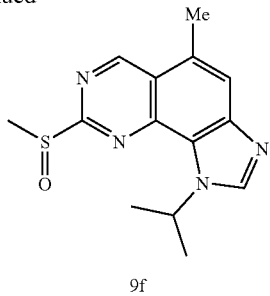

9f

1): By referring to the synthetic method of 5a in Example 1, the compound 3-isopropyl-6-methyl-3,5,6,7-tetrahydrogen-4H-benzo[d]imidazol-4-one (5f, 3.82 g, 19.9 mmol, 5%) was prepared from the compound 1b (50 g, 397 mmol) via four reaction steps. $^1$H NMR (400 MHz, chloroform-d, ppm) δ 7.67 (s, 1H), 5.09 (p, J=6.7 Hz, 1H), 2.92 (dd, J=16.3, 4.4 Hz, 1H), 2.56-2.45 (m, 2H), 2.37 (dtt, J=10.0, 7.0, 3.2 Hz, 1H), 2.27 (dd, J=15.7, 11.5 Hz, 1H), 1.46 (d, J=6.7 Hz, 6H), 1.13 (d, J=6.3 Hz, 3H).

2): By referring to the synthetic steps of 5a to 9a in Example 1, the title compound 9f (400 mg, 1.39 mmol, 7%) was prepared from 5f (3.8 g, 19.8 mmol) via four reaction steps.

$^1$H NMR (400 MHz, chloroform-d) δ 9.66 (d, J=1.7 Hz, 1H), 8.28 (d, J=1.6 Hz, 1H), 7.91 (d, J=1.2 Hz, 1H), 5.95 (pd, J=6.7, 1.7 Hz, 1H), 3.03 (d, J=1.8 Hz, 3H), 2.86 (d, J=1.1 Hz, 3H), 1.73 (dd, J=8.9, 6.8 Hz, 6H).

TABLE 6

Examples I-62 to I-66

| Side chains | Products |

TABLE 6-continued

Examples I-62 to I-66

| Side chains | Products |
|---|---|
| 10z | I-66 |

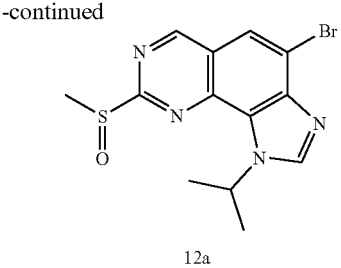

By referring to the synthetic method of I-1 in Example 1, the title compounds I-62 (11.0 mg, 25.2 μmmol, 24%), I-63 (8.1 mg, 17.9 μmmol, 17%), and I-64 (10.9 mg, 24.2 μmmol, 23%) were prepared from 9f (30 mg, 0.105 mmol).

I-62a $^1$H NMR (400 MHz, chloroform-d, ppm) δ 9.88 (s, 1H), 9.72 (s, 1H), 8.32 (dd, J=9.6, 3.0 Hz, 1H), 8.05 (d, J=2.9 Hz, 1H), 7.76 (s, 1H), 7.72 (d, J=9.6 Hz, 1H), 6.27 (p, J=6.7 Hz, 1H), 3.58 (dd, J=6.8, 3.8 Hz, 4H), 3.46 (dd, J=6.8, 3.7 Hz, 4H), 2.96 (s, 3H), 1.83 (d, J=6.7 Hz, 6H).

I-62 LC-MS (ESI), $C_{22}H_{27}N_8[M+H]^+$: m/z=403.1.

I-63 LC-MS (ESI), $C_{23}H_{29}N_8[M+H]^+$: m/z=417.3.

I-64 LC-MS (ESI), $C_{23}H_{29}N_8[M+H]^+$: m/z=417.5.

By referring to the synthetic method of I-2 in Example 2, compounds I-65 (8.0 mg, 20.0 μmmol, 19%), and I-66 (12.6 mg, 30.4 μmmol, 29%) were prepared from 9e (30 mg, 0.105 mmol).

I-65 LC-MS (ESI), $C_{22}H_{26}N_7O [M+H]^+$: m/z=404.3.

I-66 LC-MS (ESI), $C_{23}H_{28}N_7O [M+H]^+$: m/z=418.3.

Preparation of the Key Intermediate 4-bromo-1-isopropyl-8-(methylsulfinyl)-1H-imidazo[4,5-h]quinazoline (12a)

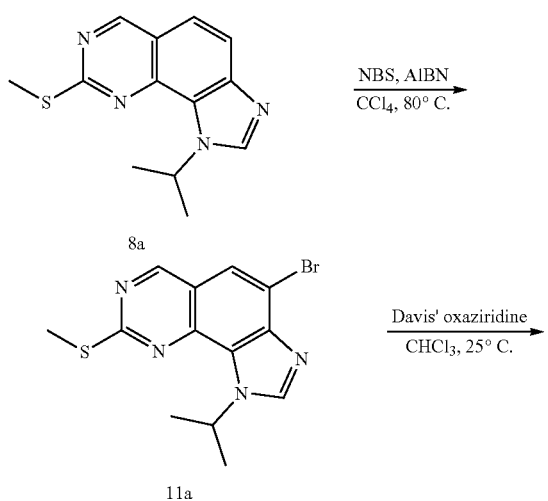

1): 4-Bromo-1-isopropyl-8-(methylthio)-1H-imidazo[4,5-h]quinazoline (12a)

8a (1.8 g, 6.98 mmol), N-bromosuccinimide (2.48 g, 13.96 mmol) and azobisisobutyronitrile (344 mg, 2.1 mmol) were suspended in carbon tetrachloride (40 mL), and the atmosphere of the reaction system was replaced with argon for 3 times. The reaction mixture was heated to 80° C., and stirred for 18 hours. After the reaction mixture was concentrated, it was purified with flash silica gel column chromatography (petroleum ether/ethyl acetate=3:1) to afford a light yellow solid as 4-bromo-1-isopropyl-8-(methylthio)-1H-imidazo[4,5-h]quinazoline (11a, 961.0 mg, 2.86 mmol, 41%). LC-MS (ESI) for $C_{13}H_{14}BrN_4S [M+H]^+$: m/z=337.3, 339.2.

2): By referring to the synthetic steps of 8a to 9a in Example 1, the title compound 12a (401 mg, 1.14 mmol, 83%) was prepared from 11a (460 mg, 1.37 mmol). LC-MS (ESI) for $C_{13}H_{14}BrN_4OS [M+H]^+$: m/z=353.1, 355.3.

TABLE 7
Examples I-67 to I-71
| Side chains | Products | |
|---|---|---|
| 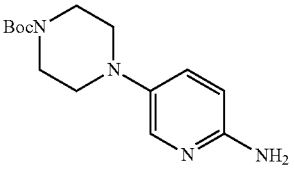 [SMILES: CC(C)(C)OC(=O)N1CCN(c2ccc(N)nc2)CC1] 10a | 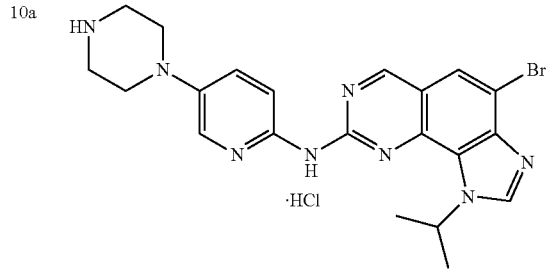 ·HCl | I-67 |
| 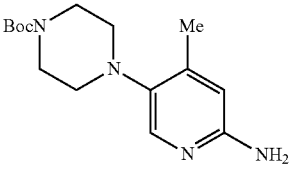 [SMILES: Cc1cc(N)ncc1N1CCN(C(=O)OC(C)(C)C)CC1] 10h | 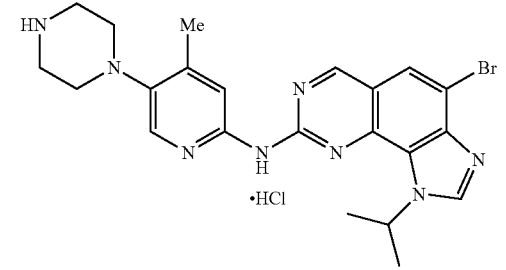 [SMILES: Cc1cc(Nc2ncc3cc(Br)c4ncn(C(C)C)c4c3n2)ncc1N1CCNCC1 ; Cl] ·HCl | I-68 |
| 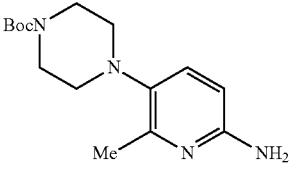 10i | 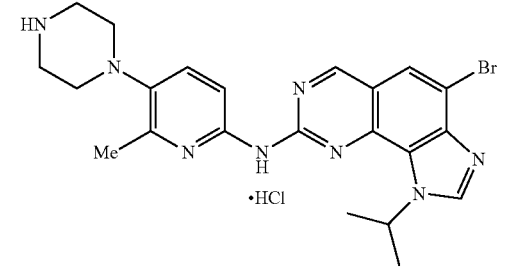 [SMILES: Cc1nc(Nc2ncc3cc(Br)c4ncn(C(C)C)c4c3n2)ccc1N1CCNCC1 ; Cl] ·HCl | I-69 |
| 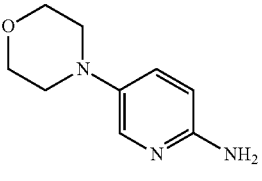 [SMILES: Nc1ccc(N2CCOCC2)cn1] 10w | 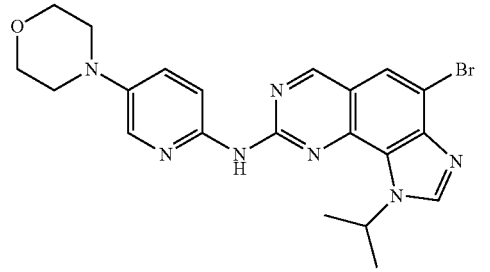 [SMILES: CC(C)n1cnc2c(Br)cc3cnc(Nc4ccc(N5CCOCC5)cn4)nc3c21] | I-70 |
| 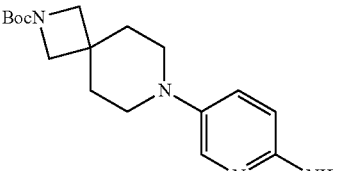 10ze | 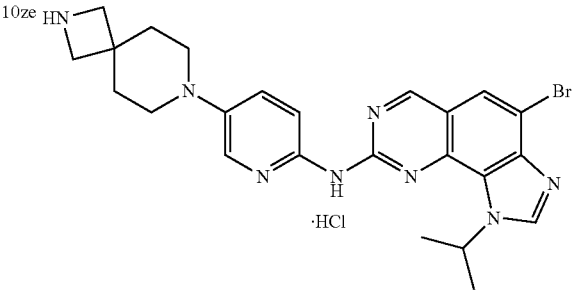 ·HCl | I-71 |

By referring to the synthetic method of I-1 in Example 1, the title compounds I-67 (11.5 mg, 23.0 μmmol, 23%), I-68 (7.2 mg, 14.0 μmmol, 14%), I-69 (12.9 mg, 25.0 μmmol, 25%), and I-71 (6.0 mg, 11.0 μmmol, 11%) were prepared from 12a (35 mg, 0.10 mmol).

I-67a $^1$H NMR (400 MHz, chloroform-d, ppm) δ 9.10 (s, 1H), 8.25 (d, J=4.3 Hz, 2H), 8.09-7.98 (m, 2H), 7.80 (s, 1H), 7.34 (dd, J=9.1, 3.0 Hz, 1H), 6.06 (p, J=6.8 Hz, 1H), 3.63 (t, J=5.1 Hz, 4H), 3.13 (t, J=5.1 Hz, 4H), 1.73 (d, J=6.7 Hz, 6H), 1.50 (s, 9H).

I-67 LC-MS (ESI), $C_{21}H_{24}BrN_8$ [M+H]$^+$: m/z=467.1, 469.2.

I-68 LC-MS (ESI), $C_{22}H_{26}BrN_8$ [M+H]$^+$: m/z=481.1, 483.3.

I-69 LC-MS (ESI), $C_{22}H_{26}BrN_8$ [M+H]$^+$: m/z=481.3, 483.5.

I-71a $^1$H NMR (400 MHz, chloroform-d, ppm) δ 9.10 (s, 1H), 8.31-8.19 (m, 2H), 8.14 (s, 1H), 8.06 (d, J=2.8 Hz, 1H), 7.79 (s, 1H), 7.33 (dd, J=9.0, 2.9 Hz, 1H), 6.06 (dt, J=13.8, 7.0 Hz, 1H), 3.71 (s, 4H), 3.19-3.03 (m, 4H), 2.01-1.86 (m, 4H), 1.73 (d, J=6.8 Hz, 6H), 1.46 (s, 8H).

I-71 LC-MS (ESI), $C_{24}H_{28}BrN_8$ [M+H]$^+$: m/z=507.3, 509.3.

By referring to the synthetic method of I-2 in Example 2, the compound I-70 (12.6 mg, 27.0 μmmol, 27%) was prepared from 12a (35 mg, 0.10 mmol). $^1$H NMR (400 MHz, chloroform-d, ppm) δ 9.11 (s, 1H), 8.26 (d, J=6.9 Hz, 2H), 8.07 (d, J=17.4 Hz, 2H), 7.80 (s, 1H), 7.32 (d, J=7.5 Hz, 1H), 6.12-5.99 (m, 1H), 4.04-3.81 (m, 4H), 3.30-3.06 (m, 4H), 1.73 (d, J=6.6 Hz, 6H).

Preparation of the Key Intermediate 1-isopropyl-4-methyl-8-(methylsulfinyl)-1H-imidazo[4,5-h]quinazoline (14a)

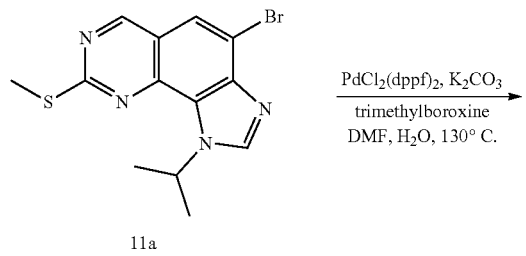

11a

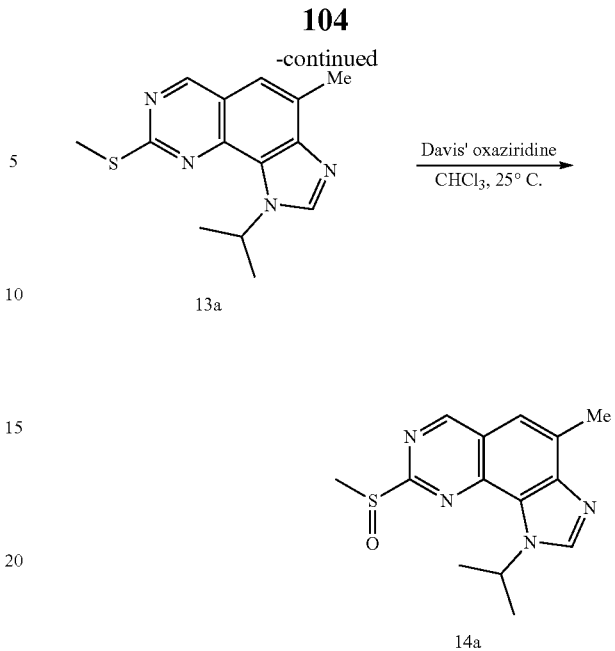

1): 11a (500 mg, 1.49 mmol), [1,1'-bis(diphenylphosphine)ferrocene]palladium dichloride (110 mg, 0.15 mmol), potassium carbonate (8.6 g, 62.3 mmol) and trimethylboroxine (3.5 M in THF, 1.7 mL, 6.0 mmol) were suspended in a mixed solvent of N,N-dimethylformamide (8 mL) and water (4 mL). The atmosphere of the reaction system was placed with argon for 3 times, and the mixture was heated to 130° C., and stirred overnight. The reaction mixture was diluted with ethyl acetate (100 mL) and water (30 mL), and the organic layer was washed twice with water (15 mL) and brine (15 mL), respectively, dried over anhydrous sodium sulfate, filtered, and concentrated. The resulting residue was purified with flash silica gel column chromatography (petroleum ether/ethyl acetate=3:1) to afford a light yellow solid as 1-isopropyl-4-methyl-8-(methylthio)-1H-imidazo[4,5-h]quinazoline (13a, 340 mg, 1.25 mmol, 84%). LC-MS (ESI) for $C_{14}H_{17}N_4S$ [M+H]$^+$: m/z=273.1.

2): By referring to the synthetic steps of 8a to 9a in Example 1, the title compound 14a (317 mg, 1.10 mmol, 91%) was prepared from 13a (330 mg, 1.21 mmol). LC-MS (ESI) for $C_{14}H_{17}N_4OS$ [M+H]$^+$: m/z=289.2.

TABLE 8

Examples I-72 to I-76

| Side chains | Products |
|---|---|
| ![10a structure] | ![I-72 structure] |

TABLE 8-continued

Examples I-72 to I-76

| Side chains | Products |
|---|---|
| 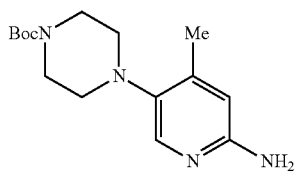 10h | 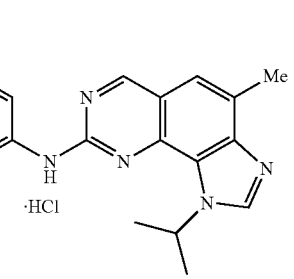 I-73 ·HCl |
| 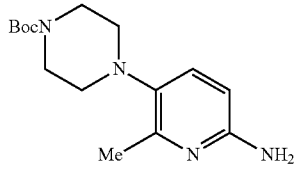 [SMILES: Cc1nc(N)ccc1N1CCN(C(=O)OC(C)(C)C)CC1] 10i | 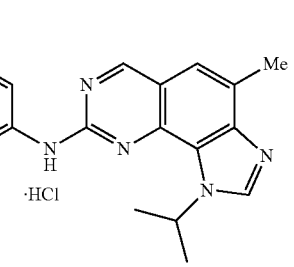 I-74 ·HCl |
| 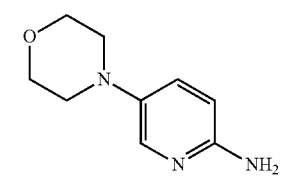 10w | 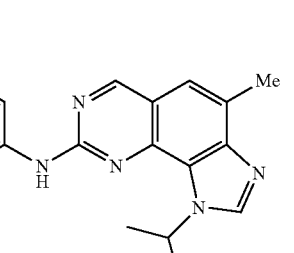 I-75 |
| 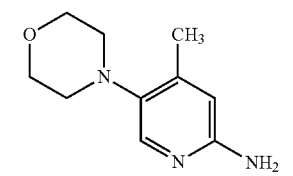 10x | 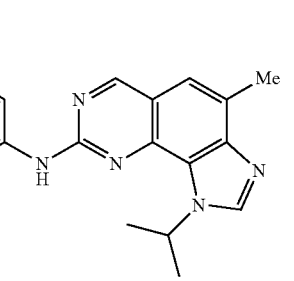 I-76 |

By referring to the synthetic method of I-1 in Example 1, compounds I-72 (9.2 mg, 21 μmmol, 15%), I-73 (10.2 mg, 22.6 μmmol, 13%), and I-74 (20.4 mg, 45.2 μmmol, 26%) were prepared from 14a (50 mg, 0.174 mmol).

I-72a $^1$H NMR (400 MHz, chloroform-d, ppm) δ 9.11 (s, 1H), 8.31 (d, J=9.0 Hz, 1H), 8.20 (s, 1H), 8.13 (s, 1H), 8.06 (d, J=3.0 Hz, 1H), 7.35 (brs, 1H), 7.33 (d, J=3.0 Hz, 1H), 6.07 (p, J=6.7 Hz, 1H), 3.63 (t, J=5.1 Hz, 4H), 3.12 (t, J=5.2 Hz, 4H), 2.75-2.71 (m, 3H), 1.73 (d, J=6.8 Hz, 6H), 1.49 (s, 9H).

I-73a $^1$H NMR (400 MHz, chloroform-d) δ 9.12 (s, 1H), 8.22 (d, J=2.7 Hz, 2H), 8.17 (s, 1H), 8.02 (s, 1H), 7.40-7.33 (m, 1H), 6.10 (dt, J=13.4, 6.7 Hz, 1H), 3.69-3.52 (m, 4H), 3.01-2.85 (m, 4H), 2.81-2.69 (m, 3H), 2.42 (s, 3H), 1.74 (d, J=6.7 Hz, 6H), 1.50 (s, 9H).

I-74a $^1$H NMR (400 MHz, chloroform-d, ppm) δ 9.11 (s, 1H), 8.19 (d, J=10.5 Hz, 2H), 8.06 (s, 1H), 7.41-7.32 (m, 2H), 6.07 (dt, J=13.6, 6.8 Hz, 1H), 3.70-3.53 (m, 4H), 2.94-2.80 (m, 4H), 2.77-2.67 (m, 3H), 2.52 (s, 3H), 1.72 (d, J=6.8 Hz, 6H), 1.50 (s, 9H).

By referring to the synthetic method of I-2 in Example 2, compounds I-75 (16.1 mg, 40.0 μmmol, 23%), and I-76 (18.9 mg, 45.2 μmmol, 26%) were prepared from 14a (50 mg, 0.174 mmol).

I-75 $^1$H NMR (400 MHz, chloroform-d, ppm) δ 9.12 (s, 1H), 8.39-8.25 (m, 2H), 8.20 (s, 1H), 8.07 (d, J=2.7 Hz, 1H), 7.42-7.28 (m, 2H), 6.07 (h, J=6.9 Hz, 1H), 4.03-3.81 (m, 4H), 3.28-3.04 (m, 4H), 2.84-2.68 (m, 3H), 1.73 (d, J=6.8 Hz, 6H).

I-76 $^1$H NMR (400 MHz, chloroform-d, ppm) δ 9.15 (s, 1H), 8.67 (s, 1H), 8.21 (d, J=3.3 Hz, 2H), 8.12 (s, 1H), 7.35

(s, 1H), 6.09 (dt, J=13.4, 6.6 Hz, 1H), 4.02-3.74 (m, 4H), 3.12-2.91 (m, 4H), 2.73 (s, 3H), 2.42 (s, 3H), 1.73 (d, J=6.7 Hz, 6H).

Example 77

Potency determination in the biochemical kinase inhibitory assay. Kinase activity assay and IC50 determination.

First, 10 ng of recombinant CDK4/cyclin D1 (Life Technologies PV4204) was diluted in a kinase buffer (20 mM Tris pH7.5, 10 mM $MgCl_2$, 0.01% NP-40, 2 mM DTT), and incubated at room temperature for 30 minutes together with indicated concentration of inhibitors. The kinase reaction was initiated by the addition of 1 μg (1.5 μM) of recombinant retinoblastoma protein, 5 μM ATP and 10μ Ci γ-32P-ATP. The reaction was incubated at 30° C. for 20 minutes, and the reaction was stopped by the addition of 2× Laemmli sample buffer, heated at 95° C. for three minutes, and dissolved in 12% acrylamide SDS-PAGE for autoradiography. The corresponding phosphorylated substrate protein bands were quantified using a densitometer (Bio-Rad). The resulting density values were plotted as a function of log drug concentration using Prism 4 Graphpad software, and IC50 values were determined by plotting a non-linear regression curve with a variable slope.

The compounds disclosed herein were tested in a similar manner for their inhibitory activities against CDK6/cyclin D1, CDK2/cyclin A, CDK5/cyclin P25, CDK9/cyclin Ti, CDK7/cyclin H and CDK19/cyclin C.

The results of the enzyme inhibitory activity of the most representative compounds disclosed herein are shown in the following table. Compounds were tested in a three-fold serial dilution from the starting concentration of 10 μM, over 10-fold of IC50. Control compound, staurosporine, was tested in a four-fold serial dilution from the starting concentration of 20 μM, over 10-fold of IC50. The reaction took place in the presence of 10 μM ATP.

| Compound No. | CDK4/cyclin D1 IC50 (nM) | CDK6/cyclin D1 IC50 (nM) |
| --- | --- | --- |
| staurosporine | 16 | 35 |
| I-1 | <2 | <2 |
| I-2 | 2-10 | 2-10 |
| I-3 | 2-10 | 2-10 |
| I-4 | 2-10 | 2-10 |
| I-5 | <2 | <2 |
| I-6 | 2-10 | 2-10 |
| I-7 | 2-10 | 2-10 |
| I-8 | <2 | <2 |
| I-9 | <2 | <2 |
| I-10 | 2-10 | 2-10 |
| I-11 | 2-10 | 2-10 |
| I-12 | 2-10 | 2-10 |
| I-13 | 10-50 | 10-50 |
| I-14 | 10-50 | 10-50 |
| I-15 | 10-50 | 10-50 |
| I-16 | 10-50 | 10-50 |
| I-17 | 10-50 | 10-50 |
| I-18 | 10-50 | 10-50 |
| I-19 | 10-50 | 10-50 |
| I-20 | 10-50 | 10-50 |
| I-21 | 10-50 | 10-50 |
| I-22 | 10-50 | 10-50 |
| I-23 | <2 | <2 |
| I-24 | 2-10 | 2-10 |
| I-25 | 2-10 | 2-10 |
| I-26 | 2-10 | 2-10 |
| I-27 | 2-10 | 2-10 |
| I-28 | 10-50 | 10-50 |
| I-29 | 10-50 | 10-50 |
| I-30 | 10-50 | 10-50 |
| I-31 | 10-50 | 10-50 |
| I-32 | 10-50 | 10-50 |
| I-33 | 10-50 | 10-50 |
| I-34 | 10-50 | 10-50 |
| I-35 | 10-50 | 10-50 |
| I-36 | 50-100 | 50-100 |
| I-37 | 50-100 | 50-100 |
| I-38 | 10-50 | 10-50 |
| I-39 | 50-100 | 50-100 |
| I-40 | 50-100 | 50-100 |
| I-41 | 50-100 | 50-100 |
| I-42 | 10-50 | 10-50 |
| I-43 | 10-50 | 10-50 |
| I-44 | 10-50 | 10-50 |
| I-45 | 10-50 | 10-50 |
| I-46 | 10-50 | 10-50 |
| I-47 | 2-10 | 2-10 |
| I-48 | 10-50 | 10-50 |
| I-49 | 10-50 | 10-50 |
| I-50 | 10-50 | 10-50 |
| I-51 | 10-50 | 10-50 |
| I-52 | 10-50 | 10-50 |
| I-53 | 10-50 | 10-50 |
| I-54 | 10-50 | 10-50 |
| I-55 | 10-50 | 10-50 |
| I-56 | 10-50 | 10-50 |
| I-57 | <2 | <2 |
| I-58 | 2-10 | 2-10 |
| I-59 | 2-10 | 2-10 |
| I-60 | 2-10 | 2-10 |
| I-61 | 2-10 | 2-10 |
| I-62 | 50-100 | 50-100 |
| I-63 | 50-100 | 50-100 |
| I-64 | 50-100 | 50-100 |
| I-65 | 50-100 | 50-100 |
| I-66 | 50-100 | 50-100 |
| I-67 | 2-10 | 2-10 |
| I-68 | 2-10 | 2-10 |
| I-69 | 2-10 | 2-10 |
| I-70 | 2-10 | 2-10 |
| I-71 | 10-50 | 10-50 |
| I-72 | 2-10 | 2-10 |
| I-73 | 2-10 | 2-10 |
| I-74 | 2-10 | 2-10 |
| I-75 | 2-10 | 2-10 |
| I-76 | 10-50 | 10-50 |

The above is a further detailed description of the present disclosure in connection with the specific preferred embodiments, and the specific embodiments of the present disclosure are not limited to the description. It will be apparent to those skilled in the art that the present disclosure may be practiced by making various simple deduction and replacement, without departing from the spirit and scope of the invention.

The invention claimed is:

1. A compound of formula (I), or a pharmaceutically acceptable salt, enantiomer, diastereomer, racemate, or mixture thereof:

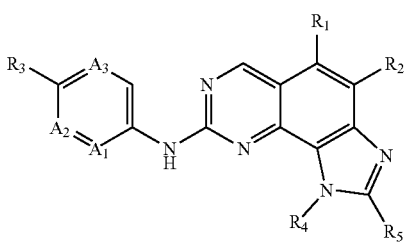

wherein:

$A_1$ is selected from N, CH, or C—OMe;

$A_2$ is selected from N, CH, C—$C_{1-6}$ alkyl or C-halogen;

$A_3$ is selected from N, CH, C—$C_{1-6}$ alkyl or C-halogen;

$R_1$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted with oxo or thioxo;

$R_2$ is selected from H, halogen, —CN, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted with oxo or thioxo;

$R_3$ is -3- to 11-membered heterocyclyl which is optionally substituted with 1, 2, 3, 4 or 5 $R_6$ groups;

$R_4$ is selected from —C(O)$R_a$, —C(O)$OR_a$, —C(O)$NR_bR_c$, $C_{1-6}$ alkyl, $C_{1-6}$ haloalkyl, $C_{3-7}$ cycloalkyl, or 3- to 7-membered heterocyclyl;

$R_5$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted with oxo or thioxo;

$R_6$ is selected from H, —$NH_2$, —$NHC_{1-6}$ alkyl, —N($C_{1-6}$ alkyl)$_2$, $C_{1-6}$ alkyl, $C_{1-6}$ haloalkyl, —$C_{1-6}$ alkylene-$OR_a$, -L-$C_{3-7}$ cycloalkyl, -L-3- to 7-membered heterocyclyl, -L-$C_{6-10}$ aryl, or -L-5- to 10-membered heteroaryl; or two $R_6$ groups on the same carbon atom are taken together to form oxo or thioxo;

wherein:

$R_4$ is optionally substituted with 1, 2 or 3 R' groups, wherein R' is independently selected from H, halogen, —CN, —$NO_2$, —$OR_a$, —$SR_a$, —$NR_bR_c$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl;

each of $R_3$, $R_5$ and $R_6$ is optionally substituted with 1, 2 or 3 R" groups, wherein R" is independently selected from H, —OH, halogen, —$NO_2$, carbonyl, -L-CN, -L-$OR_a$, -L-$SR_a$, -L-$NR_bR_c$, -L-C(O)$R_a$, -L-C(S)$R_a$, -L-C(O)$OR_a$, -L-C(S)$OR_a$, -L-C(O)—$NR_bR_c$, -L-C(S)—$NR_bR_c$, -L-O—C(O)$R_a$, -L-O—C(S)$R_a$, -L-N($R_b$)—C(O)—$R_a$, -L-N($R_b$)—C(S)—$R_a$, -L-S(O)$_m$$R_a$, -L-S(O)$_m$$OR_a$, -L-S(O)$_m$$NR_bR_c$, -L-N($R_b$)—S(O)$_m$—$R_a$, -L-N($R_b$)—S(O)$_m$—$R_bR_c$, -L-N($R_b$)—C(O)$OR_a$, -L-N($R_b$)—C(S)$OR_a$, -L-O—$C_{1-6}$ alkylene-$OR_a$, -L-C(O)—$C_{1-6}$ alkylene-$NR_bR_c$, -L-N($R_b$)—C(O)—$NR_bR_c$, -L-N($R_b$)—C(S)—$NR_bR_c$, -L-O—C(O)—

$NR_bR_c$, -L-O—C(S)—$NR_bR_c$, $C_{1-6}$ alkyl, $C_{1-6}$ haloalkyl, $C_{2-6}$ alkenyl, $C_{2-6}$ alkynyl, -L-$C_{3-7}$ cycloalkyl, -L-3- to 7-membered heterocyclyl, -L-$C_{6-10}$ aryl, or -L-5- to 10-membered heteroaryl; wherein the said $C_{1-6}$ alkyl, $C_{1-6}$ haloalkyl, $C_{2-6}$ alkenyl, $C_{2-6}$ alkynyl, -L-$C_{3-7}$ cycloalkyl, -L-3- to 7-membered heterocyclyl, -L-$C_{6-10}$ aryl, or -L-5- to 10-membered heteroaryl is each optionally further substituted with one or more substituents independently selected from the group consisting of -L-CN, —$NO_2$, carbonyl, -L-$OR_a$, -L-$SR_a$, -L-$NR_bR_c$, -L-C(O)$R_a$, -L-C(S)$R_a$, -L-C(O)$OR_a$, -L-C(S)$OR_a$, -L-C(O)—$NR_bR_c$, -L-C(S)—$NR_bR_c$, -L-O—C(O)$R_a$, -L-O—C(S)$R_a$, -L-N($R_b$)—C(O)—$R_a$, -L-N($R_b$)—C(S)—$R_a$, -L-S(O)$_m$$R_a$, -L-S(O)$_m$$OR_a$, -L-S(O)$_m$$NR_bR_c$, -L-N($R_b$)—S(O)$_m$—$R_a$, -L-N($R_b$)—S(O)$_m$—$R_bR_c$, -L-N($R_b$)—C(O)$OR_a$, -L-N($R_b$)—C(S)$OR_a$, -L-O—$C_{1-6}$ alkylene-$OR_a$, -L-C(O)—$C_{1-6}$ alkylene-$NR_bR_c$, -L-N($R_b$)—C(O)—$NR_bR_c$, -L-N($R_b$)—C(S)—$NR_bR_c$, -L-O—C(O)—$NR_bR_c$, and -L-O—C(S)—$NR_bR_c$;

$R_a$ is independently selected from H, $C_{1-6}$ alkyl, $C_{2-6}$ alkenyl, $C_{2-6}$ alkynyl, $C_{1-6}$ haloalkyl, -L-$C_{3-7}$ cycloalkyl, -L-3- to 7-membered heterocyclyl, -L-$C_{6-10}$ aryl, or -L-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, -L-$C_{3-7}$ cycloalkyl, -L-3- to 7-membered heterocyclyl, -L-$C_{6-10}$ aryl, or -L-5- to 10-membered heteroaryl; or, $R_b$ and $R_c$ are taken together with the nitrogen atom to which they are attached to form 3- to 7-membered heterocyclyl;

$R_a$, $R_b$ and $R_c$ are each optionally further substituted with one or more substituents independently selected from the group consisting of $C_{1-6}$ alkyl, $C_{2-6}$ alkenyl, $C_{2-6}$ alkynyl, $C_{1-6}$ haloalkyl, -L-$C_{3-7}$ cycloalkyl, -L-3- to 7-membered heterocyclyl, -L-$C_{6-10}$ aryl, and -L-5- to 10-membered heteroaryl;

L is selected from a chemical bond, —$C_{1-6}$ alkylene-, —$C_{2-6}$ alkenylene- or —$C_{2-6}$ alkynylene-; and m represents 0, 1 or 2.

2. The compound of formula (I), or the pharmaceutically acceptable salt, enantiomer, diastereomer, racemate, or mixture thereof according to claim 1, wherein, $A_1$ is N;

$A_2$ is CH, C—$C_{1-6}$ alkyl or C-halogen;

$A_3$ is CH, C—$C_{1-6}$ alkyl or C-halogen;

$R_1$ is H;

$R_2$ is selected from H, halogen, $C_{1-6}$ alkyl or $C_{1-6}$ haloalkyl;

$R_3$ is 3- to 11-membered heterocyclyl which is optionally substituted with 1, 2, 3 or 4 $R_6$ groups;

$R_4$ is isopropyl;

$R_5$ is H;

$R_6$ is independently selected from H, —$NH_2$, —$NHC_{1-6}$ alkyl, —N($C_{1-6}$ alkyl)$_2$, $C_{1-6}$ alkyl, $C_{1-6}$ haloalkyl or —$C_{0-6}$ alkylene-$OR_a$;

$R_a$ is selected from H or $C_{1-6}$ alkyl.

3. A compound of formula (II-1), or a pharmaceutically acceptable salt, enantiomer, diastereomer, racemate, or mixture thereof:

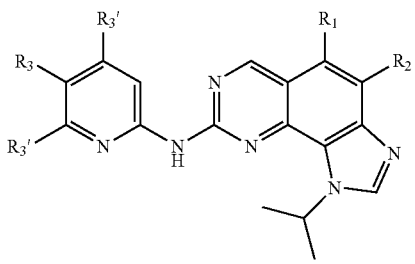

(II-1)

wherein,
$R_1$ is H, $C_{1-6}$ alkyl or $C_{1-6}$ haloalkyl;
$R_2$ is H, halogen, $C_{1-6}$ alkyl or $C_{1-6}$ haloalkyl;
$R_3$ is 3- to 11-membered heterocyclyl which is optionally substituted with 1, 2 or 3 $R_6$ groups;
$R_3'$ is independently selected from H or $C_{1-6}$ alkyl;
$R_6$ is independently selected from H, $C_{1-6}$ alkyl or $C_{1-6}$ haloalkyl.

4. The compound, or a pharmaceutically acceptable salt, enantiomer, diastereomer, racemate, or mixture thereof according to claim 3, which is a compound of formula (II-2), or a pharmaceutically acceptable salt, enantiomer, diastereomer, racemate, or mixture thereof:

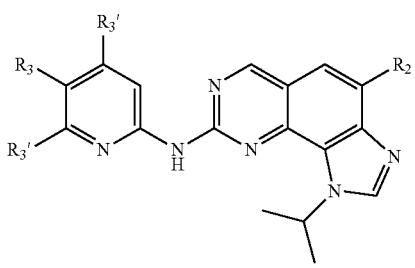

(II-2)

wherein,
$R_2$ is selected from H halogen, $C_{1-6}$ alkyl or $C_{1-6}$ haloalkyl;
$R_3$ is selected from

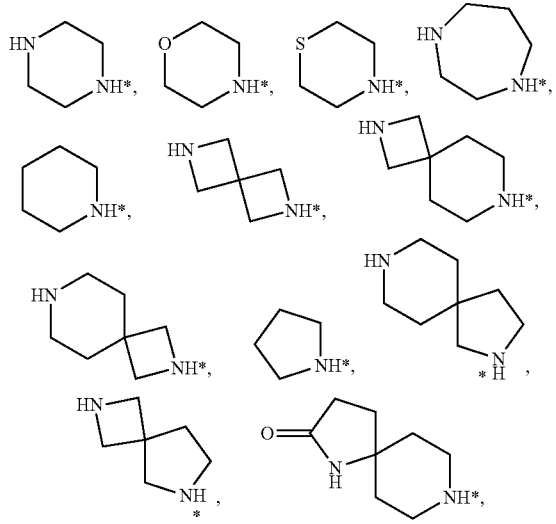

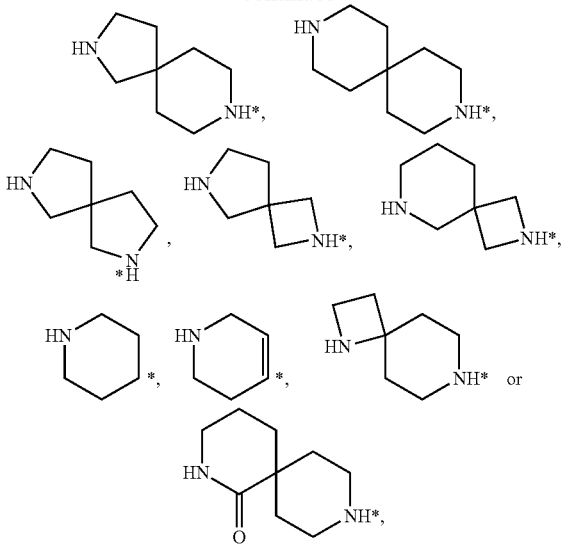

any of which is optionally substituted with 1, 2 or 3 $R_6$ groups;
$R_3'$ is independently selected from H, halogen, $C_{1-6}$ alkyl or $C_{1-6}$ haloalkyl;
$R_6$ is independently selected from H, —$NH_2$, —$NHC_{1-6}$ alkyl, —$N(C_{1-6}$ alkyl$)_2$, $C_{1-6}$ alkyl, $C_{1-6}$ haloalkyl or —$C_{0-6}$ alkylene-$OR_a$;
$R_a$ is selected from H or $C_{1-6}$ alkyl.

5. The compound, or a pharmaceutically acceptable salt, enantiomer, diastereomer, racemate, or mixture thereof according to claim 4, wherein,
$R_2$ is selected from H, halogen or $C_{1-6}$ alkyl;
$R_3'$ is independently selected from H, halogen or $C_{1-6}$ alkyl;
$R_3$ is selected from

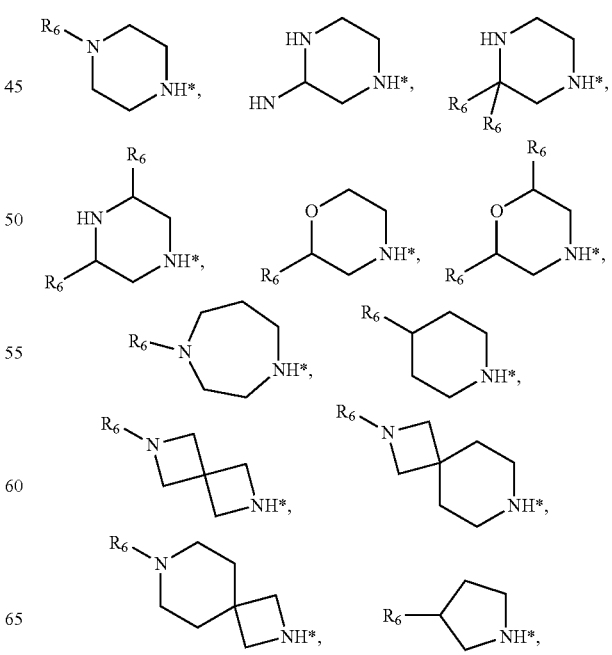

-continued

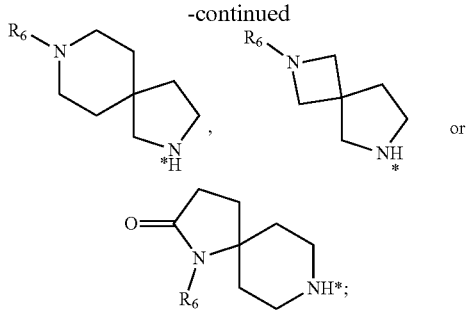

$R_6$ is independently selected from H, —$NH_2$, —$NHC_{1-6}$ alkyl, —$N(C_{1-6}$ alkyl$)_2$, $C_{1-6}$ alkyl or —$C_{0-6}$ alkylene-$OR_a$.

6. The compound, or a pharmaceutically acceptable salt, enantiomer, diastereomer, racemate, or mixture thereof according to claim 3, which is a compound of formula (II-3), or a pharmaceutically acceptable salt, enantiomer, diastereomer, racemate, or mixture thereof:

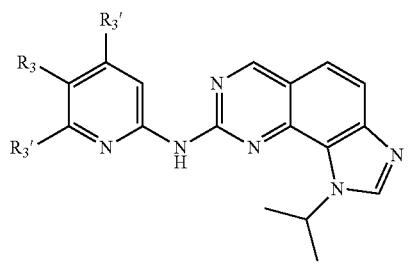 (II-3)

wherein,
$R_3$ is selected from

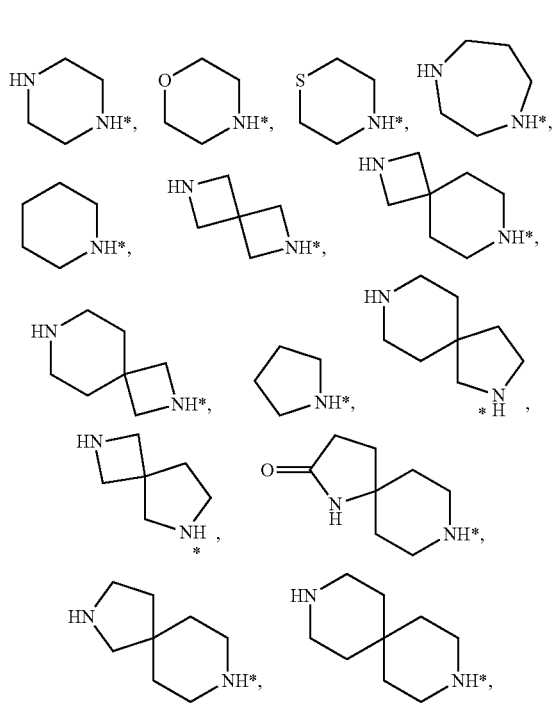

-continued

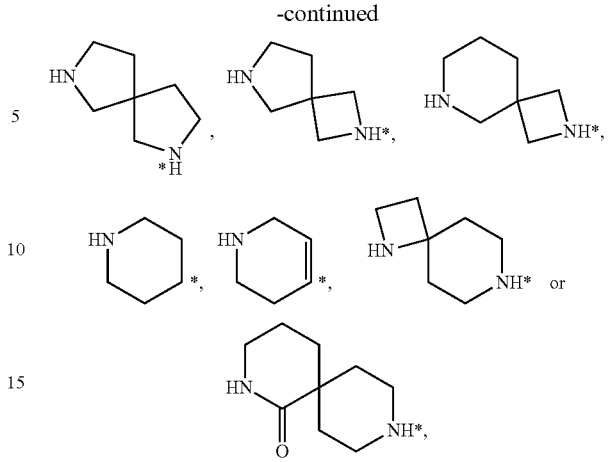

any of which is optionally substituted with 1, 2, 3 or 4 $R_6$ groups;

$R_3'$ is independently selected from H, halogen, $C_{1-6}$ alkyl or $C_{1-6}$ haloalkyl;

$R_6$ is independently selected from H, —$NH_2$, —$NHC_{1-6}$ alkyl, —$N(C_{1-6}$ alkyl$)_2$, $C_{1-6}$ alkyl, $C_{1-6}$ haloalkyl or —$C_{0-6}$ alkylene-$OR_a$;

$R_a$ is selected from H or $C_{1-6}$ alkyl.

7. The compound, or a pharmaceutically acceptable salt, enantiomer, diastereomer, racemate, or mixture thereof according to claim 6, wherein $R_3$ is selected from

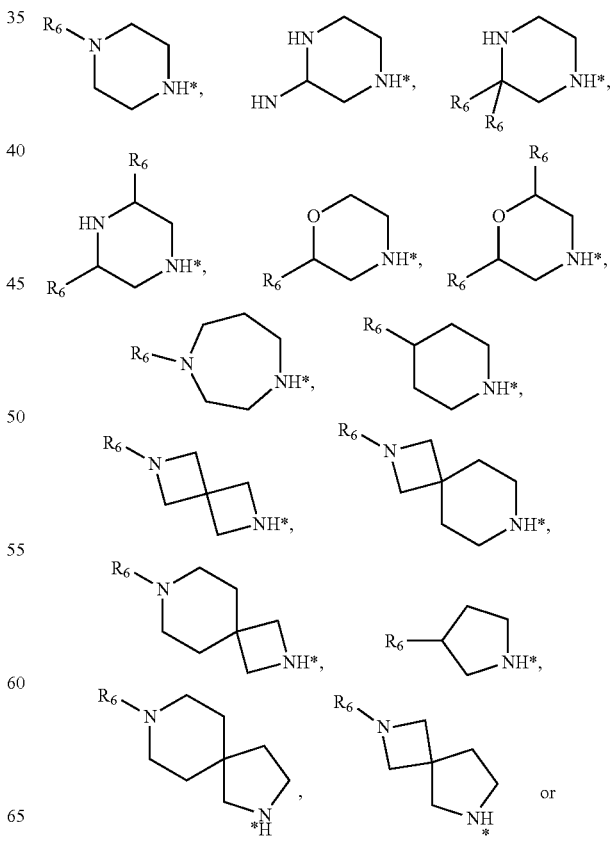

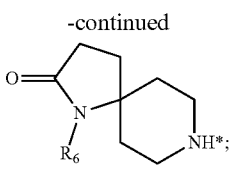

$R_3'$ is independently selected from H, halogen or $C_{1-6}$ alkyl;

$R_6$ is independently selected from H, —NH$_2$, —NHC$_{1-6}$ alkyl, —N(C$_{1-6}$ alkyl)$_2$, C$_{1-6}$ alkyl or —C$_{0-6}$ alkylene-OR$_a$;

$R_a$ is selected from H or C$_{1-6}$ alkyl.

8. The compound, or a pharmaceutically acceptable salt, enantiomer, diastereomer, racemate, or mixture thereof according to claim 6, wherein $R_3$ is selected from

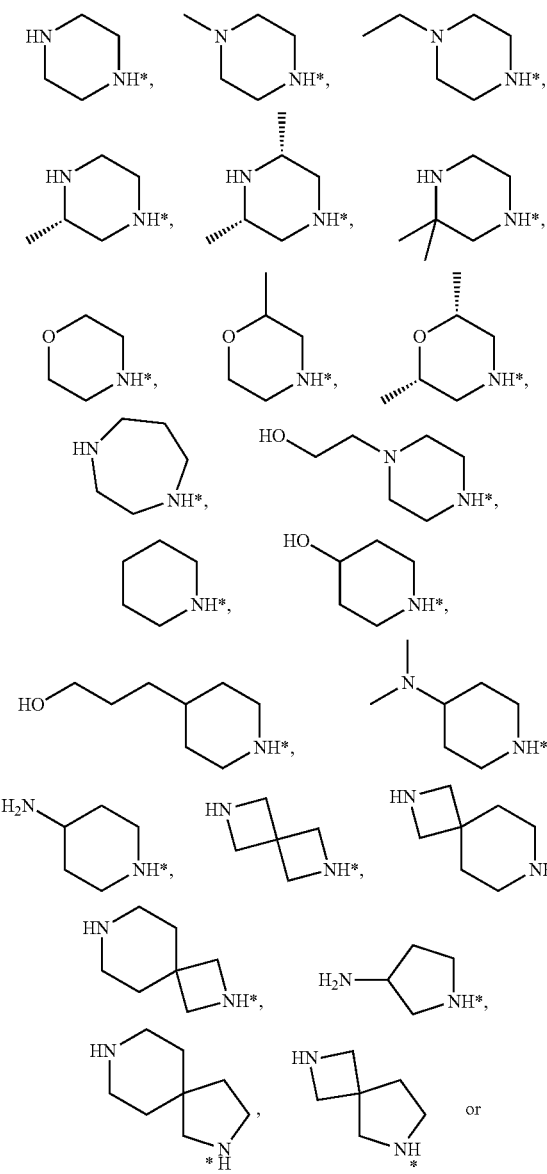

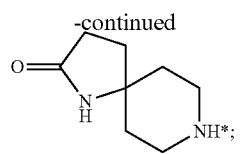

$R_3'$ is independently selected from H, F or methyl.

9. The compound, or a pharmaceutically acceptable salt, enantiomer, diastereomer, racemate, or mixture thereof according to claim 6, wherein $R_3$ is 5- to 6-membered heterocyclyl which is optionally substituted with 1, 2, 3 or 4 $R_6$ groups;

$R_3'$ is independently selected from H, C$_{1-6}$ alkyl or C$_{1-6}$ haloalkyl;

$R_6$ is independently selected from H, C$_{1-6}$ alkyl or C$_{1-6}$ haloalkyl.

10. The compound, or a pharmaceutically acceptable salt, enantiomer, diastereomer, racemate, or mixture thereof according to claim 6, wherein $R_3$ is selected from

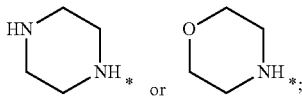 [SMILES: C1CNCCN1 ; C1COCCN1]

any of which is optionally substituted with 1, 2 or 3 $R_6$ groups;

$R_3'$ is independently selected from H or C$_{1-6}$ alkyl;

$R_6$ is independently selected from H, C$_{1-6}$ alkyl or C$_{1-6}$ haloalkyl.

11. The compound, or a pharmaceutically acceptable salt, enantiomer, diastereomer, racemate, or mixture thereof according to claim 6, wherein $R_3$ is selected from

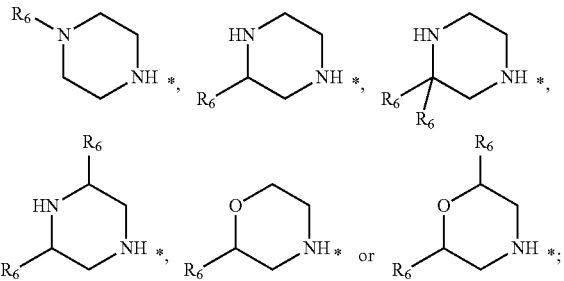

$R_3'$ is independently selected from H or C$_{1-6}$ alkyl;

$R_6$ is independently selected from H, C$_{1-6}$ alkyl or C$_{1-6}$ haloalkyl.

12. The compound, or a pharmaceutically acceptable salt, enantiomer, diastereomer, racemate, or mixture thereof according to claim 6, wherein $R_3$ is selected from

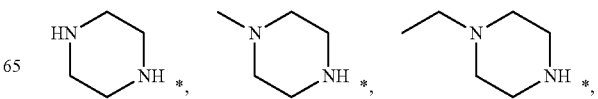

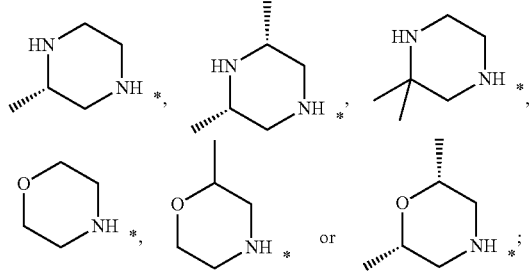

$R_3'$ is independently selected from H or methyl.

13. The compound, or a pharmaceutically acceptable salt, enantiomer, diastereomer, racemate, or mixture thereof according to claim 3, which is a compound of formula (II-4), or a pharmaceutically acceptable salt, enantiomer, diastereomer, racemate, or mixture thereof:

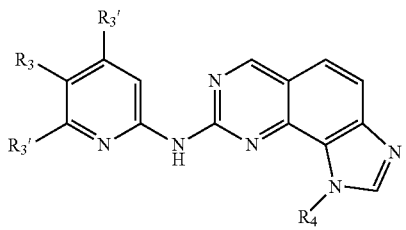

(II-4)

wherein,
$R_3$ is selected from

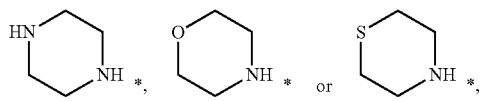

any of which is optionally substituted with 1, 2, 3 or 4 $R_6$ groups;
$R_3'$ is independently selected from H, $C_{1-6}$ alkyl or $C_{1-6}$ haloalkyl;
$R_4$ is selected from $C_{1-6}$ alkyl or $C_{3-7}$ cycloalkyl;
$R_6$ is independently selected from H, $C_{1-6}$ alkyl or $C_{1-6}$ haloalkyl.

14. The compound, or a pharmaceutically acceptable salt, enantiomer, diastereomer, racemate, or mixture thereof according to claim 3, which is a compound of formula (II-5), or a pharmaceutically acceptable salt, enantiomer, diastereomer, racemate, or mixture thereof:

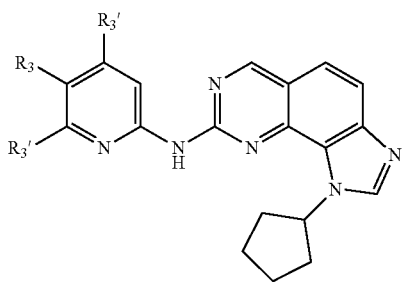

(II-5)

wherein,
$R_3$ is selected from

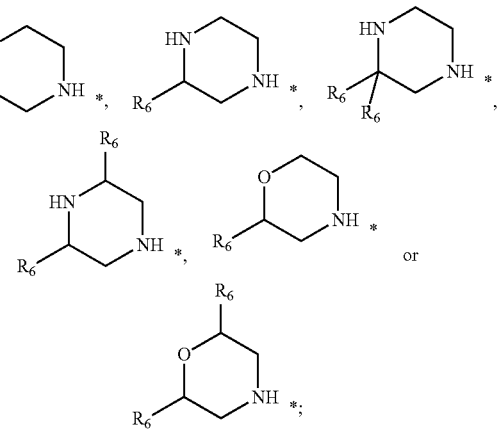

$R_3'$ is independently selected from H or $C_{1-6}$ alkyl;
$R_6$ is independently selected from H, $C_{1-6}$ alkyl or $C_{1-6}$ haloalkyl.

15. The compound, or a pharmaceutically acceptable salt, enantiomer, diastereomer, racemate, or mixture thereof according to claim 1, which is a compound of formula (III), or a pharmaceutically acceptable salt, enantiomer, diastereomer, racemate, or mixture thereof:

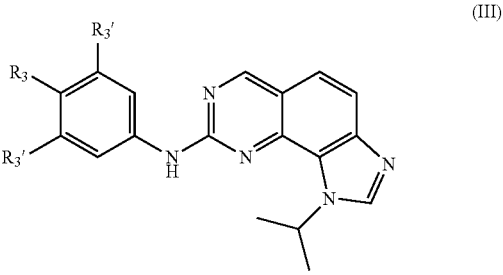

(III)

wherein,
$R_3$ is selected from

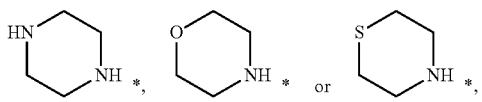

any of which is optionally substituted with 1, 2, 3 or 4 $R_6$ groups;
$R_3'$ is independently selected from H, halogen or $C_{1-6}$ alkyl;
$R_6$ is independently selected from H, $C_{1-6}$ alkyl, $C_{1-6}$ haloalkyl or —$C_{0-6}$ alkylene-$OR_a$;
$R_a$ is selected from H or $C_{1-6}$ alkyl.

16. The compound, or a pharmaceutically acceptable salt, enantiomer, diastereomer, racemate, or mixture thereof according to claim 15, wherein
$R_3$ is 3- to 7-membered heterocyclyl, which is optionally substituted with 1 or 2 $R_6$ groups;
$R_3'$ is independently selected from H, halogen, $C_{1-6}$ alkyl or —$OR_a$;

$R_6$ is independently selected from H, $-NH_2$, $-NHC_{1-6}$ alkyl, $-N(C_{1-6}$ alkyl$)_2$, $C_{1-6}$ alkyl or $C_{1-6}$ haloalkyl;
$R_a$ is selected from H or $C_{1-6}$ alkyl.
17. The compound, or the pharmaceutically acceptable salt, enantiomer, diastereomer, or racemate thereof according to claim 1, wherein the said compound is selected from
I-1
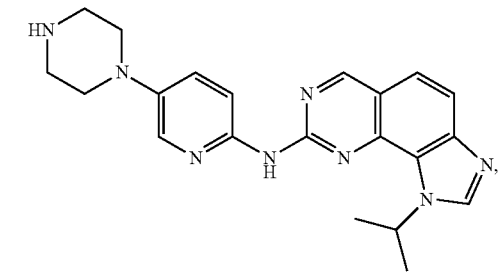
I-2
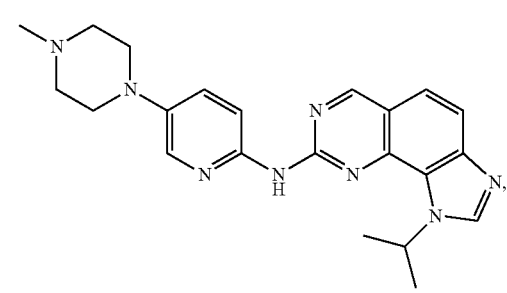
I-3
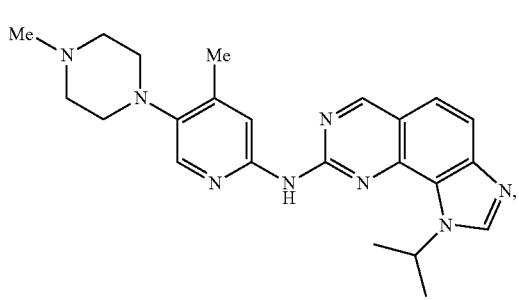
I-4
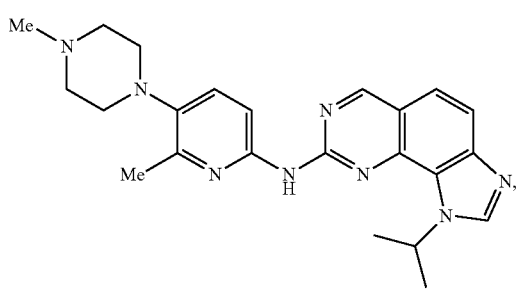
I-5
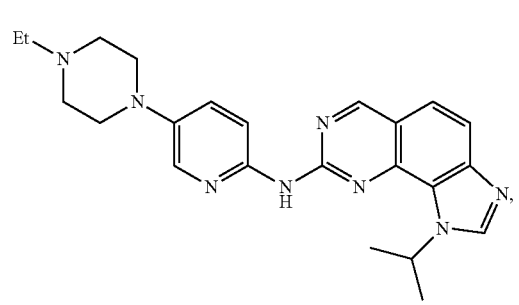
-continued
I-6
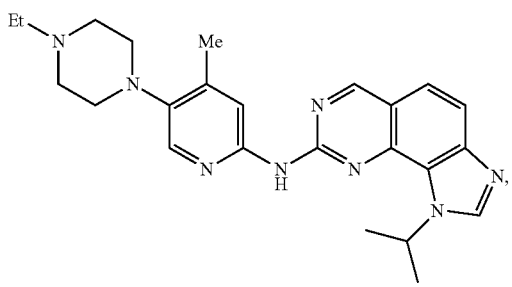
I-7
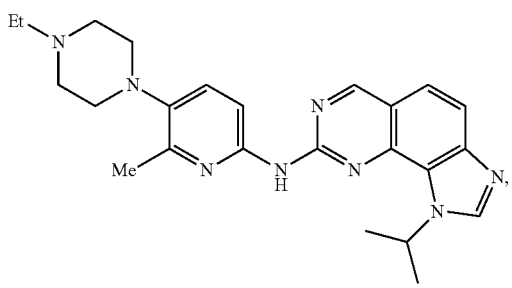
I-8
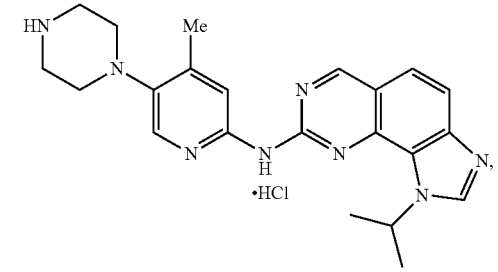
I-9
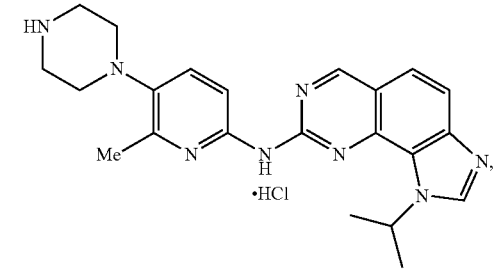
I-10
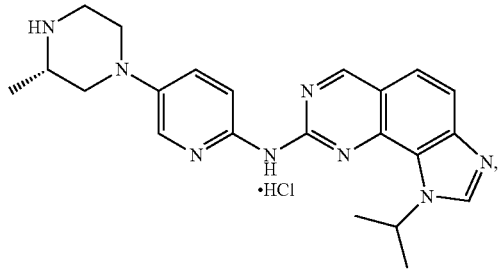

-continued
I-11
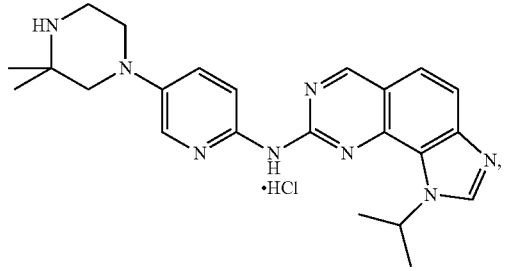
·HCl
I-12
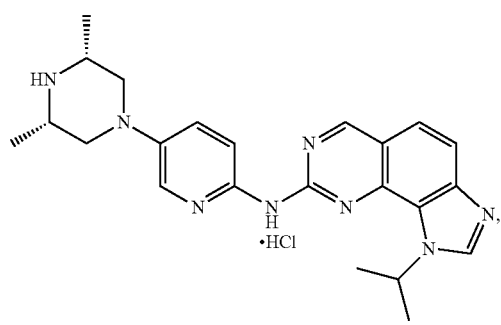
·HCl
I-13
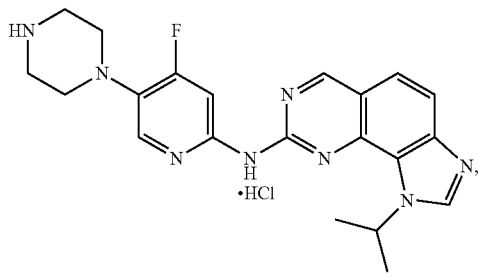
·HCl
I-14
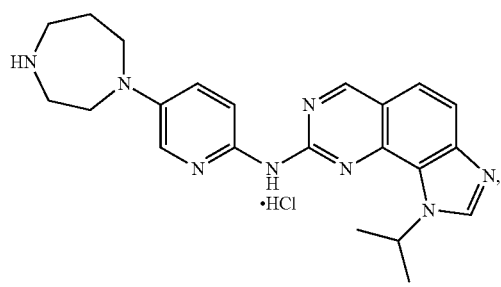
·HCl
I-15
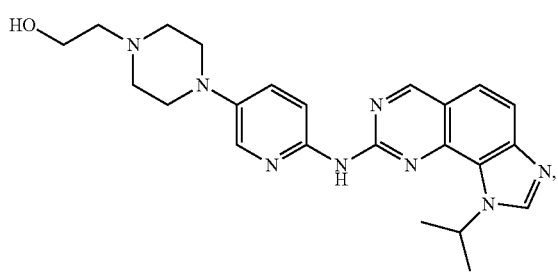
-continued
I-16
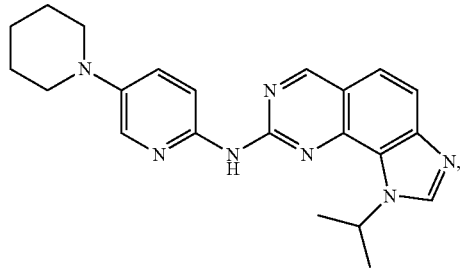
I-17
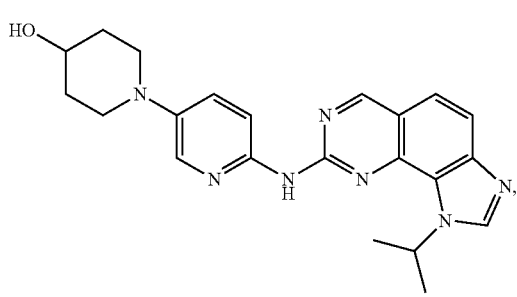
I-18
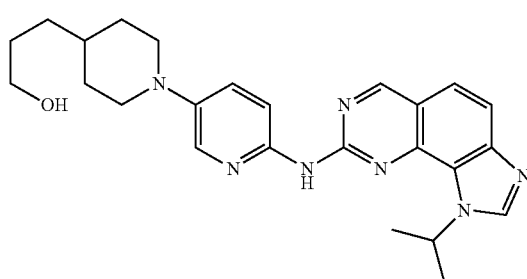
I-19
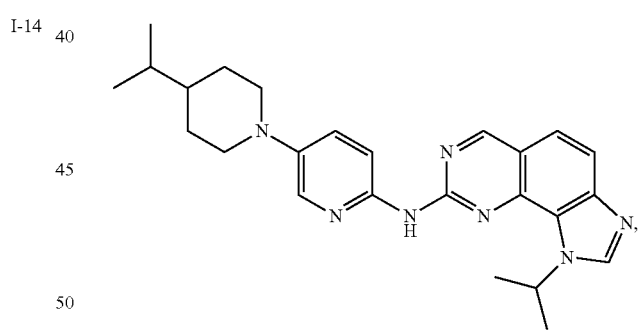
I-20
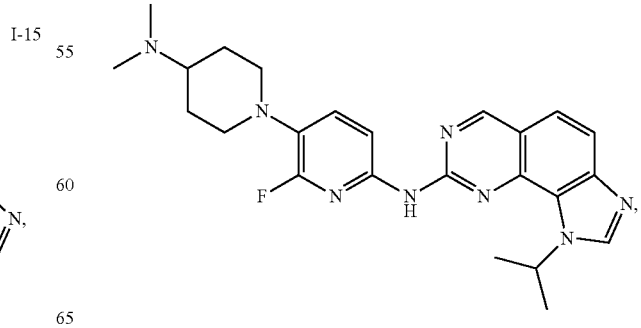

I-21
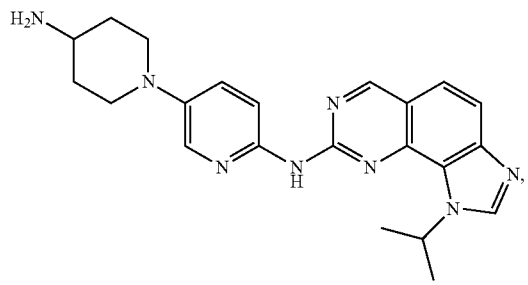
I-22
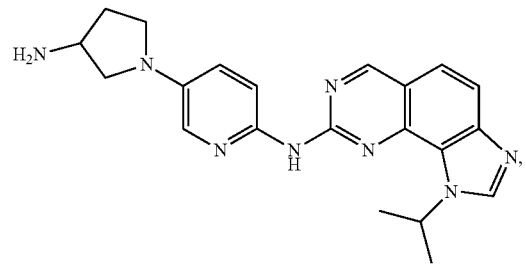
I-23
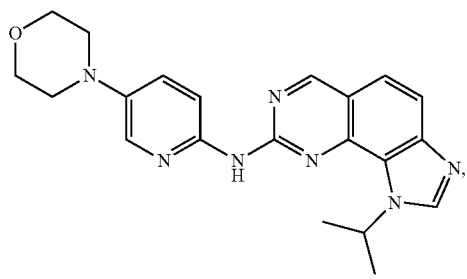
I-24
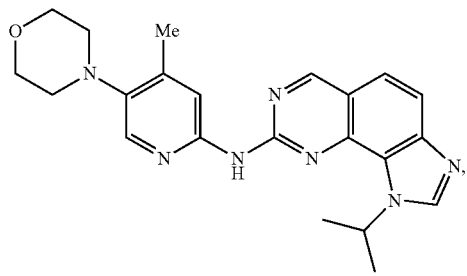
I-25
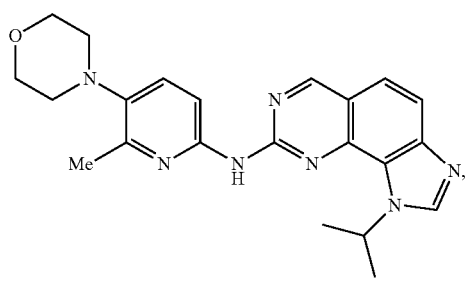
I-26
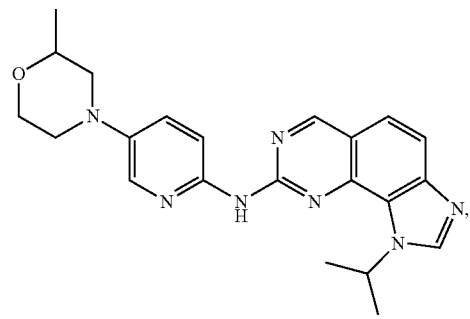
I-27
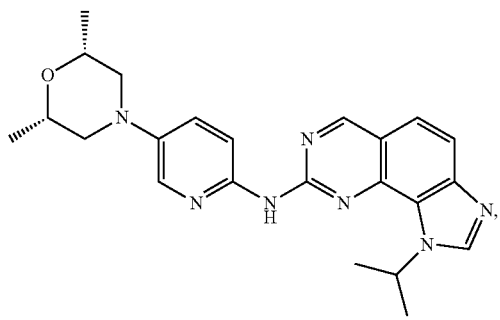
I-28
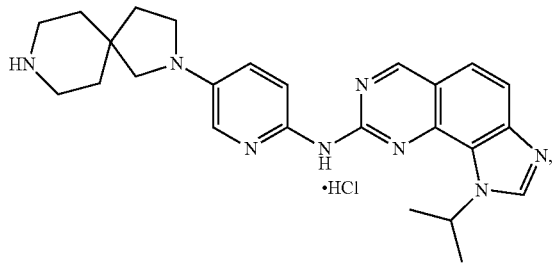
I-29
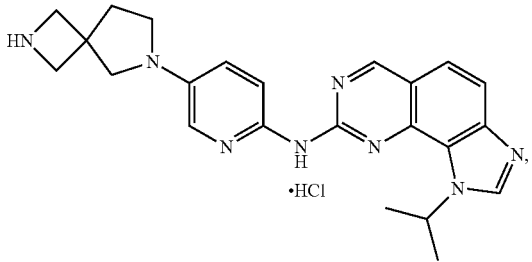
I-30
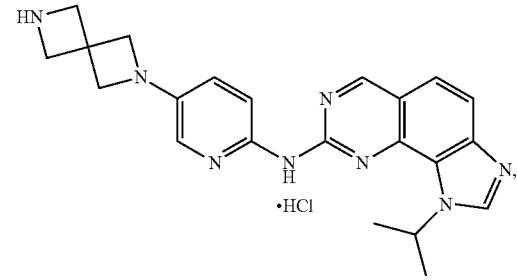

I-31
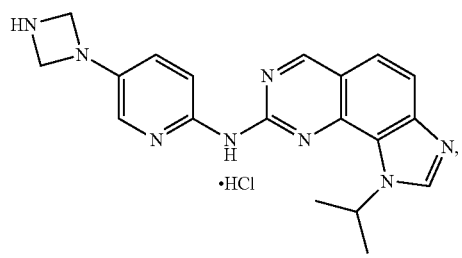
I-32
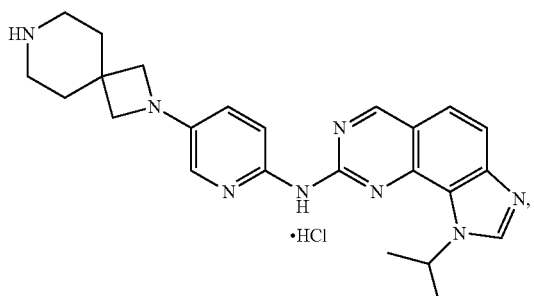
I-33
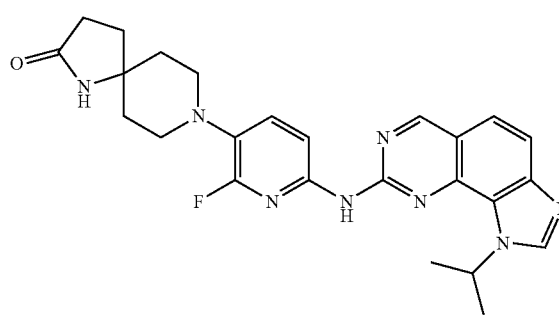
I-34
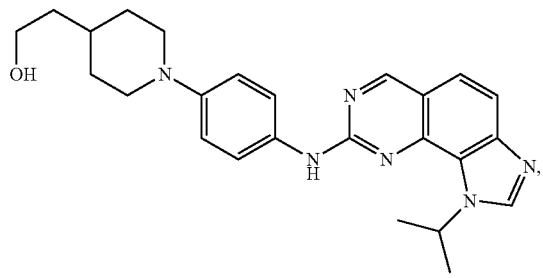
I-35
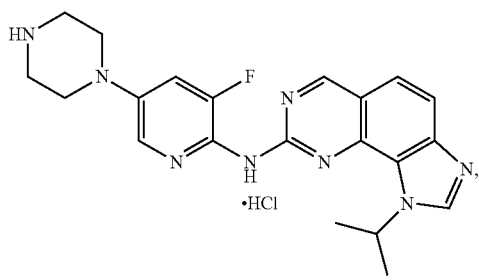
I-36
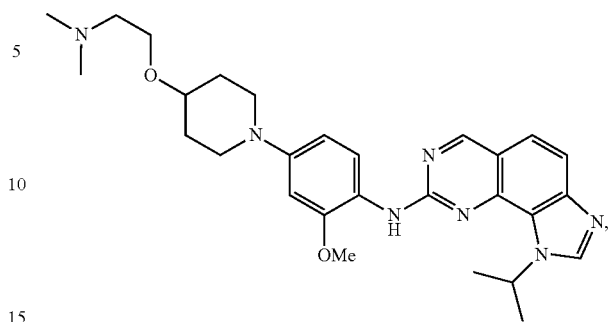
I-37
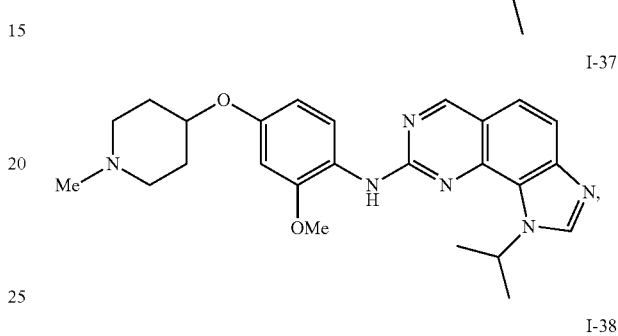
I-38
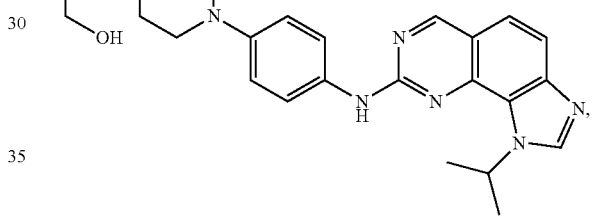
I-39
I-40
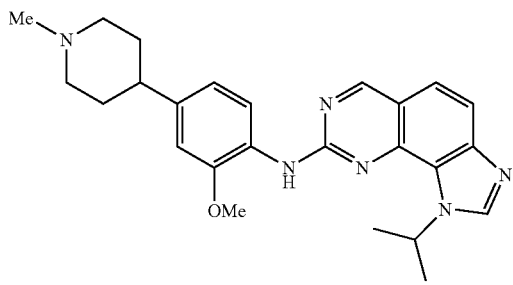

I-41
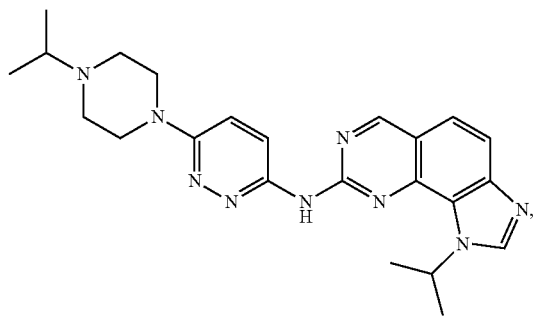
I-42
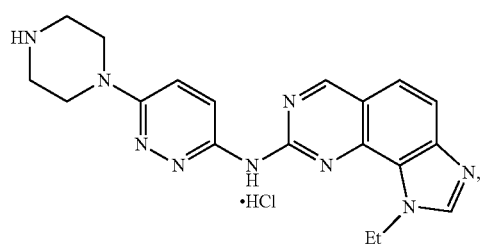
I-43
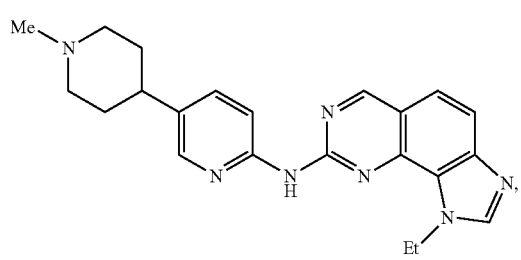
I-44
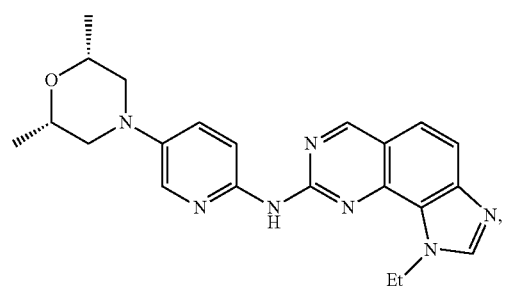
I-45
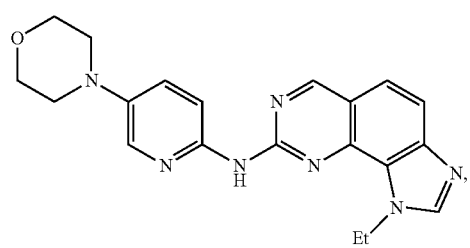
I-46
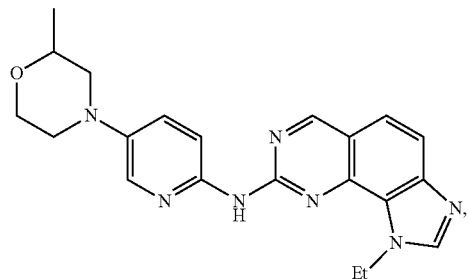
I-47
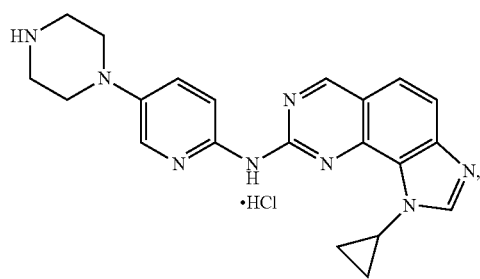
I-48
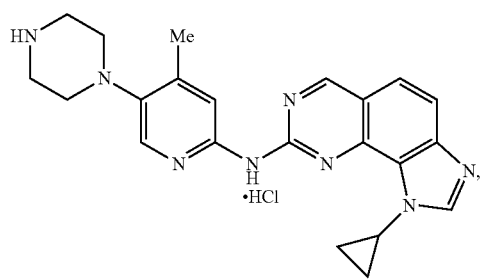
I-49
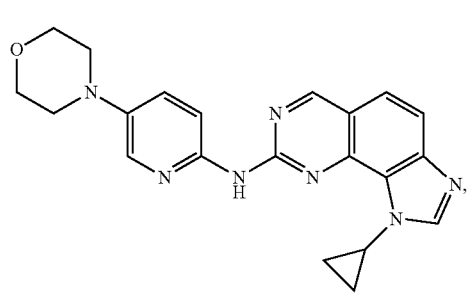
I-50
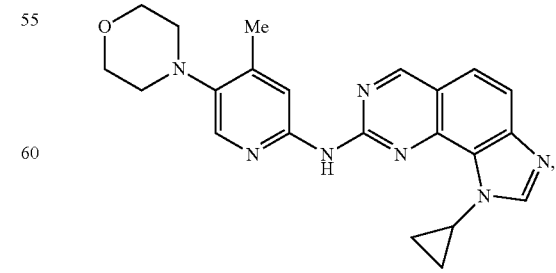

I-51
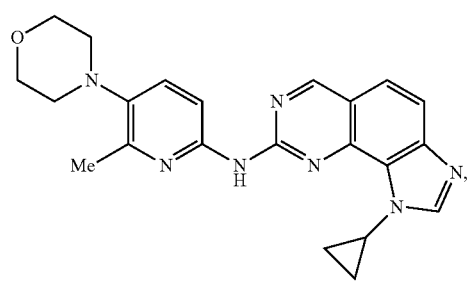
I-52
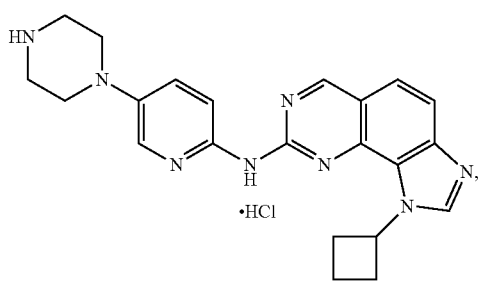
I-53
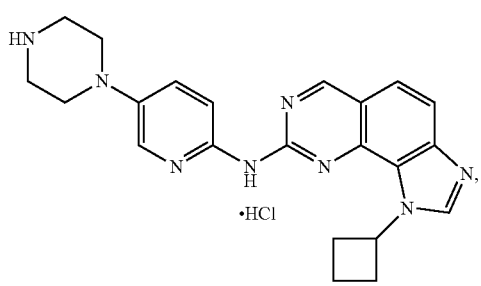
I-54
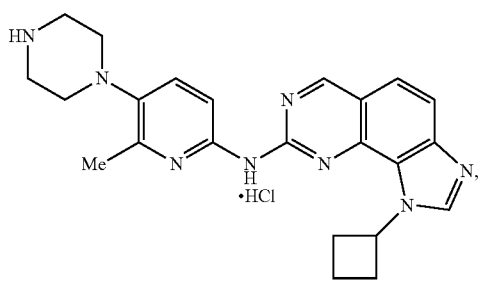
I-55
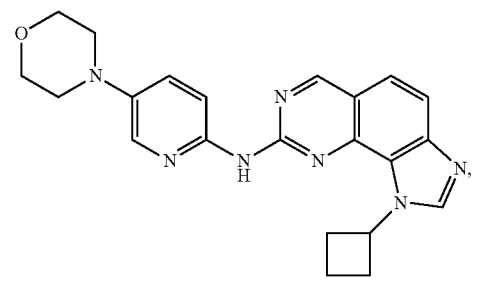
I-56
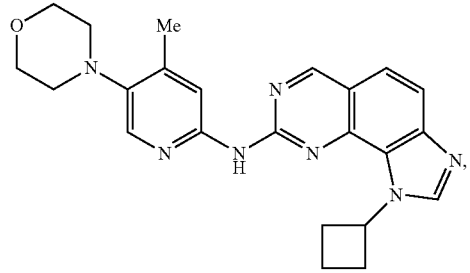
I-57
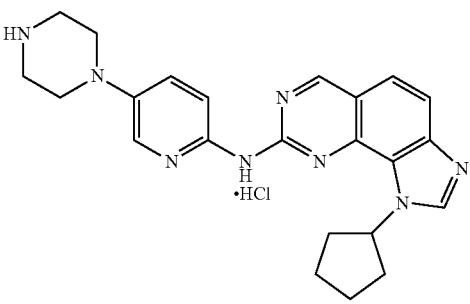
I-58
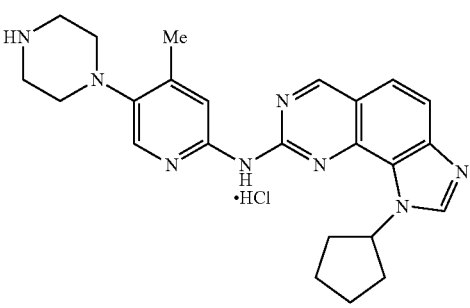
I-59
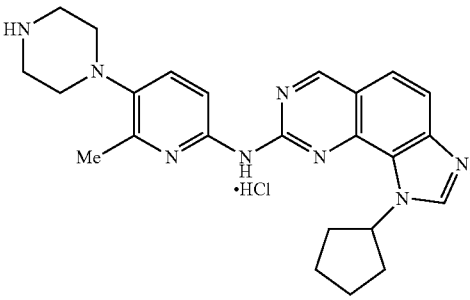
I-60
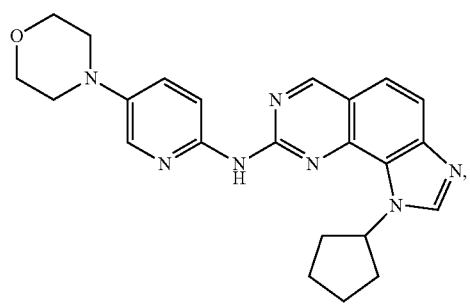

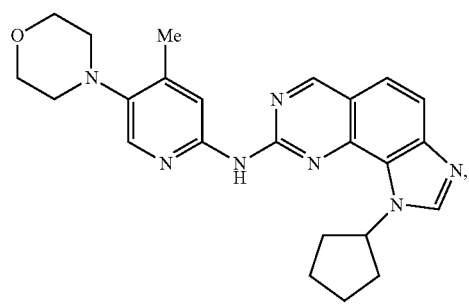
I-61
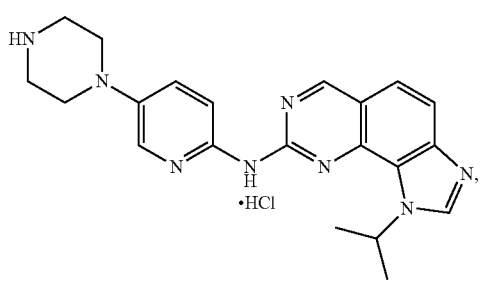
I-62
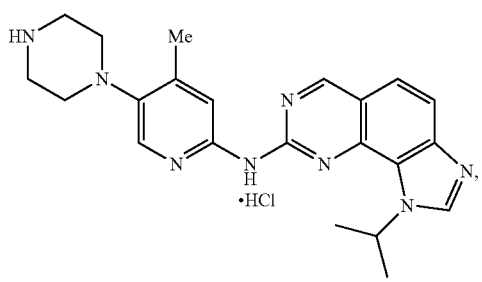
I-63
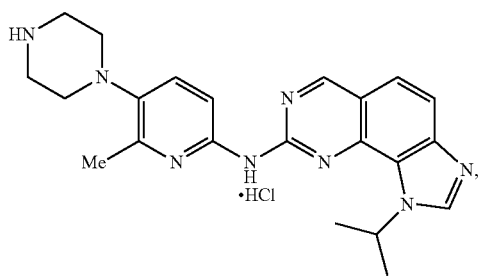
I-64
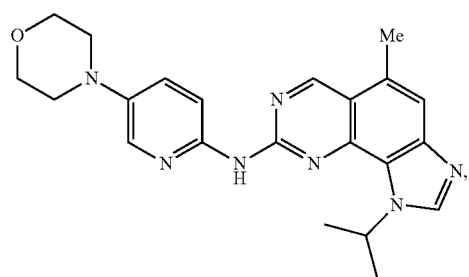
I-65
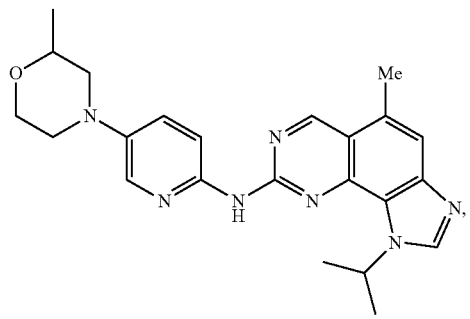
V-66
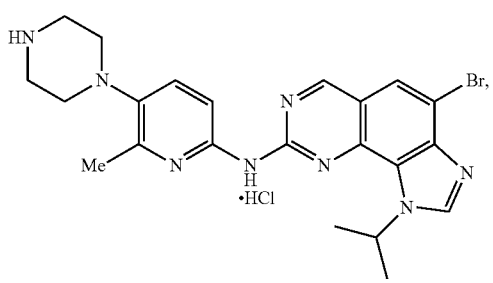
I-67
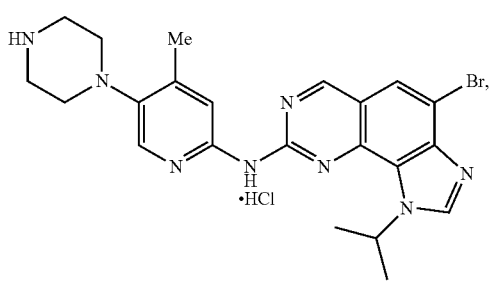
I-68
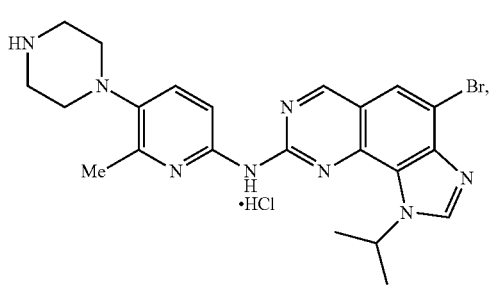
I-69
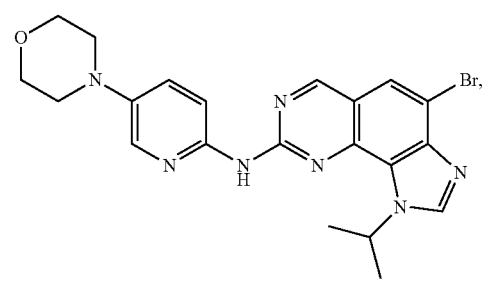
I-70

-continued
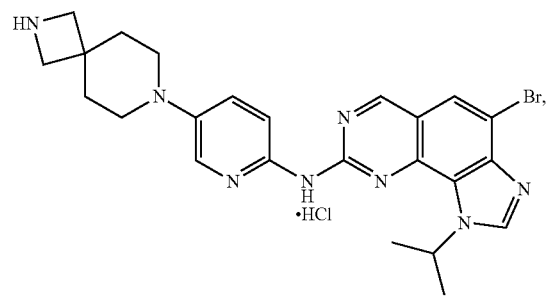
I-71
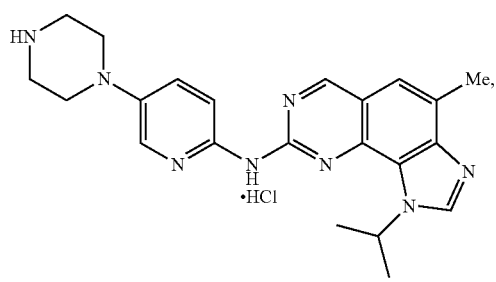
I-72
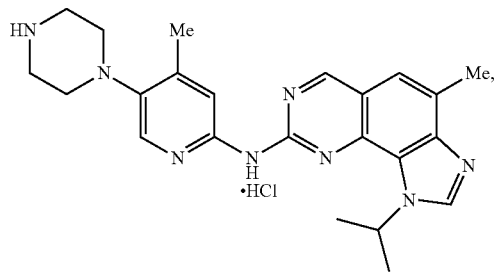
I-73
-continued
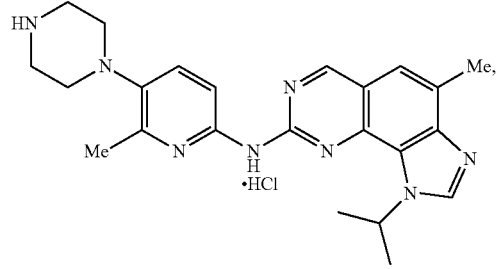
I-74
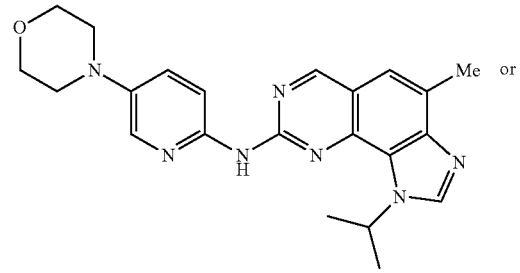
I-75
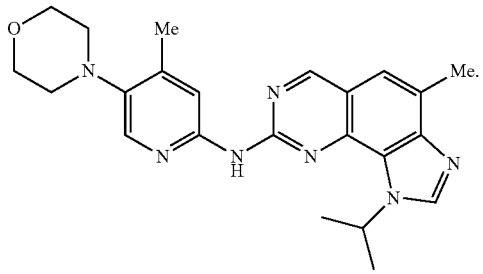
I-76
18. A pharmaceutical composition, comprising:
the compound, or the pharmaceutically acceptable salt, enantiomer, diastereomer, or racemate thereof according to claim 1; and
a pharmaceutically acceptable excipient;
optionally, the pharmaceutical composition further comprises one or more other therapeutic agents.
* * * * *